US012807970B2

(12) United States Patent
Akbari et al.

(10) Patent No.: US 12,807,970 B2
(45) Date of Patent: Nov. 24, 2026

(54) ENGINEERED REPRODUCTIVE ISOLATION IN ANIMALS

(71) Applicant: The Regents of the University of California, Oakland, CA (US)

(72) Inventors: Omar Akbari, La Jolla, CA (US); Anna Buchman, La Jolla, CA (US)

(73) Assignee: The Regents of the University of California

( * ) Notice: Subject to any disclaimer, the term of this patent is extended or adjusted under 35 U.S.C. 154(b) by 843 days.

(21) Appl. No.: 18/011,704

(22) PCT Filed: Jun. 23, 2021

(86) PCT No.: PCT/US2021/038595
§ 371 (c)(1),
(2) Date: Dec. 20, 2022

(87) PCT Pub. No.: WO2021/262794
PCT Pub. Date: Dec. 30, 2021

(65) Prior Publication Data

US 2023/0416783 A1 Dec. 28, 2023

Related U.S. Application Data

(60) Provisional application No. 63/042,614, filed on Jun. 23, 2020.

(51) Int. Cl.
*C12N 15/90* (2006.01)
*A01K 67/68* (2025.01)
*C07K 14/47* (2006.01)
*C12N 9/22* (2006.01)
*C12N 15/11* (2006.01)

(52) U.S. Cl.
CPC ............ *C12N 15/902* (2013.01); *A01K 67/68* (2025.01); *C07K 14/4705* (2013.01); *C12N 9/22* (2013.01); *C12N 15/111* (2013.01); *A01K 2217/072* (2013.01); *A01K 2227/706* (2013.01); *A01K 2267/02* (2013.01); *C12N 2310/20* (2017.05)

(58) Field of Classification Search
None
See application file for complete search history.

(56) References Cited

PUBLICATIONS

Maselko et al., Engineering multiple species-like genetic incompatibilities in insects, bioRxiv, Apr. 5, 2020 (Year: 2020).*
Flybase, Dmel\M{nanos-Cas9.P}ZH-2A page, 2025, https://flybase.org/reports/FBti0159183.html (Year: 2025).*
Basset et al., Highly efficient targeted mutagenesis of *drosophila* with the CRISPR/Cas9 System, Cell Reports, vol. 4, Issue 1, pp. 220-228, Jul. 2013 (Year: 2013).*
Gilbert et al., CRISPR-mediated modular RNA-guided regulation of transcription in eukaryotes, Cell, 154(2):442-451, Jul. 2013 (Year: 2013).*
Guilinger et al., Fusion of Catalytically inactive Cas9 to Fokl nuclease improves the specificity of genome modification, Nature Biotechnology, 32, 557-582, Apr. 2014 (Year: 2014).*
Carvalho et al., Suppression of a field population of Aedes Aegypti in Brazil by sustained release of transgenic male mosquitoes, PLOS Neglected Tropical Diseases, Jul. 2015 (Year: 2015).*
Akbari et al., "A synthetic gene drive system for local, reversible modification and suppression of insect populations," Current biology, Apr. 22, 2013, 23(8):671-677.
Asokan et al., "The AAV vector toolkit: poised at the clinical crossroads, " Molecular Therapy, Apr. 1, 2012, 20(4):699-708.
Baron et al., "Recent advances in viral vectors in veterinary vaccinology," Current opinion in virology, Apr. 1, 2018, 29:1-7.
Barry, "Single-cycle adenovirus vectors in the current vaccine landscape," Expert review of vaccines, Feb. 1, 2018, 17(2): 23 pages.
Bischof et al., "An optimized transgenesis system for *Drosophila* using germ-line-specific φC31 integrases," Proceedings of the National Academy of Sciences, Feb. 27, 2007, 104(9):3312-3317.
Boeke et al., "The genome project-write," Science, Jul. 8, 2016, 353(6295): 4 pages.
Buchman et al., "Broad dengue neutralization in mosquitoes expressing an engineered antibody," PLoS pathogens, Jan. 16, 2020, 16(1):e1008103, 1-20.
Buchman et al., "Engineered reciprocal chromosome translocations drive high threshold, reversible population replacement in *Drosophila*," ACS synthetic biology, Apr. 2, 2018, 7(5): 28 pages.
Buchman et al., "Engineered resistance to Zika virus in transgenic Aedes aegypti expressing a polycistronic cluster of synthetic small RNAs," Proceedings of the National Academy of Sciences, Feb. 26, 2019, 116(9):3656-3661.
Burgos et al., "The impact of herbicide-resistant rice technology on phenotypic diversity and population structure of United States weedy rice," Plant physiology, Nov. 2014, 166(3):1208-1220.
Cai et al., "Lentiviral delivery of proteins for genome engineering," Current Gene Therapy, Jun. 1, 2016, 16(3):194-206.
Champer et al., "Cheating evolution: engineering gene drives to manipulate the fate of wild populations," Nature Reviews Genetics, Mar. 2016, 17(3):146-159.

(Continued)

*Primary Examiner* — Allison M Fox
*Assistant Examiner* — Marisol Ann O'Neill
(74) *Attorney, Agent, or Firm* — Fish & Richardson P.C.

(57) ABSTRACT

Provided herein are methods of engineering a reproductive barrier in an insect including (a) introducing into a first insect a first nucleic acid sequence, where the first nucleic acid sequence targets a genomic sequence, where the genomic sequence is proximal to a transcription start site of a gene product; and (b) introducing into a second insect a second nucleic acid sequence encoding a nuclease-deficient endonuclease; and (c) genetically crossing the first insect with the second insect, where the second insect includes a second copy of the genomic sequence where the second copy of the genomic sequence is proximal to a transcription start site of a second copy of the gene product.

14 Claims, 24 Drawing Sheets

Specification includes a Sequence Listing.

(56) References Cited

PUBLICATIONS

Champer et al., "Novel CRISPR/Cas9 gene drive constructs reveal insights into mechanisms of resistance allele formation and drive efficiency in genetically diverse populations," PLoS genetics, Jul. 20, 2017, 13(7):e1006796, 18 pages.
Chavez et al., "Comparison of Cas9 activators in multiple species," Nature methods, Jul. 2016, 13(7): 16 pages.
Dobin et al., "STAR: ultrafast universal RNA-seq aligner," Bioinformatics, Jan. 1, 2013, 29(1):15-21.
Edgington et al., "Population dynamics of engineered underdominance and killer-rescue gene drives in the control of disease vectors," PLoS computational biology, Mar. 23, 2018, 14(3):e1006059, 28 pages.
Esvelt et al., "Emerging Technology: Concerning RNA-guided gene drives for the alteration of wild populations," eLife, 2014, 3:e03401, 21 pages.
Ewen-Campen et al., "Optimized strategy for in vivo Cas9-activation in Drosophila," Proceedings of the National Academy of Sciences, Aug. 29, 2017, 114(35):9409-9414.
Gibson et al., "Enzymatic assembly of DNA molecules up to several hundred kilobases, " Nature methods, May 2009, 6(5): 5 pages.
Grenier et al., "Global diversity lines—a five-continent reference panel of sequenced *Drosophila melanogaster* strains," G3: Genes, Genomes, Genetics, Apr. 1, 2015, 5(4):593-603.
International Preliminary Report on Patentability in International Appln. No. PCT/US2021/038595. mailed on Jan. 5, 2023,7 pages.
International Search Report and Written Opinion in International Appln. No. PCT/US2021/038595, mailed on Oct. 25, 2021, 10 pages.
Kandul et al., "Assessment of a split homing based gene drive for efficient knockout of multiple genes," G3: Genes, Genomes, Genetics, Feb. 1, 2020, 10(2):827-837.
Kandul et al., "Transforming insect population control with precision guided sterile males with demonstration in flies," Nature Communications, 2019, 10(84): 12 pages.
Kurian et al., "Retroviral vectors," Molecular Pathology, Aug. 2000, 53(4):173-176.
Kyrou et al., "A CRISPR-Cas9 gene drive targeting doublesex causes complete population suppression in caged *Anopheles gambiae* mosquitoes," Nature biotechnology, Nov. 2018, 36(11):1062-1066.
Lajoie et al., "Genomically recoded organisms expand biological functions," science, Oct. 18, 2013, 342(6156): 11 pages.
Leftwich et al., "Recent advances in threshold-dependent gene drives for mosquitoes," Biochemical Society Transactions, Oct. 19, 2018, 46(5):1203-212.
Li et al., "Germline Cas9 expression yields highly efficient genome engineering in a major worldwide disease vector, Aedes aegypti," Proceedings of the National Academy of Sciences, Dec. 5, 2017, 114(49):E10540-E10549.
Liao et al., "featureCounts: an efficient general purpose program for assigning sequence reads to genomic features," Bioinformatics, Apr. 1, 2014, 30(7):923-930.
Lin et al., "In vivo transcriptional activation using CRISPR/Cas9 in *Drosophila*," Genetics, Oct. 1, 2015, 201(2):433-442.
Love et al., "Moderated estimation of fold change and dispersion for RNA-seq data with DESeq2," Genome biology, Dec. 2014, 15(550):1-21.
Marshall et al., "Can CRISPR-based gene drive be confined in the wild? A question for molecular and population biology," ACS chemical biology, Feb. 16, 2018, 13(2):424-430.
Marshall et al., "Confinement of gene drive systems to local populations: a comparative analysis," Journal of Theoretical Biology, Feb. 7, 2012, 294: 41 pages.
Maselko et al., "Engineering species-like barriers to sexual reproduction," Nature communications, Oct. 12, 2017, 8(1):883, 7 pages.
Milone et al., "Clinical use of lentiviral vectors," Leukemia, Jul. 2018, 32(7):1529-1541.
Moreno, "Design and construction of synthetic species", PLoS One, Jul. 25, 2012, 7(7):e39054, 6 pages.
Oberhofer et al., "Cleave and Rescue, a novel selfish genetic element and general strategy for gene drive," Proceedings of the National Academy of Sciences, Mar. 26, 2019, 116(13):6250-6259.
Port et al., "Augmenting CRISPR applications in Drosophila with tRNA-flanked sgRNAs," Nature methods, Oct. 2016, 13(10): 12 pages.
Port et al., "Optimized CRISPR/Cas tools for efficient germline and somatic genome engineering in *Drosophila*," Proceedings of the National Academy of Sciences, Jul. 22, 2014, 111(29):E2967-2976.
Reeves et al., "First steps towards underdominant genetic transformation of insect populations, " PLoS One, May 20, 2014, 9(5):e97557, 9 pages.
Rovner et al., "Recoded organisms engineered to depend on synthetic amino acids," Nature, Feb. 5, 2015, 518(7537):89-93.
Tatsis et al., "Adenoviruses as vaccine vectors," Molecular Therapy, Oct. 1, 2004, 10(4):616-629.
Thurmond et al., "FlyBase 2.0: the next generation," Nucleic acids research, Jan. 8, 2019, 47(D1):D759-D765.
Waters et al., "Rationally-engineered reproductive barriers using CRISPR & CRISPRa: an evaluation of the synthetic species concept in *Drosophila melanogaster*," Scientific reports, Sep. 3, 2018, 8(1):13125, 14 pages.
Wold et al., Adenovirus vectors for gene therapy, vaccination and cancer gene therapy, Current gene therapy, Dec. 1, 2013, 13(6): 26 pages.
Zheng et al., "Lentiviral Vectors and Adeno-Associated Virus Vectors: Useful Tools for Gene Transfer in Pain Research," The Anatomical Record, May 2018, 301(5):825-836.

* cited by examiner c

SPECIES-like extreme underdominance

Chromosomal translocations

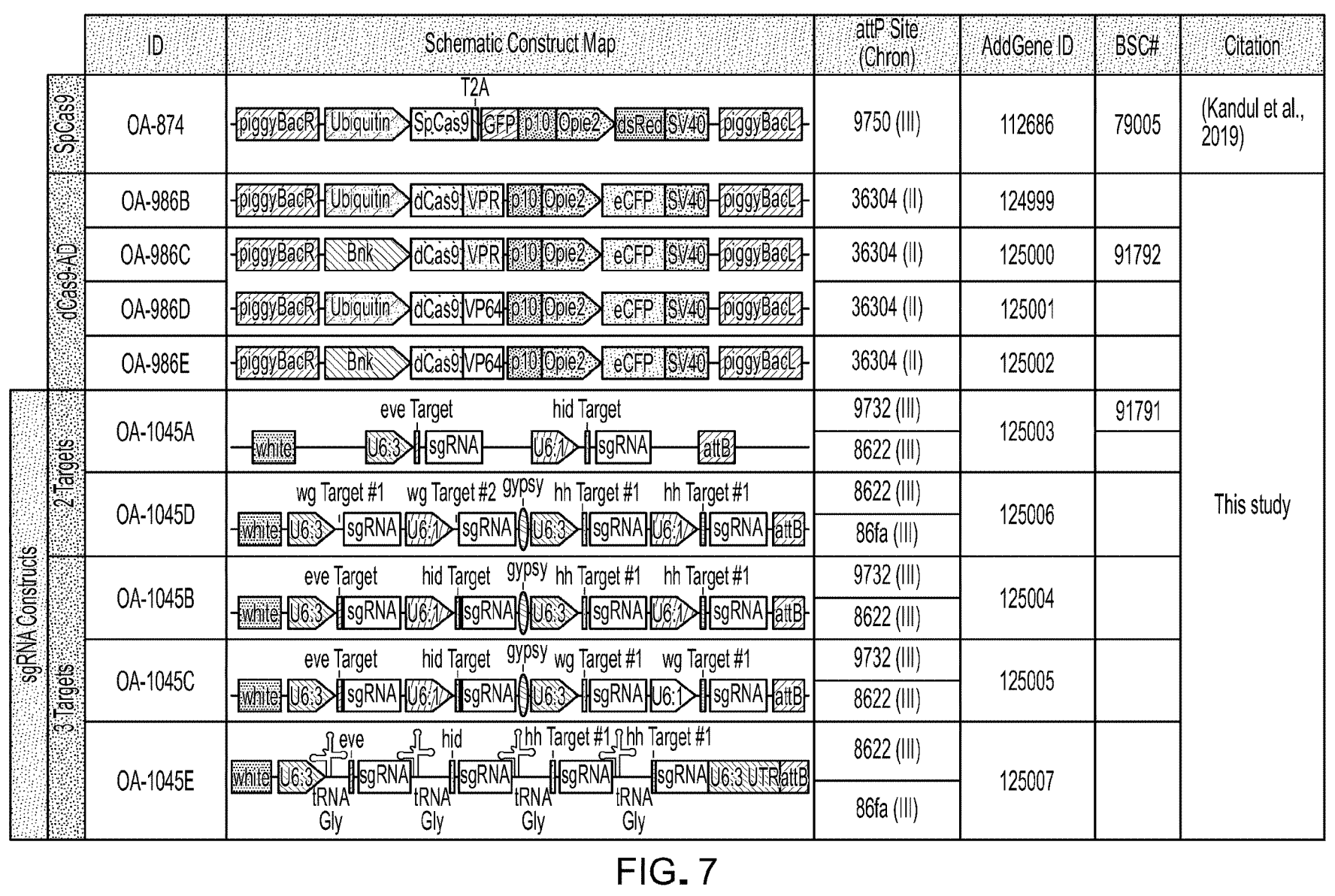

| | ID | Schematic Construct Map | attP Site (Chron) | AddGene ID | BSC# | Citation |
|---|---|---|---|---|---|---|
| SpCas9 | OA-874 | piggyBacR – Ubiquitin – SpCas9 – T2A – GFP – p10 – Opie2 – dsRed – SV40 – piggyBacL | 9750 (III) | 112686 | 79005 | (Kandul et al., 2019) |
| dCas9-AD | OA-986B | piggyBacR – Ubiquitin – dCas9 – VPR – p10 – Opie2 – eCFP – SV40 – piggyBacL | 36304 (II) | 124999 | | This study |
| dCas9-AD | OA-986C | piggyBacR – Bnk – dCas9 – VPR – p10 – Opie2 – eCFP – SV40 – piggyBacL | 36304 (II) | 125000 | 91792 | This study |
| dCas9-AD | OA-986D | piggyBacR – Ubiquitin – dCas9 – VP64 – p10 – Opie2 – eCFP – SV40 – piggyBacL | 36304 (II) | 125001 | | This study |
| dCas9-AD | OA-986E | piggyBacR – Bnk – dCas9 – VP64 – p10 – Opie2 – eCFP – SV40 – piggyBacL | 36304 (II) | 125002 | | This study |
| sgRNA Constructs: 2 Targets | OA-1045A | white – U6:3 – [eve Target] – sgRNA – U6:1 – [hid Target] – sgRNA – attB | 9732 (III)<br>8622 (III) | 125003 | 91791 | This study |
| sgRNA Constructs: 2 Targets | OA-1045D | white – U6:3 – [wg Target #1] – sgRNA – U6:1 – [wg Target #2] – sgRNA – [gypsy] – U6:3 – [hh Target #1] – sgRNA – U6:1 – [hh Target #1] – sgRNA – attB | 8622 (III)<br>86fa (III) | 125006 | | This study |
| sgRNA Constructs: 3 Targets | OA-1045B | white – U6:3 – [eve Target] – sgRNA – U6:1 – [hid Target] – sgRNA – [gypsy] – U6:3 – [hh Target #1] – sgRNA – U6:1 – [hh Target #1] – sgRNA – attB | 9732 (III)<br>8622 (III) | 125004 | | This study |
| sgRNA Constructs: 3 Targets | OA-1045C | white – U6:3 – [eve Target] – sgRNA – U6:1 – [hid Target] – sgRNA – [gypsy] – U6:3 – [wg Target #1] – sgRNA – U6:1 – [wg Target #1] – sgRNA – attB | 9732 (III)<br>8622 (III) | 125005 | | This study |
| sgRNA Constructs: 3 Targets | OA-1045E | white – U6:3 – tRNA Gly – [eve] – sgRNA – tRNA Gly – [hid] – sgRNA – tRNA Gly – [hh Target #1] – sgRNA – tRNA Gly – [hh Target #1] – sgRNA – U6:3 UTR – attB | 8622 (III)<br>86fa (III) | 125007 | | This study |

FIG. 7

| | Transgenes Used | | | | |
|---|---|---|---|---|---|
| Synthetic Species | Cas9 | dCas9-AD | gRNAs | attP Site (Chrom) | Citation |
| A1 | 874W attP Site 9750 Chrom III | OA-986C attP Site 36304 Chrom III | OA-1045A | 9732 (III) | This study |
| A2 | | | | 8622 (III) | |
| B1 | | | OA-1045B | 9732 (III) | |
| B2 | | | | 8622 (III) | |
| C1 | | | OA-1045C | 9732 (III) | |
| C2 | | | | 8622 (III) | |
| D1 | | | OA-1045D | 8622 (III) | |
| D2 | | | | 86Fa (III) | |

FIG. 9

*9732 1045A (eve+hid) - A1*

```
       WT | CAGCAGCGCATCCACTCTCAGCACCGCACGATTAGCACCGTTCCGCTCAG  SEQ ID NO: 41
        1 | CAGCAGCGCATCCACTCTC-------------CAGCACCGTTCCGCTCAG  SEQ ID NO: 42
eve     2 | CAGCAGCGCATC------CAGCACCGCACGATTAGCACCGTTCCGCTCAG  SEQ ID NO: 43
        3 | CAGCAGCGCAT------TCAGCACCGCACGATTAGCACCGTTCCGCTCAG  SEQ ID NO: 44
        4 | CAGCAGCGCATCCA--CTCAGCACCGCACGATTAGCACCGTTCCGCTCAG  SEQ ID NO: 45
        1 | CAGCAGCGCATCCACT------ACCGCACGATTAGCACCGTTCCGCTCAG  SEQ ID NO: 46
       WT | CAAGTGTGCCTCCTTCA--TGCACGTGCATGTGCAGGAGAGGGAGCGAGA  SEQ ID NO: 47
hid    18 | CAAGTGTGCCTCCTTCAGCTGCACGTGCATGTGCAGGAGAGGGAGCGAGA  SEQ ID NO: 48
                 PAM        sgRNA
```

*8622 1045A (eve+hid) - A2*

```
       WT | CAGCAGCGCATCCACTCTCAGCACCGCACGATTAGCACCGTTCCGCTCAG  SEQ ID NO: 49
eve    11 | CAGCAGCGCATCCACTCT----------------GCACCGTTCCGCTCAG  SEQ ID NO: 50
        1 | ------------------CAGCACCGCACGATTAGCACCGTTCCGCTCAG  SEQ ID NO: 51
       WT | CAAGTGTGCCTCCT--TC--A--TGCACGTGCATGTGCAGGAGAGGGAGC  SEQ ID NO: 52
        2 | CAAGTGTGCCTCCT--TC--A--T--ACGTGCATGTGCAGGAGAGGGAGC  SEQ ID NO: 53
        1 | CAAGTGTGCCTCCT--TCATA--T--ACGTGCATGTGCAGGAGAGGGAGC  SEQ ID NO: 54
hid     3 | CAAGTGTGCCTCCT--TC--A--T----GTGCATGTGCATGAGAGGGAGC  SEQ ID NO: 55
        2 | CAAGTGTGCCTCCT--TC--ATGTGCACGTGCATGTGCAGGAGAGGGAGC  SEQ ID NO: 56
        1 | CAA-----------------------ATGTGCATGTGCAGGAGAGGGAGA  SEQ ID NO: 57
        3 | CAAGT-----------------------GTGCATGTGCAGGAGAGGGAGA  SEQ ID NO: 58
        1 | CAAGTGTGCCTCCTTCTCGCA--TGCACGTGCATGTGCAGGAGAGGGAGC  SEQ ID NO: 59
        1 | CAAGTGTGCCTCCTTCTCGCA--TGCACGTGCATGTGCAGGAGAGGGAGA  SEQ ID NO: 60
                 PAM        sgRNA
```

FIG. 10

*9732 1045B (eve+hid+hh) - B1*

| | | | |
|---|---|---|---|
| *eve* | WT | CAGCAGCGCATCCACTCTCAGCAC---CGCACGATTAGCACCGTTCCGCT | SEQ ID NO: 61 |
| | 3 | ------------------CAGCAC---CGCACGATTAGCACCGTTCCGCT | SEQ ID NO: 62 |
| | 6 | CAGCAGCGCATC------CAGCAC---CGCACGATTAGCACCGTTCCGCT | SEQ ID NO: 63 |
| | 1 | CAGCAGCGCATCCACTCACCGGATGAGTGGACGATTAGCACCGTTCCGCT | SEQ ID NO: 64 |
| *hid* | WT | CAAGTGTGCCTCCTTCA--TGCACGTGCATGTGCAGGAGCGGGAGCGAGA | SEQ ID NO: 65 |
| | 12 | CAAGTGTGCCTCCTTCACGTGCACGTGCATGTGCAGGAGCGGGAGCGAGA | SEQ ID NO: 66 |
| | 2 | CAAGTGTGCCTCCTTC---TTCACGTGCATGTGCAGGAGCGGGAGCGAGA | SEQ ID NO: 67 |
| *hh* | WT | TCTGGTTGTCCCGCTTCCACTTCCCTTGCGCATAAGGCAGCATAAAAATGAACACCACAGCCGATCGAACGTCGAGTGGCATACGCACACAAT | SEQ ID NO: 68 |
| | 13 | TCTGGTTGTCCCGCTTCCACTTCCCTTG-----------------------------------------CGTCGAGTGGCATACGCACACAAT | SEQ ID NO: 69 |
| | 3 | CCTGAGTCTTCGGCTCTTATGTAC----------AAGCAATGTTGG----------------CAACAGATGTTGGATGGCATTGGCATAGTGT | SEQ ID NO: 70 |
| | 4 | CCTGAGTCTTCGGCTCTTATGTAC----------AAGCAATGTTGG----------------CAACAGATGTTGGATGGCATTGGCATA---T | SEQ ID NO: 71 |
| | 1 | CCTGAGTCTTCGGCTCTTATGTAC----------AAGCAATGTTGG----------------CAACAGATGTTGGATGGCATTGGC------T | SEQ ID NO: 72 |
| | 3 | CCTGAGTCTTCGGCTCTTATGT-------------------------ACAAGCAATGTTGGCAA-CAGATGTTGGATGGCATTGGCATAGTGT | SEQ ID NO: 73 |
| | 1 | CCTGAGTCTTCGGCTCTTATGT-------------------------ACAAGCAATGTTGGCAA-CAGATGTTGGATGGCATTGGCATA---T | SEQ ID NO: 74 |
| | 1 | CCTGAGTCTTCGGCTCTTATGT-------------------------ACAAGCAATGTTGGCAA-CAGATGTTGGATGGCATTGGC------T | SEQ ID NO: 75 |

PAM sgRNA PAM sgRNA

*8622 1045B (eve+hid+hh) - B2*

| | | | |
|---|---|---|---|
| *eve* | WT | CAGCAGCGCATCCACTCTCAGCACCGCACGATTAGCACCGTTCCGCTCAG | SEQ ID NO: 76 |
| | 10 | CAGCAGCGCATCCA----CAGCACCGCACGATTAGCACCGTTCCGCTCAG | SEQ ID NO: 77 |
| *hid* | WT | CAAGTGTGCCTCCTTCATGCACGTGCATGTGCAGGAGCGGGAGCGAGAGA | SEQ ID NO: 78 |
| | 10 | CAAGTGTGCCTCCTT----------CATGTGCAGGAGCGGGAGCGAGAGA | SEQ ID NO: 79 |
| *hh* | WT | TCTGGTTGTCCCGCTTCCACTTCCCTTGCGCATAAGGCAGCATAAAAATGAACACCACAGCCGATCGAACGTCGAGTGGCATACGCACACAAT | SEQ ID NO: 80 |
| | 4 | TCTGGTTGTCCCGCTTCCACTTCCCTT---------GCAGCATAAAAATGAACACCACAGCCGAT----CGTCGAGTGGCATACGCACACAAT | SEQ ID NO: 81 |
| | 8 | TCTGGTTGTCCCGCTTCCACTTCCCTT---------GCAGCATAAAAATGAACACCACAGCCGA-------TCGAGTGGCATACGCATACAAT | SEQ ID NO: 82 |

PAM sgRNA PAM sgRNA

FIG. 10 (Cont.)

*9732 1045C (eve+hid+wg) - C1*

```
eve  WT | CAGCAGCGCATCCACTCTCAGCACCGCACGATTAGCACCGTTCCGCTCAG   SEQ ID NO: 83
      6 | ------------------CAGCACCGCACGATTAGCACCGTTCCGCTCAG   SEQ ID NO: 84
      5 | CAGCA-------------CAGCACCGCACGATTAGCACCGTTCCGCTCAG   SEQ ID NO: 85
hid  WT | CAAGTGTGCCTCCTTCATGCACGTGCATGTGCAGGAGCGGGAGCGAGAGA   SEQ ID NO: 86
     20 | CAAGTGTGCCTCCTT----CACGTGCATGTGCAGGAGCGGGAGCGAGAGA   SEQ ID NO: 87
wg   WT | CTATGACGAAATTCATGAGGTTGCGCAAATAATCGGGCAATACAATCGATTACACCGAAAATGCCGGGCAGAGTTTTTCCATTTCCGCCATTT SEQ ID NO: 88
      1 | CTATGACGAAATTCATGAGGTTGCG----AAATCGGGCAATACAATCGATTACACCGAAAATGCCGGGCGAGTT----------------TTT SEQ ID NO: 89
      2 | CTATGACGAAATTCATGAGGTTG----------CGGGCAATACAATCGATTACACCGAAAATGCCGGGCCCGG-TTTTCCATTTCCGCCATTT SEQ ID NO: 90
      9 | CTATGACGAAATTCATGAGGTTGCGCAAAT-----------------------------------CGGGCAAGTTTTTCCATTTCCGCCATTT SEQ ID NO: 91
```

PAM sgRNA PAM sgRNA

*8622 1045C (eve+hid+wg) - C2*

```
eve  WT | CAGCAGCGCATCCACTCTCAGCACCGCACGATTAGCACCGTTCCGCTCAG   SEQ ID NO: 92
      4 | CAGCAGCGCATC--------------CACGATTAGCACCGTTCCGCTCAG   SEQ ID NO: 93
      8 | CAGCAGCGCATCCACTCC--GCACCGCACGATTAGCACCGTTCCGCTCAG   SEQ ID NO: 94
hid  WT | CAAGTGTGCCTCCTTCATG--------CACGTGCATGTGCAGGAGCGGGAG   SEQ ID NO: 95
     10 | CAAGTGTGCCTCCTTCATGCACATGCCACGTGCATGTGCAGGAGCGGGAG   SEQ ID NO: 96
wg   WT | CTATGACGAAATTCATGAGGTTGCGCAAATAATCGGGCAATACAATCGATTACACCGAAAATGCCGGGCAGAGTTTTTTCCATTTCCGCCATTT SEQ ID NO: 97
     14 | CTATGACGAAATTCATGAGGTTGC------------GCAATACAATCGATTACACCGAAAATGCCGGGC-GAGTTTTTTCCATTTCCGCCATTT SEQ ID NO: 98
```

PAM sgRNA PAM sgRNA

FIG. 10 (Cont.)

*8622 1045D (hh+wg) - D1*

```
    WT | TCTGGTTGTCCCGCTTCCACTTCCCTTGCGCATAAGGCAGCATAAAAATGAACACCACAGCCGATCGAACGTCGAGTGGCATACGCACACAAT  SEQ ID NO: 99
    13 | TCTGGTTGTCCCGCTTCCACTTCCCTTGCGCGT------------------------------------CGTCGAGTGGCATACGCACACAAT  SEQ ID NO: 100
hh   5 | CCTGAGTCTTCGGCTCTTATGT-------------------------ACAAGCAATGTTGGCAA-CAGATGTTGGATGGCATTGGCATAGTGT  SEQ ID NO: 101
     8 | CCTGAGTCTTCGGCTCTTATGT-------------------------ACAAGCAATGTTGGCAA-CAGATGTTGGATGGCATTGGCATA----  SEQ ID NO: 102
    WT | CTATGACGAAATTCATGAGGTTGCGCAAATAATCGGGCAATACAATCGATTACACCGAAAATGCCG----GGCAGAGTTTTTCCATTTCCGCC  SEQ ID NO: 103
     4 | CTATGACGAAATTCATGAGGTTG----------CGGGCAATACAATCGATTACACCGAAAATGCCG----G---GAGTTTTTCCATTTCCGCC  SEQ ID NO: 104
     1 | CTATGACGAAATTCATGAGGTTGCGCAAA-AATCGGGCAATACAATCGATTACACCGAAAATGCCG-------------------TTTCCGCC  SEQ ID NO: 105
     1 | CTATGACGAAATTCATGAGGTTGCGCAAAT-ATCGGGCAATACAATCGATTACACCGAAAATGCCG-------------------TTTCCGCC  SEQ ID NO: 106
wg   3 | CTATGACGAAATTCATGAGGTTGCGCAAA-AATCGGGCAATACAATCGATTACACCGAAAATG----------------------TTTCCGCC  SEQ ID NO: 107
     1 | CTATGACGAAATTCATGAGGTTGCGCAAAT-ATCGGGCAATACAATCGATTACACCGAAAATG----------------------TTTCCGCC  SEQ ID NO: 108
     1 | CTATGACGAAATTCATGAGGTTGCGCAAAT-ATCGGGCAATACAATCGATTACACCGAAAATGCCGTTTTTCCGGAGTTTTTCCATTTCCGCC  SEQ ID NO: 109
```

PAM sgRNA PAM sgRNA

*86Fa 1045D (hh+wg) - D2*

```
      WT | TCTGGTTGTCCCGCTTCCACTTCCCTTGCGCATAAGGCAGCATAAAAATGAACACCAC-------------AGCCGATCGAACGTCGAGTGGCATACGCACACAAT SEQ ID NO: 110
hh     5 | TCTGGTTGTCCCGCTTCCACTTCCCTTGCGCATAAGGCAGCATAAAAATGAACACCAC-------------AGCCGA-------TCGAGTGGCATACGCATACAAT SEQ ID NO: 111
       5 | TCTGGTTGTCCCGCTTCCACTTCCCTTGCGCATAAGGCAGCATAAAAATGAACACCACAGCCGAGTGGTCGAGCCGAGTGAACGTCGAGTGGCATACGCACACAAT SEQ ID NO: 112
         | CTATGACGAAATTCATGAGGTTGCGCAAATAATCGGGCAATACAATCGATTACACCGAAAATGCCGGGCAGAGTTTTTCCATTTCCGCCATTT  SEQ ID NO: 113
wg 12 WT | CTATGACGAAATTCATGAGGTTGCGCA-----------AATACAATCGATTACACCGAAAATGCCGGGC--AGTTTTTCCATTTCCGCCATTT  SEQ ID NO: 114
```

PAM sgRNA PAM sgRNA

FIG. 10 (Cont.)

SEQUENCE LISTING

<160> NUMBER OF SEQ ID NOS: 40

<210> SEQ ID NO 1
<211> LENGTH: 60
<212> TYPE: DNA
<213> ORGANISM: Artificial Sequence
<220> FEATURE:
<223> OTHER INFORMATION: Synthetic primer for attP sequence from plasmid M

<400> SEQUENCE: 1
cccacaatgg ttaattcgag ctcgcccggg tcctaggtcg acgatgtagg tcacggtctc 60

<210> SEQ ID NO 2
<211> LENGTH: 60
<212> TYPE: DNA
<213> ORGANISM: Artificial Sequence
<220> FEATURE:
<223> OTHER INFORMATION: Synthetic primer for attP sequence from plasmid M

<400> SEQUENCE: 2
gttattttaa aaacgattca ttctagttaa ttaagtcgac atgcccgccg tgaccgtcga 60

<210> SEQ ID NO 3
<211> LENGTH: 60
<212> TYPE: DNA
<213> ORGANISM: Artificial Sequence
<220> FEATURE:
<223> OTHER INFORMATION: Synthetic primer for p10 3'UTR from Addgene plasmid #100580

<400> SEQUENCE: 3
tcgacggtca cggcgggcat gtcgacttaa ttaactagaa tgaatcgttt ttaaaataac 60

<210> SEQ ID NO 4
<211> LENGTH: 60
<212> TYPE: DNA
<213> ORGANISM: Artificial Sequence
<220> FEATURE:
<223> OTHER INFORMATION: Synthetic primer for p10 3'UTR from Addgene plasmid #100580

<400> SEQUENCE: 4
aaaagttggt ggtggggagg ccaccgagta tgggcgcgcc ccggccgtta actcgaatcg 60

<210> SEQ ID NO 5
<211> LENGTH: 60
<212> TYPE: DNA
<213> ORGANISM: Artificial Sequence
<220> FEATURE:
<223> OTHER INFORMATION: Synthetic primer for opie2 promoter fragment from Translocation plasmid B

<400> SEQUENCE: 5
gctggcttgg atagcgattc gagttaacgg ccggggcgcg cccatactcg gtggcctccc 60

<210> SEQ ID NO 6
<211> LENGTH: 60
<212> TYPE: DNA
<213> ORGANISM: Artificial Sequence
<220> FEATURE:
<223> OTHER INFORMATION: Synthetic primer for opie2 promoter fragment from Translocation plasmid B

<400> SEQUENCE: 6
ccccggtgaa cagctcctcg cccttgctca ccatctcgag caccagagac aggttgcggc 60

<210> SEQ ID NO 7
<211> LENGTH: 60
<212> TYPE: DNA
<213> ORGANISM: Artificial Sequence
<220> FEATURE:
<223> OTHER INFORMATION: Synthetic primer for eCFP from
pJFRC81-10XUAS-IVS-Syn21-GFP-p10

<400> SEQUENCE: 7
cgccatccaa ccgccgccgc aacctgtctc tggtgctcga gatggtgagc aagggcgagg 60

<210> SEQ ID NO 8
<211> LENGTH: 60
<212> TYPE: DNA
<213> ORGANISM: Artificial Sequence
<220> FEATURE:
<223> OTHER INFORMATION: Synthetic primer for eCFP from
pJFRC81-10XUAS-IVS-Syn21-GFP-p10

<400> SEQUENCE: 8
gtggtatggc tgattatgat ctagagtcgc ggccgcttac ttgtacagct cgtccatgcc 60

<210> SEQ ID NO 9
<211> LENGTH: 60
<212> TYPE: DNA
<213> ORGANISM: Artificial Sequence
<220> FEATURE:
<223> OTHER INFORMATION: Synthetic primer for Ubiquitin-63E promoter
fragment (for 986B) from D. melanogaster genomic DNA

<400> SEQUENCE: 9
agcgggttct cgacggtcac ggcgggcatg tcgacgcggc cgccgcgcag atcgccgatg 60

<210> SEQ ID NO 10
<211> LENGTH: 60
<212> TYPE: DNA
<213> ORGANISM: Artificial Sequence
<220> FEATURE:
<223> OTHER INFORMATION: Synthetic primer for Ubiquitin-63E promoter
fragment (for 986B) from D. melanogaster genomic DNA

<400> SEQUENCE: 10
caatggagta cttcttgtcc atggtggcag tttaaactct gcgggtcaaa atagagatgt 60

<210> SEQ ID NO 11
<211> LENGTH: 60
<212> TYPE: DNA
<213> ORGANISM: Artificial Sequence
<220> FEATURE:
<223> OTHER INFORMATION: Synthetic primer for dCas9-VPR (for 986B) from
Addgene plasmid #78898

<400> SEQUENCE: 11
attttccaca tctctatttt gacccgcaga gtttaaactg ccaccatgga caagaagtac 60

<210> SEQ ID NO 12
<211> LENGTH: 60
<212> TYPE: DNA
<213> ORGANISM: Artificial Sequence
<220> FEATURE:
<223> OTHER INFORMATION: Synthetic primer for dCas9-VPR (for 986B) from
Addgene plasmid #78898

<400> SEQUENCE: 12
attgatttgt tattttaaaa acgattcatt ctagttaatt aatcaaaaca gagatgtgtc 60

<210> SEQ ID NO 13
<211> LENGTH: 60
<212> TYPE: DNA
<213> ORGANISM: Artificial Sequence
<220> FEATURE:
<223> OTHER INFORMATION: Synthetic primer for bottleneck promoter fragment (for 986C) from D. melanogaster genomic DNA

<400> SEQUENCE: 13
gcgggttctc gacggtcacg gcgggcatgt cgacgcggcc gcattagatg aaccccatgg 60

<210> SEQ ID NO 14
<211> LENGTH: 60
<212> TYPE: DNA
<213> ORGANISM: Artificial Sequence
<220> FEATURE:
<223> OTHER INFORMATION: Synthetic primer for bottleneck promoter fragment (for 986C) from D. melanogaster genomic DNA

<400> SEQUENCE: 14
cccaatggag tacttcttgt ccatggtggc agtttaaaca gccgaattcg ttgacggttg 60

<210> SEQ ID NO 15
<211> LENGTH: 60
<212> TYPE: DNA
<213> ORGANISM: Artificial Sequence
<220> FEATURE:
<223> OTHER INFORMATION: Synthetic primer for dCas9-VPR (for 986C) from Addgene plasmid #78898

<400> SEQUENCE: 15
ttcgtacttc aaccgtcaac gaattcggct gtttaaactg ccaccatgga caagaagtac 60

<210> SEQ ID NO 16
<211> LENGTH: 60
<212> TYPE: DNA
<213> ORGANISM: Artificial Sequence
<220> FEATURE:
<223> OTHER INFORMATION: Synthetic primer for dCas9-VPR (for 986C) from Addgene plasmid #78898

<400> SEQUENCE: 16
attgatttgt tattttaaaa acgattcatt ctagttaatt aatcaaaaca gagatgtgtc 60

<210> SEQ ID NO 17
<211> LENGTH: 60
<212> TYPE: DNA
<213> ORGANISM: Artificial Sequence
<220> FEATURE:
<223> OTHER INFORMATION: Synthetic primer for Ubiquitin-63E promoter fragment (for 986D) from D. melanogaster genomic DNA

<400> SEQUENCE: 17
agcgggttct cgacggtcac ggcgggcatg tcgacgcggc cgccgcgcag atcgccgatg 60

<210> SEQ ID NO 18
<211> LENGTH: 60
<212> TYPE: DNA
<213> ORGANISM: Artificial Sequence
<220> FEATURE:
<223> OTHER INFORMATION: Synthetic primer for Ubiquitin-63E promoter fragment (for 986D) from D. melanogaster genomic DNA

<400> SEQUENCE: 18
tcgtggccgc cggccttttc atggtggcag tttaaactct gcgggtcaaa atagagatgt 60

<210> SEQ ID NO 19
<211> LENGTH: 60
<212> TYPE: DNA
<213> ORGANISM: Artificial Sequence
<220> FEATURE:
<223> OTHER INFORMATION: Synthetic primer for dCas9-VP64 (for 986D) from Addgene plasmid #78897

<400> SEQUENCE: 19
ttccacatct ctattttgac ccgcagagtt taaactgcca ccatgaaaag gccggcggcc 60

<210> SEQ ID NO 20
<211> LENGTH: 60
<212> TYPE: DNA
<213> ORGANISM: Artificial Sequence
<220> FEATURE:
<223> OTHER INFORMATION: Synthetic primer for dCas9-VP64 (for 986D) from Addgene plasmid #78897

<400> SEQUENCE: 20
attgatttgt tattttaaaa acgattcatt ctagttaatt aattagccct cccacacata 60

<210> SEQ ID NO 21
<211> LENGTH: 60
<212> TYPE: DNA
<213> ORGANISM: Artificial Sequence
<220> FEATURE:
<223> OTHER INFORMATION: Synthetic primer for bottleneck promoter fragment (for 986E) from D. melanogaster genomic DNA

<400> SEQUENCE: 21
gcgggttctc gacggtcacg gcgggcatgt cgacgcggcc gcattagatg aaccccatgg 60

<210> SEQ ID NO 22
<211> LENGTH: 60
<212> TYPE: DNA
<213> ORGANISM: Artificial Sequence
<220> FEATURE:
<223> OTHER INFORMATION: Synthetic primer for bottleneck promoter fragment (for 986E) from D. melanogaster genomic DNA

<400> SEQUENCE: 22
tttcgtggcc gccggccttt tcatggtggc agtttaaaca gccgaattcg ttgacggttg 60

<210> SEQ ID NO 23
<211> LENGTH: 60
<212> TYPE: DNA
<213> ORGANISM: Artificial Sequence
<220> FEATURE:
<223> OTHER INFORMATION: Synthetic primer for dCas9-VP64 (for 986E) from Addgene plasmid #78897

<400> SEQUENCE: 23
gtacttcaac cgtcaacgaa ttcggctgtt taaactgcca ccatgaaaag gccggcggcc 60

<210> SEQ ID NO 24
<211> LENGTH: 60
<212> TYPE: DNA
<213> ORGANISM: Artificial Sequence
<220> FEATURE:
<223> OTHER INFORMATION: Synthetic primer for dCas9-VP64 (for 986E) from Addgene plasmid #78897

<400> SEQUENCE: 24
attgatttgt tattttaaaa acgattcatt ctagttaatt aatcaaaaca gagatgtgtc 60

<210> SEQ ID NO 25
<211> LENGTH: 60
<212> TYPE: DNA
<213> ORGANISM: Artificial Sequence
<220> FEATURE:
<223> OTHER INFORMATION: Synthetic primer for U6:3 promoter fragment from Addgene plasmid #49411

<400> SEQUENCE: 25
ttgggaattg ggcaatattt aaatggcggc gcgccgaatt ctttttttgct cacctgtgat 60

<210> SEQ ID NO 26
<211> LENGTH: 60
<212> TYPE: DNA
<213> ORGANISM: Artificial Sequence
<220> FEATURE:
<223> OTHER INFORMATION: Synthetic primer for U6:3 promoter fragment from Addgene plasmid #49411

<400> SEQUENCE: 26
cttattttaa cttgctattt ctagctctaa aaccctaggc cgacgttaaa ttgaaaatag 60

<210> SEQ ID NO 27
<211> LENGTH: 60
<212> TYPE: DNA
<213> ORGANISM: Artificial Sequence
<220> FEATURE:
<223> OTHER INFORMATION: Synthetic primer for sgRNA scaffold from Addgene plasmid #49411

<400> SEQUENCE: 27
atatatagac ctattttcaa tttaacgtcg gcctagggtt ttagagctag aaatagcaag 60

<210> SEQ ID NO 28
<211> LENGTH: 60
<212> TYPE: DNA
<213> ORGANISM: Artificial Sequence
<220> FEATURE:
<223> OTHER INFORMATION: Synthetic primer for sgRNA scaffold from Addgene plasmid #49411

<400> SEQUENCE: 28
agtggatctc tagaggtacc gttgcggccg cgttttaatt aaaaaagcac cgactcggtg 60

<210> SEQ ID NO 29
<211> LENGTH: 55
<212> TYPE: DNA
<213> ORGANISM: Artificial Sequence
<220> FEATURE:
<223> OTHER INFORMATION: Synthetic primer for eve-sgRNA-U6:1-promoter-hid-sgRNA fragment from Custom gBlocks Gene Fragment

<400> SEQUENCE: 29
gttcgtatat atagacctat tttcaattta acgtcggatc gtgcggtgct gagag 55

<210> SEQ ID NO 30
<211> LENGTH: 60
<212> TYPE: DNA
<213> ORGANISM: Artificial Sequence
<220> FEATURE:
<223> OTHER INFORMATION: Synthetic primer for eve-sgRNA-U6:1-promoter-hid-sgRNA fragment from Custom gBlocks Gene Fragment

<400> SEQUENCE: 30
cggactagcc ttattttaac ttgctatttc tagctctaaa actcatgcac gtgcatgtgc 60

<210> SEQ ID NO 31
<211> LENGTH: 60
<212> TYPE: DNA
<213> ORGANISM: Artificial Sequence
<220> FEATURE:
<223> OTHER INFORMATION: Synthetic primer for
Gypsy-U6:1-promoter-hh1-sgRNA-U6:3-promoter-hh2-sgRNA fragment
(for OA-1045B) from pCFD-hh

<400> SEQUENCE: 31
ggtgcttttt taattaaaac gcggccgcaa cggtacctgc agccacgtaa taagtgtgcg 60

<210> SEQ ID NO 32
<211> LENGTH: 60
<212> TYPE: DNA
<213> ORGANISM: Artificial Sequence
<220> FEATURE:
<223> OTHER INFORMATION: Synthetic primer for
Gypsy-U6:1-promoter-hh1-sgRNA-U6:3-promoter-hh2-sgRNA fragment
(for OA-1045B) from pCFD-hh

<400> SEQUENCE: 32
acactagtgg atctctagaa caactctcag gctccaggta ggcaaaaaag caccgactcg 60

<210> SEQ ID NO 33
<211> LENGTH: 60
<212> TYPE: DNA
<213> ORGANISM: Artificial Sequence
<220> FEATURE:
<223> OTHER INFORMATION: Synthetic primer for
Gypsy-U6:1-promoter-wg1-sgRNA-U6:3-promoter-wg2-sgRNA fragment
(for OA-1045C) from pCFD-wg

<400> SEQUENCE: 33
ggtgcttttt taattaaaac gcggccgcaa cggtacctgc agccacgtaa taagtgtgcg 60

<210> SEQ ID NO 34
<211> LENGTH: 60
<212> TYPE: DNA
<213> ORGANISM: Artificial Sequence
<220> FEATURE:
<223> OTHER INFORMATION: Synthetic primer for
Gypsy-U6:1-promoter-wg1-sgRNA-U6:3-promoter-wg2-sgRNA fragment
(for OA-1045C) from pCFD-wg

<400> SEQUENCE: 34
acactagtgg atctctagaa caactctcag gctccaggta ggcaaaaaag caccgactcg 60

<210> SEQ ID NO 35
<211> LENGTH: 60
<212> TYPE: DNA
<213> ORGANISM: Artificial Sequence
<220> FEATURE:
<223> OTHER INFORMATION: Synthetic primer for
U6:1-promoter-wg1-sgRNA-U6:3-promoter-wg2-sgRNA fragment (for
OA-1045D) from pCFD-wg

<400> SEQUENCE: 35
ccgggaattg ggaattgggc aatatttaaa tggcggcgcg ccagccgatc aattgagatc 60

<210> SEQ ID NO 36
<211> LENGTH: 60
<212> TYPE: DNA
<213> ORGANISM: Artificial Sequence
<220> FEATURE:
<223> OTHER INFORMATION: Synthetic primer for
U6:1-promoter-wg1-sgRNA-U6:3-promoter-wg2-sgRNA fragment (for OA-1045D) from pCFD-wg

<400> SEQUENCE: 36
tgtttttgcg aataaattca acgcacactt attacgtgca tatgaacaac tctcaggctc 60

<210> SEQ ID NO 37
<211> LENGTH: 45
<212> TYPE: DNA
<213> ORGANISM: Artificial Sequence
<220> FEATURE:
<223> OTHER INFORMATION: Synthetic primer for
Gypsy-U6:1-promoter-hh1-sgRNA-U6:3-promoter-hh2-sgRNA fragment
(for OA-1045D) from pCFD-hh

<400> SEQUENCE: 37
ctggagcctg agagttgttc atatgcacgt aataagtgtg cgttg 45

<210> SEQ ID NO 38
<211> LENGTH: 60
<212> TYPE: DNA
<213> ORGANISM: Artificial Sequence
<220> FEATURE:
<223> OTHER INFORMATION: Synthetic primer for
Gypsy-U6:1-promoter-hh1-sgRNA-U6:3-promoter-hh2-sgRNA fragment
(for OA-1045D) from pCFD-hh

<400> SEQUENCE: 38
tttattgaac aactctcagg ctccaggtag tctagagcaa aaaagcaccg actcggtgcc 60

<210> SEQ ID NO 39
<211> LENGTH: 60
<212> TYPE: DNA
<213> ORGANISM: Artificial Sequence
<220> FEATURE:
<223> OTHER INFORMATION: Synthetic primer for
tRNA-eve-sgRNA-tRNA-hid-sgRNA-tRNA-hh1-sgRNA-tRNA-hh2-sgRNA-U6:3
UTR fragment (for OA-1045E) from Gene synthesized vector

<400> SEQUENCE: 39
tcgtatatat agacctattt tcaatttaac gtcggttaat taagggcttt gagtgtgtgt 60

<210> SEQ ID NO 40
<211> LENGTH: 60
<212> TYPE: DNA
<213> ORGANISM: Artificial Sequence
<220> FEATURE:
<223> OTHER INFORMATION: Synthetic primer for
tRNA-eve-sgRNA-tRNA-hid-sgRNA-tRNA-hh1-sgRNA-tRNA-hh2-sgRNA-U6:3
UTR fragment (for OA-1045E) from Gene synthesized vector

<400> SEQUENCE: 40
tcgtcgacac tagtggatct ctagaggtac cgttgcggcc gcatgcatac gcattaagcg 60

ENGINEERED REPRODUCTIVE ISOLATION IN ANIMALS

CROSS-REFERENCE TO RELATED APPLICATIONS

This application is a National Stage Application under 35 U.S.C. § 371 and claims the benefit of International Application No. PCT/US2021/038595, filed Jun. 23, 2021, which claims priority to U.S. Application Ser. No. 63/042,614, filed on Jun. 23, 2020. The disclosure of the prior application is considered part of the disclosure of this application, and is incorporated in its entirety into this application.

SEQUENCE LISTING

This application contains a Sequence Listing that has been submitted electronically as an ASCII text file named Sequence_Listing.txt. The ASCII text file, created on Dec. 19, 2022, is 11,045 bytes in size. The material in the ASCII text file is hereby incorporated by reference in its entirety.

BACKGROUND

Exploiting post zygotic barriers between otherwise reproductively compatible organisms to ensure reproductive isolation has practical applications to both basic and applied research. It can be utilized to study natural speciation processes (Moreno *PLoS One.* 7, e39054 (2012)) and is a useful research tool. These barriers can also block gene flow from engineered organisms, such as agricultural plants, to wild varieties by preventing the development of viable hybrid zygotes (Maselko et al., *Nat. Commun.,* 8:883 (2017); Burgos et al., *Plant Physiol.,* 166:1208-1220 (2014)).

SUMMARY

This disclosure provides methods and materials for engineering reproductive isolation in an animal.

In one aspect, this disclosure a method of engineering a reproductive barrier in an insect including: (a) introducing into a first insect a first nucleic acid sequence, where the first nucleic acid sequence targets a genomic sequence, where the genomic sequence is proximal to a transcription start site of a gene product; and (b) introducing into a second insect a second nucleic acid sequence encoding a nuclease-deficient endonuclease; and (c) genetically crossing the first insect with the second insect, where the second insect includes a second copy of the genomic sequence where the second copy of the genomic sequence is proximal to a transcription start site of a second copy of the gene product, where the first nucleic acid sequence targets the genomic sequence and/or the second copy of the genomic sequence, and where in the progeny of the genetic cross between the first insect and the second insect the nuclease-deficient endonuclease binds to the genomic sequence and/or the second copy of the genomic sequence, thereby promoting expression of the (i) gene product and/or (ii) the second copy of the gene product. In some embodiments, the nuclease-deficient endonuclease interacts with the genomic sequence and/or the second copy of the genomic sequence via the first nucleic acid sequence. In some embodiments, step (a) includes integrating the first nucleic acid sequence into the genome of the first insect. In some embodiments, step (b) includes integrating the second nucleic acid sequence into the genome of the second insect.

In some embodiments, the genomic sequence includes a regulatory element. In some embodiments, the regulatory element at least partially controls expression of the gene product. In some embodiments, the regulatory element includes a promoter, an enhancer, a silencer, an insulator, a locus control region, or a synthetic promoter. In some embodiments, the regulatory element is a promoter. In some embodiments, expression of the gene product is lethal when misexpressed as compared to native expression.

In some embodiments, the first nucleic acid sequence includes a guide RNA targeting (i) the genomic sequence and/or (ii) the second copy of the genomic sequence. In some embodiments, the nuclease-deficient endonuclease includes a CRISPR-associated sequence 9 (Cas9) endonuclease or a variant thereof, a CRISPR-associated sequence 13 (Cas13) endonuclease or a variant thereof, a CRISPR from *Prevotella* and *Francisella* 1 (Cpf1) endonuclease or a variant thereof, a CRISPR from Microgenomates and *Smithella* 1 (Cms1) endonuclease or a variant thereof, or a CRISPR-associated sequence 6 (Cas6) endonuclease or a variant thereof. In some embodiments, the nuclease-deficient endonuclease includes a *Streptococcus pyogenes* Cas9 (SpCas9), a *Staphylococcus aureus* Cas9 (SaCas9), a *Francisella novicida* Cas9 (FnCas9), or a variant thereof. In some embodiments, the variant thereof includes a protospacer adjacent motif (PAM) SpCas9 (xCas9), high fidelity SpCas9 (SpCas9-FIF1), a high fidelity SaCas9, or a high fidelity FnCas9. In some embodiments, the nuclease-deficient endonuclease includes a Cas fusion nuclease including a Cas9 protein or a variant thereof fused with a FokI nuclease or variant thereof. In some embodiments, the nuclease-deficient endonuclease includes a CRISPR-associated sequence 9 (Cas9) endonuclease or a variant thereof. In some embodiments, nuclease-deficient Cas9 includes a first amino acid substitution of D10A and a second amino acid substitution of H840A.

In some embodiments, the nuclease-deficient endonuclease is fused to one or more effector domains. In some embodiments, the one or more effector domains including at least one of an activator domain, a repressor domain, a recruitment domain, a transcription factor, or a chromatin modifier. In some embodiments, the one or more effector domains including at least one of a SunTag, a SAM, a VPR, or a VP64. In some embodiments, the effector domain is VP64. In some embodiments, the effector domain is VPR.

In some embodiments, the first nucleic acid sequence includes one or more RNA hairpins, where the RNA hairpins bind one or more RNA binding proteins fused to one or more effector domains. In some embodiments, the one or more effector domains including at least one of an activator domain, a repressor domain, a recruitment domain, a transcription factor, or a chromatin modifier. In some embodiments, the one or more effector domains including at least one of a SunTag, a SAM, a VPR, or a VP64. In some embodiments, the effector domain is VP64. In some embodiments, the effector domain is VPR.

In some embodiments, step (a) further includes introducing into the first insect an endonuclease, where the endonuclease cleaves the genomic sequence, thereby creating a mutation in the genomic sequence. In some embodiments, the endonuclease includes a CRISPR-associated sequence 9 (Cas9) endonuclease or a variant thereof, a CRISPR-associated sequence 13 (Cas13) endonuclease or a variant thereof, a CRISPR from *Prevotella* and *Francisella* 1 (Cpf1) endonuclease or a variant thereof, a CRISPR from Microgenomates and *Smithella* 1 (Cms1) endonuclease or a variant thereof, or a CRISPR-associated sequence 6 (Cas6) endonuclease or a variant thereof. In some embodiments, the endonuclease includes a *Streptococcus pyogenes* Cas9 (SpCas9), a *Staphylococcus aureus* Cas9 (SaCas9), a *Francisella novicida* Cas9 (FnCas9), or a variant thereof. In some embodiments, the variant thereof includes a protospacer adjacent motif (PAM) SpCas9 (xCas9), high fidelity SpCas9 (SpCas9-FIF1), a high fidelity SaCas9, or a high fidelity FnCas9. In some embodiments, the mutation prevents the first nucleic acid sequence from targeting the genomic sequence. In some embodiments, the mutation includes an insertion or a deletion. In some embodiments, the mutation occurs within the first 10 nucleotides of a PAM sequence associated with the first nucleic acid sequence. In some embodiments, step (b) includes transiently introducing the endonuclease. In some embodiments, step (b) includes introducing mRNA encoding the endonuclease. In some embodiments, the mutation in the genomic sequence does not alter expression of the gene product. In some embodiments, the gene product including at least one of even skipped (eve), head involution defective (hid), hedgehog (hh), or wingless (wg), or a combination thereof.

In some embodiments, the first nucleic acid sequences includes a first gRNA and a second gRNA, where the first gRNA targets a first genomic sequence and the second gRNA targets a second genomic sequence. In some embodiments, the first nucleic acid sequence includes a first gRNA, a second gRNA, and a third gRNA, where the first gRNA targets a first genomic sequence, the second gRNA targets a second genomic sequence, and the third gRNA targets a third genomic sequence, where each genomic sequence is proximal to a transcription start site of a gene product. In some embodiments, the combination of gene products including at least one of: (i) eve and hid; (ii) eve, hid, and hh; (iii) eve, hid, and wg; or (iv) hh and wg. In some embodiments, the first insect is a mosquito from the genera *Stegomyia, Aedes, Anopheles*, or *Culex* and the second insect is a mosquito from the genera *Stegomyia, Aedes, Anopheles*, or *Culex*. In some embodiments, where the first mosquito and/or the second mosquito include *Aedes aegypti, Aedes albopictus, Ochlerotatus triseriatus* (*Aedes triseriatus*), *Anopheles stephensi, Anopheles albimanus, Anopheles gambiae, Anopheles quadrimaculatus, Anopheles freebori, Culex species*, or *Culiseta melanura*. In some embodiments, the insect includes a tephritid fruit fly selected from Medfly (*Ceratitis capitata*), Mexfly (*Anastrepha ludens*), Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*), Caribbean fruit fly (*Anastrepha suspensa*), Oriental Fruit Fly (*Bactrocera dorsalis*), West Indian fruit fly (*Anastrepha obliqua*), the New World screwworm (*Cochliomyia hominivorax*), the Old World screwworm (*Chrysomya bezziana*), Australian sheep blowfly/greenbottle fly (*Lucilia cuprina*), the pink bollworm (*Pectinophora gossypiella*), the European Gypsy moth (*Lymantria dispar*), the Navel Orange Worm (*Amyelois transitella*), the Peach Twig Borer (*Anarsia lineatella*), the rice stem borer (*Tryporyza incertulas*), the noctuid moths, Heliothinae, the Japanese beetle (Papilla *japonica*), White-fringed beetle (*Graphognatus* spp.), Boll weevil (*Anthonomous grandis*), the Colorado potato beetle (*Leptinotarsa decern lineata*), the vine mealybug (*Planococcus ficus*), Asian citrus psyllid (*Diaphorina citri*), Spotted wing *drosophila* (*Drosophila suzukii*), Bluegreen sharpshooter (*Graphocephala atropunctata*), Glassy winged sharpshooter (*Flomalodisca vitripennis*), Light brown apple moth (*Epiphyas postvittana*), *Bagrada* bug (*Bagrada hilaris*), Brown marmorated stink bug (*Halyomorpha halys*), Asian Gypsy Moth selected from the group of *Lymantria dispar asiatica, Lymantria dispar japonica, Lymantria albescens, Lymantria umbrosa*, and *Lymantria postalba*, Asian longhomed beetle (*Anoplophora glabripennis*), Coconut Rhinoceros Beetle (*Oryctes rhinoceros*), Emerald Ash Borer (*Agrilus planipennis*), European Grapevine Moth (*lobesia botrana*), European Gypsy Moth (*Lymantria dispar*), False Codling Moth (*Thaumatotibia leucotreta*), fire ants selected from *Solenopsis invicta* Buren, and *S. richteri* Forel, Old World Bollworm (*Flelicoverpa armigera*), Spotted Lanternfly (*Lycorma delicatula*), Africanized honeybee (*Apis mellifera scutellata*), Fruit and shoot borer (*Leucinodes orbonalis*), corn root worm (*Diabrotica* spp.), Western corn rootworm (*Diabrotica virgifera*), Whitefly (*Bemisia tabaci*), Flouse Fly (*Musca domestica*), Green Bottle Fly (*Lucilia cuprina*), Silk Moth (*Bombyx mori*), Red Scale (*Aonidiella aurantia*), Dog heartworm (*Dirofilaria immitis*), Southern pine beetle (*Dendroctonus frontalis*), Avocado thrip (*Thysanoptera* Spp.), Botfly selected from *Oestridae* spp. and *Dermatobia hominis*), Florse Fly (*Tabanus sulcifrons*), Florn Fly (*Flaematobia irritans*), Screwworm Fly selected from *Cochliomyia macellaria* (*C. macellaria*), *C. hominivorax, C. aldrichi*, or *C. minima*, Tsetse Fly (*Glossina* spp.), Warble Fly selected from *Flypoderma bovis* or *Hypoderma lineatum*, Spotted lanternfly (*Lycorma delicatula*), Khapra beetle (*Trogoderma granarium*), Honeybee mite (*Varroa destructor*), Termites (*Coptotermes formosanus*), Hemlock woolly adelgid (*Adelges tsugae*), Walnut twig beetle (*Pityophthorus juglandis*), European wood wasp (*Sirex noctilio*), Pink-spotted bollworm (*Pectinophora scutigera*), Two spotted spider mite (*Tertanychus urticae*), Diamondback moth (*Plutella xylostella*), Taro caterpillar (*Spodoptera litura*), Red flour beetle (*Tribolium castaneum*), Green peach aphid (*Myzus persicae*), Cotton Aphid (*Aphis gossypii*), Brown planthopper (*Nilaparvata lugens*), Beet armyworm (*Spodotera exigua*), Western flower *Thrips* (*Frankliniella occidentalis*), Codling moth (*Cydia pomonella*), Cowpea weevil (*Callosobruchus maculatus*), Pea aphid (*Acyrthosiphon pisum*), Tomato leafminer (*Tuta absoluta*), Onion *Thrips* (*Thrips tabaci*), and Cotton bollworm (*Helicoverpa armigera*).

In another aspect, this disclosure features a method of engineering a reproductive barrier in an insect including: (a) introducing into a first insect a first nucleic acid sequence, where the first nucleic acid sequence targets a genomic sequence that is proximal to a transcription start site of a gene product; and an endonuclease, where the endonuclease cleaves the genomic sequence, thereby creating a mutation in the genomic sequence; and (b) introducing into a second insect a second nucleic acid sequence encoding a nuclease-deficient endonuclease; and (c) genetically crossing the first insect with the second insect, where the second insect includes a second copy of the genomic sequence, that is proximal to a transcription start site of a second copy of the gene product, where the first nucleic acid sequence targets the second copy of the genomic sequence, and where in the progeny of the genetic cross between the first insect and the second insect the nuclease-deficient endonuclease binds to the second copy of the genomic sequence, thereby promoting expression of the second copy of the gene product.

In another aspect, this disclosure features a genetically modified insect produced by the method of any of the method described herein.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1A shows homozygous dCas9-VPR individuals were crossed bidirectionally to homozygous sgRNA individuals. The dCas9-VPR complex bound to its targeted site and the VPR activator domain upregulated transcription, resulting in postzygotic lethality due to endogenous gene misexpression. Shaded grey background indicates expected lethal crosses. FIG. 1B shows homozygous dCas9-VPR individuals were crossed bidirectionally to heterozygous spCas9/sgRNA individuals. When spCas9/sgRNA males were crossed to dCas9-VPR females, the resulting heterozygous dCas9/+;sgRNA/+ progeny also experienced endogenous gene misexpression due to the VPR activator domain and thus did not survive past L1. However, dCas9-VPR males crossed to spCas9/sgRNA females were viable due to the maternal deposition of Cas9 in dCas9/+;sgRNA/+ heterozygous progeny, which resulted in embryonic disruption of the sgRNA target site, forcing a bottleneck in dCas9/+; sgRNA/+ heterozygous progeny to inherit protective mutations or perish. These surviving individuals were repeatedly inbred to generate SPECIES. FIGS. 1C-1D show plots depicting % progeny survival from the crosses depicted in A and B. The chromosomes and genotypes above and to the left of the plots indicate the parents and the chromosomes and genotypes below the plots indicate their resulting progeny. All crosses were performed in triplicate. Horizontal bars indicate the mean.

FIG. 2A shows crosses to determine embryo and adult viability. (Cross #1) Homozygous dCas9-VPR;sgRNA "SPECIES" females crossed to homozygous dCas9-VPR; sgRNA SPECIES males. (Cross #2) Homozygous dCas9-VPR;sgRNA SPECIES females crossed to wildtype (WT) males. (Cross #3) WT females crossed to homozygous dCas9-VPR;sgRNA SPECIES males. Gray shaded background indicates expected lethal crosses. (Cross #4) WT females crossed to WT males. Each cross type was performed for all eight generated SPECIES (FIG. 9). FIG. 2B shows a schematic detailing the methods of determining embryo and adult survival compared to WT. FIG. 2C shows graphs where % embryo and adult survival was calculated and plotted. The number below each x-axis group indicates cross number (#1-4). N=3 biologically independent replicates for each cross number. † indicates that embryos did not survive past L1/L2 stages. Unpaired two-tailed t-tests were performed for each SPECIES compared to WT (*$p<0.05$, $p<0.01$, *$p<0.001$, and ****$p<0.0001$). Middle lines indicate mean, while error bars represent standard deviation. The color of the dots represent each species as indicated in figure key. FIG. 2D shows embryo (left graph) and adult (right graph) Cohen's d effect sizes compared to WT. N=6 observations per cross number per SPECIES (effect size based on mean comparison between three replicates of each experimental cross (#1-3) to control cross (#4)). Error bars represent 95% confidence interval. The color of the dots represent each species as indicated in figure key.

FIG. 3A shows a schematic demonstrating reproductive barriers. The homozygous progeny of intercrossed SPECIES contain two copies of protected indel mutations, preventing lethal overexpression. The heterozygous progeny of SPECIES outcrossed to WT inherit only one copy of the protected indel mutations, which cannot prevent lethal overexpression of the target genes. Gray shaded background indicates expected lethality. FIG. 3B shows antibody stains for Eve and Runt in stage-13 embryos. DAPI stains all nuclei. Top row shows A1×A1. Bottom row shows A1×WT SPECIES outcross and Eve overexpression. FIG. 3C shows cuticle preparations showing denticle belts in self cross vs. outcross. Representative embryos and larval cuticles shown in FIGS. 3B-3C. Separate crosses produced animals with similar expression patterns and phenotypes (two crosses per genotype, N>30 embryos or larval cuticles examined per cross). FIG. 3D shows normalized embryo RNA-seq data (transcripts per kilobase million, TPM) for each species either self-crossed (open circles) or outcrossed to WT (closed circles), indicating expected target gene overexpression.

FIG. 5A shows a discrete generation model of a SPECIES-like extreme underdominant system with a fitness cost of 10% released at population frequencies of 45-60%. A release threshold is apparent between 50 and 55% (simulations confirm a threshold of 52.8%). FIG. 5B shows that the release threshold increases with fitness cost, from 50% for no fitness cost, to 83.3% for an 80% fitness cost. FIG. 5C shows that extreme underdominant systems spread quickly, reaching a population frequency of 99% (including heterozygotes and homozygotes) within 3-4 generations of a release at a frequency of 65% for fitness costs between 0 and 20%. FIG. 5D shows a discrete generation model of reciprocal chromosomal translocations with a fitness cost of 10% released at population frequencies of 50-65%. A release threshold is apparent between 55 and 60% (simulations confirm a threshold of 56.1%). FIG. 5E shows the release threshold increases with fitness cost, from 50% for no fitness cost, to 62.4% for a 20% fitness cost. Translocations cannot spread for fitness costs greater than 66.3%. FIG. 5F shows translocations spread less quickly, reaching a population frequency of 99% (including heterozygotes and homozygotes) within 7-13 generations of a release at a frequency of 65% for fitness costs between 0 and 20%. FIG. 5G shows discrete generation model of two-locus engineered underdominance with a fitness cost of 10% released at population frequencies of 25-40%. A release threshold is apparent between 30 and 35% (simulations confirm a threshold of 31.2%). FIG. 5H shows that the release threshold increases with fitness cost, from 26.9% for no fitness cost, to 35.9% for a 20% fitness cost. Two-locus engineered underdominance cannot spread for fitness costs greater than 72.7%. FIG. 5I shows two-locus engineered underdominant systems spread slightly less quickly, reaching a population frequency of 99% (including heterozygotes and homozygotes) within 4-5 generations of a release at a frequency of 65% for fitness costs between 0 and 20%.

FIG. 6A shows discrete generation model of a SPECIES-like extreme underdominant system released at 60% in population A and initially absent from population B. Population A exchanges migrants with population B at a rate of 1% per individual per generation. For a fitness cost of 10%, the system reaches near-fixation in population A within seven generations but only spreads to 0.01% in population B. FIG. 6B shows as the migration rate increases, the SPECIES system reaches a higher frequency in population B, exceeding 4%; however, for migration rates above 16.6% per individual per generation, it is eliminated from both populations through dilution of population A with wild types from population B. FIG. 6C shows for the two-population model, there is a migration threshold below which the construct fixes in population A and persists at a low level in population B and above which it is lost in both populations. For the source model, extreme underdominance displays threshold behavior with respect to migration rate. FIG. 6D shows discrete generation model of reciprocal chromosomal translocations released at 60% in population A and initially absent from population B. Population A exchanges migrants with population B at a rate of 1% per individual per generation. For a fitness cost of 10%, the system reaches near-fixation in population A within 22 generations and spreads to 3.6% in population B. FIG. 6E shows as the migration rate increases, the translocations reach a higher frequency in population B, exceeding 15%; however, for migration rates above 5.0% per individual per generation, they are eliminated from both populations through dilution of population A with wild types from population B. FIG. 6F shows for the two-population model, there is a migration threshold below which translocations fix in population A and persist at a low level in population B, and above which they are lost in both populations. For the source model, translocations display threshold behavior with respect to migration rate. FIG. 6G shows discrete generation model of two-locus engineered underdominance released at 60% in population A and initially absent from population B. Population A exchanges migrants with population B at a rate of 1% per individual per generation. For a fitness cost of 10%, the system reaches near-fixation in population A within eight generations and spreads to 3.2% in population B. FIG. 6H shows as the migration rate increases, the system reaches a higher frequency in population B, exceeding 21.2%; however, for migration rates above 4.2% per individual per generation, the system becomes fixed in both populations. FIG. 6I shows two-locus engineered underdominance displays threshold behavior with respect to migration rate.

FIG. 7 shows the constructs used in this study. A list of constructs used in this study, providing the construct ID, construct schematics, chromosomal insertion sites, Addgene ID number, Bloomington Stock number and citation.

(FIG. 8A) Complete lethality (100%) was observed in transheterozygotes (dCas9/+; sgRNA/+) when an sgRNA was crossed to dCas9-VPR due to lethal overexpression (Step 1). To generate protective indels, the sgRNA was first crossed to Cas9, then transheterozygous (Cas9/+; sgRNA/+) females were crossed to dCas9-VPR males generating a bottleneck by which a small proportion of transheterozygotes (dCas9/+; sgRNA/+) survived due to protective indels generated by Cas9/sgRNA (Step 2). Surviving individuals (inheriting Cas9 protein maternally but lacking Cas9 as a gene) were inbred for many generations (>5) to generate homozygous stocks (Step 3). To assess lethality and speciation, homozygous stocks were bidirectionally outcrossed to WT. For a single sgRNA system, complete synthetic lethality and speciation was not observed due to the fact that one WT copy of the target promoter was not sufficient to induce lethal overexpression (FIG. 8A, Step 4). To overcome this issue, either two sgRNAs (FIG. 8B), or three sgRNAs (FIG. 8C) were used to multiplex, and steps 1-4 were repeated to engineer reproductively isolated synthetic species.

FIG. 9 shows generation of eight SPECIES. For each synthetic species (A1, A2, B1, B2, C1, C2, D1, D2) the transgene ID, and chromosomal insertion site are listed.

FIG. 10 shows molecular characterization of protective indel mutations. For the generation of each independent synthetic species (A1, A2, B1, B2, C1, C2, D1, D2) the gRNA target site was sanger sequenced and the indels were confirmed. Number to the left of each sequence indicates the number of individuals sequenced with this mutation.

FIG. 11A shows individuals from each SPECIES were crossed to one another to determine the extent of reproductive isolation between SPECIES. FIG. 11B shows a graph where the total # of embryos laid is plotted in grey as bars on the left y-axis, while the total # of embryos surviving to adults is plotted on the right y-axis as points. N=3 biologically independent replicates of all eight SPECIES bidirectionally crossed to the remaining seven species. For embryos laid, each bar represents the mean. For embryos surviving to adults, middle lines indicate mean, while error bars represent standard deviation.

(FIG. 12A) Deseq comparisons between RNAseq samples WT×A1 (sample 8), WT×A2 (sample 9), A1×A1 (sample 10), A2×A2 (sample 11) observing target/non-target gene misexpression. (FIG. 12B) Deseq comparisons between RNAseq samples WT×B1 (sample 10), WT×B2 (sample 20), B1×B1 (sample 16) and B2×B2 (sample 22). (FIG. 12C) Deseq comparisons between RNAseq samples WT×C1 (sample 11), WT×C2 (sample 21), C1×C1 (sample 17), and C2×C2 (sample 23). (FIG. 12D) Deseq comparisons between RNAseq samples WT×D1 (sample 12), WT×D2 (sample 13), D1×D1 (sample 18), and D2×D2 (sample 19).

DETAILED DESCRIPTION

Figures 1A, 1B:
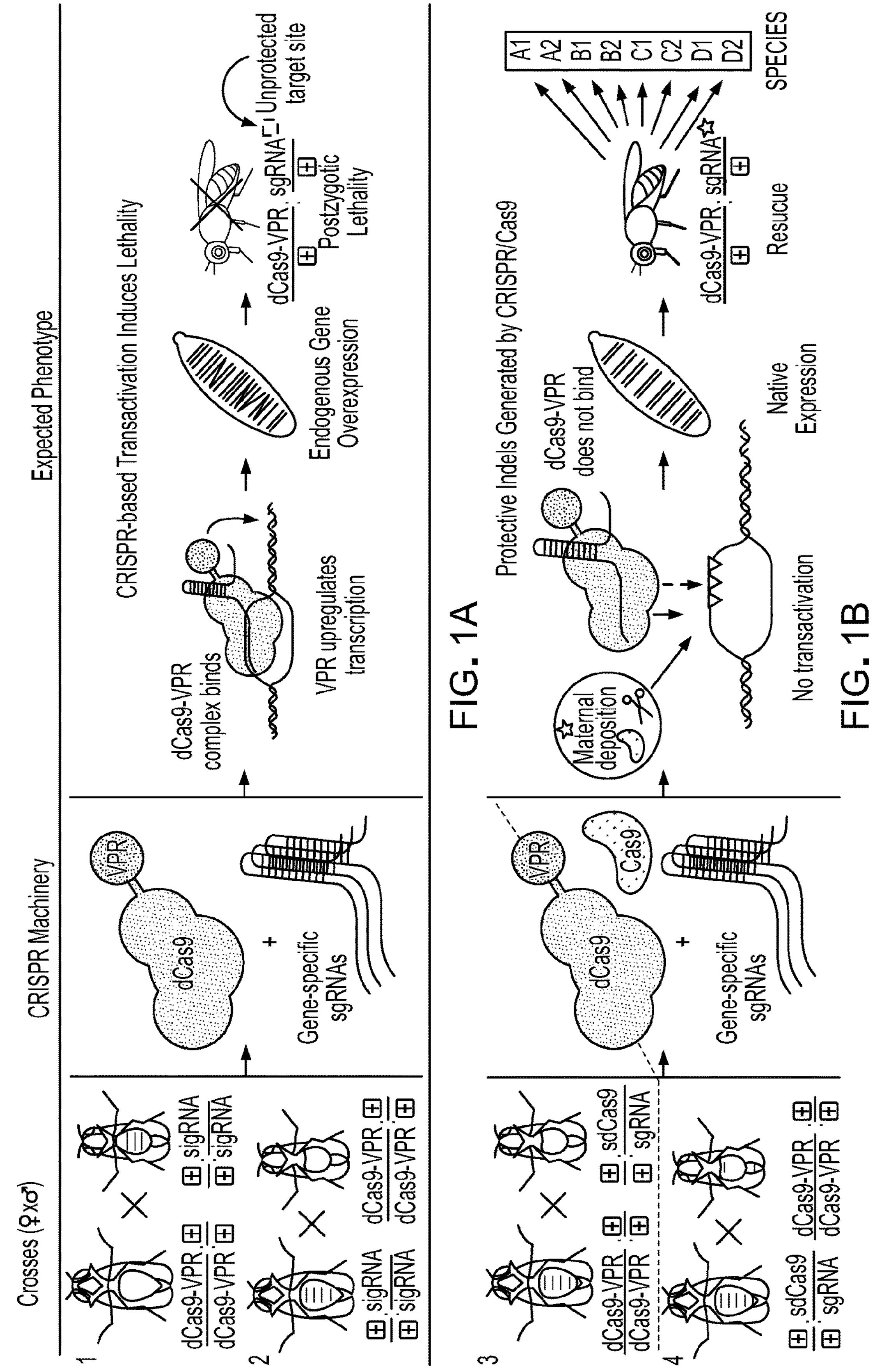
FIGS. 1A-1D show development of synthetic reproductive barriers.

Provided herein are methods for engineering reproductive barriers in an animal (e.g., insect) including (a) introducing into a first insect a first nucleic acid sequence, where the first nucleic acid sequence targets a genomic sequence, where the genomic sequence is proximal to a transcription start site of a gene product; and (b) introducing into a second insect a second nucleic acid sequence encoding a nuclease-deficient endonuclease; and (c) genetically crossing the first insect with the second insect, where the second insect includes a second copy of the genomic sequence where the second copy of the genomic sequence is proximal to a transcription start site of a second copy of the gene product, where the first nucleic acid sequence targets the genomic sequence and/or the second copy of the genomic sequence, and where in the progeny of the genetic cross between the first insect and the second insect the nuclease-deficient endonuclease binds to the genomic sequence and/or the second copy of the genomic sequence, thereby promoting expression of the (i) gene product and/or (ii) the second copy of the gene product.

The term "a" and "an" refers to one or more (i.e., at least one) of the grammatical object of the article. By way of example, "a cell" encompasses one or more cells.

As used herein, the terms "about" and "approximately," when used to modify an amount specified in a numeric value or range, indicate that the numeric value as well as reasonable deviations from the value known to the skilled person in the art, for example 20%, ±10%, or ±5%, are within the intended meaning of the recited value.

As used herein, an "effector domain" can refer to a protein interaction domain that can function in transcriptional regulation via their ability to (i) interact with the basal transcriptional machinery and general co-activators, (ii) interact with other transcriptional factors to allow cooperative binding, and (iii) directly or indirectly recruit histone and chromatin modifying enzymes.

As used herein, "engineered" or "genetically engineered," in reference to organisms (e.g., insects), refers to an organism that comprises a nucleic acid sequence (e.g., DNA, RNA, or mRNA) that is not present in, or is present at a different level than, an otherwise similar organisms under similar conditions that is not engineered (an exogenous nucleic acid), or an organism that comprises a polypeptide expressed from said nucleic acid. In some embodiments, a genetically engineered organism has been altered from its native state by the introduction of an exogenous nucleic acid, or is the progeny of such an altered organism. In some embodiments, a genetically engineered organism comprises an exogenous nucleic acid (e.g., DNA, RNA, or mRNA).

The term "exogenous" refers to any material introduced from or originating from outside a cell, a tissue or an organism that is not produced by or does not originate from the same cell, tissue, or organism in which it is being introduced.

As used herein, an "insect" can refer to any member of the largest class of the phylum Arthropoda, which is itself the largest of the animal phyla. Insects have segmented bodies, jointed legs, and external skeletons (e.g., exoskeletons). In some embodiments, an insect can include a bedbug, a housefly, a clothes moth, a Japanese beetle, an aphid, a mosquito, a flea, a horsefly, a hornet, a butterfly, or a moth. In some embodiments, an insect can be a mosquito from the genera *Stegomyia, Aedes, Anopheles*, or *Culex*. In some embodiments, the mosquito can include *Aedes aegypti, Aedes albopictus, Ochlerotatus triseriatus* (*Aedes triseriatus*), *Anopheles stephensi, Anopheles albimanus, Anopheles gambiae, Anopheles quadrimaculatus, Anopheles freebori, Culex species*, or *Culiseta melanura*. In some embodiments, the insect can include a tephritid fruit fly selected from Medfly (*Ceratitis capitata*), Mexfly (*Anastrepha ludens*), Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*), Caribbean fruit fly (*Anastrepha suspensa*), Oriental Fruit Fly (*Bactrocera dorsalis*), West Indian fruit fly (*Anastrepha obliqua*), the New World screwworm (*Cochliomyia hominivorax*), the Old World screwworm (*Chrysomya bezziana*), Australian sheep blowfly/greenbottle fly (*Lucilia cuprina*), the pink bollworm (*Pectinophora gossypiella*), the European Gypsy moth (*Lymantria dispar*), the Navel Orange Worm (*Amyelois transitella*), the Peach Twig Borer (*Anarsia lineatella*), the rice stem borer (*Tryporyza incertulas*), the noctuid moths, Heliothinae, the Japanese beetle (Papilla *japonica*), White-fringed beetle (*Graphognatus* spp.), Boll weevil (*Anthonomous grandis*), the Colorado potato beetle (*Leptinotarsa decern lineata*), the vine mealybug (*Planococcus ficus*), Asian citrus psyllid (*Diaphorina citri*), Spotted wing *Drosophila* (*Drosophila suzukii*), Bluegreen sharpshooter (*Graphocephala atropunctata*), Glassy winged sharpshooter (*Flomalodisca vitripennis*), Light brown apple moth (*Epiphyas postvittana*), *Bagrada* bug (*Bagrada hilaris*), Brown marmorated stink bug (*Halyomorpha halys*), Asian Gypsy Moth selected from the group of *Lymantria dispar asiatica, Lymantria dispar japonica, Lymantria albescens, Lymantria umbrosa*, and *Lymantria postalba*, Asian longhomed beetle (*Anoplophora glabripennis*), Coconut Rhinoceros Beetle (*Oryctes rhinoceros*), Emerald Ash Borer (*Agrilus planipennis*), European Grapevine Moth (*lobesia botrana*), European Gypsy Moth (*Lymantria dispar*), False Codling Moth (*Thaumatotibia leucotreta*), fire ants selected from *Solenopsis invicta* Buren, and *S. richteri* Forel, Old World Bollworm (*Flelicoverpa armigera*), Spotted Lanternfly (*Lycorma delicatula*), Africanized honeybee (*Apis mellifera scutellata*), Fruit and shoot borer (*Leucinodes orbonalis*), corn root worm (*Diabrotica* spp.), Western corn rootworm (*Diabrotica virgifera*), Whitefly (*Bemisia tabaci*), Flouse Fly (*Musca domestica*), Green Bottle Fly (*Lucilia cuprina*), Silk Moth (*Bombyx mori*), Red Scale (*Aonidiella aurantia*), Dog heartworm (*Dirofilaria immitis*), Southern pine beetle (*Dendroctonus frontalis*), Avocado thrip (*Thysanoptera* Spp.), Botfly selected from *Oestridae* spp. and *Dermatobia hominis*), Florse Fly (*Tabanus sulcifrons*), Florn Fly (*Flaematobia irritans*), Screwworm Fly selected from *Cochliomyia macellaria* (*C. macellaria*), *C. hominivorax, C. aldrichi*, or *C. minima*, Tsetse Fly (*Glossina* spp.), Warble Fly selected from *Flypoderma bovis* or *Hypoderma lineatum*, Spotted lanternfly (*Lycorma delicatula*), Khapra beetle (*Trogoderma granarium*), Honeybee mite (*Varroa destructor*), Termites (*Coptotermes formosanus*), Hemlock woolly adelgid (*Adelges tsugae*), Walnut twig beetle (*Pityophthorus juglandis*), European wood wasp (*Sirex noctilio*), Pink-spotted bollworm (*Pectinophora scutigera*), Two spotted spider mite (*Tertanychus urticae*), Diamondback moth (*Plutella xylostella*), Taro caterpillar (*Spodoptera litura*), Red flour beetle (*Tribolium castaneum*), Green peach aphid (*Myzus persicae*), Cotton Aphid (*Aphis gossypii*), Brown planthopper (*Nilaparvata lugens*), Beet armyworm (*Spodotera exigua*), Western flower *Thrips* (*Frankliniella occidentalis*), Codling moth (*Cydia pomonella*), Cowpea weevil (*Callosobruchus maculatus*), Pea aphid (*Acyrthosiphon pisum*), Tomato leafminer (*Tuta absoluta*), Onion *Thrips* (*Thrips tabaci*), or Cotton bollworm (*Helicoverpa armigera*).

As used herein, the term "misexpression" or "misexpressed" may refer to the process or result of altering a gene product so as to change its associated character when compared to expression of a gene product in a "native" or "non-perturbed" state.

As used herein, the terms "nucleic acid" and "nucleotide" are intended to be consistent with their use in the art and to include naturally-occurring species or functional analogs thereof. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

The term "nucleic acid" refers to a deoxyribonucleic acid (DNA) or ribonucleic acid (RNA), or a combination thereof, in either a single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the isolated nucleic acids described herein, the isolated nucleic acid is DNA. In some embodiments of any of the isolated nucleic acids described herein, the isolated nucleic acid is RNA.

Unless otherwise specified, a "nucleotide sequence encoding a protein" includes all nucleotide sequences that are degenerate versions of each other and thus encode the same amino acid sequence.

As used herein the term "promoter" may refer to a DNA sequence recognized by enzymes/proteins in a mammalian cell required to initiate the transcription of an operably linked coding sequence. A promoter typically refers, to e.g. a nucleotide sequence to which an RNA polymerase and/or any associated factor binds and at which transcription is initiated. The promoter can be constitutive, inducible, or tissue-specific (e.g., a brain-specific promoter). The promoter can be an exogenous promoter operably linked to an isolated nucleic acid. The promoter can also be a genomic sequence where the promoter is proximal to a transcription start site and at least partially controls expression of the associated gene product. A promoter within the genome can be either proximal (e.g., within 2000 nucleotides) or distal (e.g., greater than 2000 nucleotides) from a transcription start site.

The term "proximal" may refer to a distance from a transcription start site to a genomic sequence where "proximal" may include genomic sequences (e.g., a regulatory elements) within at least 2000 nucleotides either upstream or downstream. "Proximal" may also refer to a physical distance between a genomic sequence and the transcription start site. For example, in the context of three-dimensional genome organization, a genomic sequence (e.g., a regulatory element) that is distal (e.g., greater than 2000 nucleotides away from the transcription start site) can be proximal to a transcription start site because the genomic sequence "loops" around to interact with the transcription start site. One example of this is enhancer-promoter interactions where a distal enhancer is brought proximal to the promoter via a "loop" in the three-dimensional organization of the genome.

As used herein, a "reproductive barrier" or "reproductive isolation" can refer to an evolutionary mechanism, behavior, and physiological process that are critical for speciation. Reproductive barriers prevent members of different species from producing offspring, or ensure that any offspring are sterile. In some embodiments, a reproductive barrier can be a post-zygotic isolation mechanism, wherein the mechanism acts after fertilization preventing successful inter-population crossing. In some embodiments, a post-zygotic isolation mechanism can include zygote mortality, hybrid zygote abnormality, hybrid infertility, or low hybrid viability.

The term "transcription start site" may refer to the genomic location at which transcription begins.

The term "transduced", "transfected", or "transformed" refers to a process by which exogenous nucleic acid is introduced or transferred into a cell. A "transduced," "transfected," or "transformed" mammalian cell is one that has been transduced, transfected or transformed with exogenous nucleic acid (e.g., a gene delivery vector) that includes an exogenous nucleic acid encoding the first nucleic acid sequence and/or the nuclease-deficient endonuclease). In some embodiments, an exogenous nucleic acid can be introduced into a cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Dioleoyl-sn-glycero-3-phosphocholine (DOPC)), or by transporter proteins.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

Isolated Nucleic Acids

Provided herein are isolated nucleic acids that target a genomic sequence. In some embodiments, an isolated nucleic acid can target a genomic sequence, wherein the genomic sequence is proximal to a transcription start site of a gene product. In some embodiments, the isolated nucleic acid can include a guide RNA targeting the genomic sequence. In some embodiments, the isolated nucleic acid can include a single guide RNA (sgRNA).

In some embodiments, the isolated nucleic acid can include one or more RNA hairpins, wherein the RNA hairpins bind one or more RNA binding proteins fused to one or more effector domains. In some embodiments, the one or more effector domains can include at least one of an activator domain, a repressor domain, a recruitment domain, a transcription factor, or a chromatin modifier. In some embodiments, the one or more effector domains can include at least one of a SunTag, a SAM, a VPR, or a VP64. In some embodiments, the effector domain is VP64. In some embodiments, the effector domain is VPR.

Also provided herein are isolated nucleic acids that encode an endonuclease. In some embodiments, an isolated nucleic acid encodes a nuclease-deficient endonuclease. In some embodiments, the isolated nucleic acid encodes a nuclease-deficient endonuclease, wherein the nuclease-deficient endonuclease includes a CRISPR-associated sequence 9 (Cas9) endonuclease or a variant thereof, a CRISPR-associated sequence 13 (Cas13) endonuclease or a variant thereof, a CRISPR from *Prevotella* and *Francisella* 1 (Cpf1)

endonuclease or a variant thereof, a CRISPR from Microgenomates and *Smithella* 1 (Cms1) endonuclease or a variant thereof, or a CRISPR-associated sequence 6 (Cas6) endonuclease or a variant thereof. In some embodiments, the nuclease-deficient endonuclease includes a *Streptococcus pyogenes* Cas9 (SpCas9), a *Staphylococcus aureus* Cas9 (SaCas9), a *Francisella novicida* Cas9 (FnCas9), or a variant thereof. In some embodiments, the variant thereof includes a protospacer adjacent motif (PAM) SpCas9 (×Cas9), high fidelity SpCas9 (SpCas9-FIF1), a high fidelity SaCas9, or a high fidelity FnCas9. In some embodiments, the nuclease-deficient endonuclease includes a Cas fusion nuclease comprising a Cas9 protein or a variant thereof fused with a Fokl nuclease or variant thereof. In some embodiments, the nuclease-deficient endonuclease includes a CRISPR-associated sequence 9 (Cas9) endonuclease or a variant thereof. In some embodiments, the nuclease-deficient Cas9 comprises a first amino acid substitution of D10A and a second amino acid substitution of H840A. In some embodiments, the nuclease-deficient endonuclease is fused to one or more effector domains.

In some embodiments of any of the isolated nucleic acid sequences described herein, the isolated nucleic acid sequence is operably linked to a promoter (e.g., any of the exemplary promoters described herein). In some embodiments, the promoter can include a ubiquitous promoter. In some embodiments, the ubiquitous promoter is an ubiquitin-63E promoter. In some embodiments, the promoter can include an early embryonic promoter. In some embodiments, the promoter is a bottleneck/bnk promoter.

Gene Delivery Vectors

In some embodiments of any of the methods described herein, introducing a nucleic acid into an insect is facilitated by vectors. For example, a vector can be an expression vector where the expression vector includes a promoter sequence operably linked to the sequence encoding the molecule (e.g., a nucleic acid molecule). Non-limiting examples of vectors include plasmids, transposons, cosmids, and viral derived vectors (e.g., any adenoviral derived vectors (AV) cytomegaloviral derived (CMV) vectors, simian viral derived (SV40) vectors, adeno-associated virus (AAV) vectors, lentivirus vectors, and retroviral vectors), and any Gateway® vectors. A vector can, for example, include sufficient cis-acting elements for expression where other elements for expression can be supplied by the host mammalian cell or in an in vitro expression system. Skilled practitioners will be capable of selecting suitable vectors and mammalian cells for introducing any of spatial profiling reagents described herein.

In some embodiments, a vector (e.g., gene delivery vector) can include any of the isolated nucleic acids described herein. In some embodiments, the gene delivery vectors are adeno-associated viral (AAV) vectors, lentiviral vectors, adenoviral vectors, or retroviral vectors. AAV vectors are generally described in, e.g., Asokan et al., Mol. Ther. 20: 699-708, 2012, and B. J. Carter, in "Handbook of Parvoviruses", Ed., P. Tijsser, CRC Press, pp. 155-168, 1990. Adenoviral vectors are generally described in, e.g., Wold and Toth, Curr. Gene Ther. 13(6):421-433, 2013; Baron et al., Curr. Opin. Virol. 29:1-7, 2018; and Barry, Expert Rev. Vaccines 17(2): 163-173, 2018. Lentiviral vectors are generally described in, e.g., Milone and O'Doherty, Leukemia 32(7): 1529-1541, 2018, Zheng et al., Anat. Rec. 301(5): 825-836, 2018; and Cai et al., Curr. Gene Ther. 16(3): 194-206, 2016. Adenoviral vectors are generally described in, e.g., Tatsis et al., Mol. Ther. 10(4):616-629, 2004; Appaiahgari et al., Expert. Opin. Biol. Ther. 15(3):337-351, 2015; Coughlan, Methods Mol. Biol. 1108:23-40, 2014. Retroviral vectors are generally described in, e.g., Miller, Curr. Protoc. Hum. Genet. 80: Unit 12.5, 2014; Kim et al., Adv. Virus Res. 55:545-563, 2000; and Kurian et al., Mol. Pathol. 53(4):173-176, 2000. Some embodiments of any of the gene delivery vectors described herein, can include a promoter and/or enhancer (e.g., any of the exemplary tissue-specific promoter and/or enhancers described herein) that is operably linked to any of the isolated nucleic acids described herein.

In some embodiments, the gene delivery vectors described herein includes one or more (e.g., two, three, four, five, or six) of a promoter (e.g., any of the promoters described herein or known in the art), an enhancer (e.g., any of the enhancers described herein or known in the art), a Kozak sequence (e.g., any of the Kozak sequences described herein or known in the art), an RNA splicing sequence, a polyadenylation (poly(A)) signal sequence (e.g., any of the poly(A) signals described herein), and an internal ribosome entry site (IRES) sequence (e.g., any of the IRES sequences described herein or known in the art).

Compositions and Kits

Also provided are kits that include any of the isolated nucleic acids or any of the gene delivery vectors described herein. In some embodiments, a kit can include a solid composition (e.g., a lyophilized composition including any of the gene delivery vectors described herein) and a liquid for solubilizing the lyophilized composition.

Methods of Engineering a Reproductive Barrier

Provided herein are methods of engineering a reproductive barrier in an insect including: (a) introducing into a first insect a first nucleic acid sequence, wherein the first nucleic acid sequence targets a genomic sequence, wherein the genomic sequence is proximal to a transcription start site of a gene product; (b) introducing into a second insect a second nucleic acid sequence encoding a nuclease-deficient endonuclease; and (c) genetically crossing the first insect with the second insect, wherein the second insect comprises a second copy of the genomic sequence wherein the second copy of the genomic sequence is proximal to a transcription start site of a second copy of the gene product, wherein the first nucleic acid sequence targets the genomic sequence and/or the second copy of the genomic sequence, and wherein in the progeny of the genetic cross between the first insect and the second insect the nuclease-deficient endonuclease binds to the genomic sequence and/or the second copy of the genomic sequence, thereby promoting expression of the (i) gene product and/or (ii) the second copy of the gene product.

Also provided herein are methods of engineering a reproductive barrier in an insect including: (a) introducing into a first insect a first nucleic acid sequence, wherein the first nucleic acid sequence targets a genomic sequence that is proximal to a transcription start site of a gene product; and an endonuclease, wherein the endonuclease cleaves the genomic sequence, thereby creating a mutation in the genomic sequence; (b) introducing into a second insect a second nucleic acid sequence encoding a nuclease-deficient endonuclease; and (c) genetically crossing the first insect with the second insect, wherein the second insect comprises a second copy of the genomic sequence, that is proximal to a transcription start site of a second copy of the gene product, wherein the first nucleic acid sequence targets the second copy of the genomic sequence, and wherein in the progeny of the genetic cross between the first insect and the second insect the nuclease-deficient endonuclease binds to the second copy of the genomic sequence, thereby promoting expression of the second copy of the gene product.

In some embodiments, the nuclease-deficient endonuclease can interact with the genomic sequence and/or the second copy of the genomic sequence via the first nucleic acid sequence. In some embodiments, the first nucleic acid sequence includes a guide RNA targeting (i) the genomic sequence and/or (ii) the second copy of the genomic sequence. In some embodiments, step (a) includes integrating the first nucleic acid sequence into the genome of the first insect. In some embodiments, step (b) includes integrating the second nucleic acid sequence into the genome of the second insect. In some embodiments, the genomic sequence includes a regulatory element. In some embodiments, the regulatory element at least partially controls expression of the gene product. In some embodiments, the regulatory element includes a promoter, an enhancer, a silencer, an insulator, a locus control region, or a synthetic promoter. In some embodiments, the regulatory element is a promoter.

In some embodiments, the first nucleic acid sequences comprises a first gRNA and a second gRNA, wherein the first gRNA targets a first genomic sequence and the second gRNA targets a second genomic sequence. In some embodiments, the first nucleic acid sequence comprises a first gRNA, a second gRNA, and a third gRNA, wherein the first gRNA targets a first genomic sequence, the second gRNA targets a second genomic sequence, and the third gRNA targets a third genomic sequence, wherein each genomic sequence is proximal to a transcription start site of a gene product.

As used herein, a "gene product" can refer to the biochemical material (e.g., RNA or protein) that result from expression of a gene. In some embodiments, the gene product can be overexpressed when compared to wild-type gene expression. In some embodiments, expression of the gene product is lethal when misexpressed as compared to native expression. In some embodiments, the gene product includes at least one of even skipped (eve), head involution defective (hid), hedgehog (hh), or wingless (wg), or a combination thereof. In some embodiments, the combination of gene products comprises at least one of: (i) eve and hid; (ii) eve, hid, and hh; (iii) eve, hid, and wg; or (iv) hh and wg.

In some embodiments, step (a) further includes introducing into the first insect an endonuclease, wherein the endonuclease cleaves the genomic sequence, thereby creating a mutation in the genomic sequence. In some embodiments, the endonuclease comprises a CRISPR-associated sequence 9 (Cas9) endonuclease or a variant thereof, a CRISPR-associated sequence 13 (Cas13) endonuclease or a variant thereof, a CRISPR from *Prevotella* and *Francisella* 1 (Cpf1) endonuclease or a variant thereof, a CRISPR from Microgenomates and *Smithella* 1 (Cms1) endonuclease or a variant thereof, or a CRISPR-associated sequence 6 (Cas6) endonuclease or a variant thereof. In some embodiments, the endonuclease comprises a *Streptococcus pyogenes* Cas9 (SpCas9), a *Staphylococcus aureus* Cas9 (SaCas9), a *Francisella novicida* Cas9 (FnCas9), or a variant thereof. In some embodiments, the variant thereof comprises a protospacer adjacent motif (PAM) SpCas9 (×Cas9), high fidelity SpCas9 (SpCas9-FIF1), a high fidelity SaCas9, or a high fidelity FnCas9. In some embodiments, step (b) includes transiently introducing the endonuclease. In some embodiments, step (b) includes introducing mRNA encoding the endonuclease.

As used herein, a "mutation" can refer to an alteration of the nucleotide sequence of a genomic sequence. In some embodiments, a mutation can include an insertion (e.g., insertion of one or more extra nucleotides into the genomic sequence), a deletion, or a substitution mutation (e.g., a transition or a transversion). In some embodiments, the mutation prevents the first nucleic acid sequence from targeting the genomic sequence. In some embodiments, the mutation comprises an insertion or a deletion. In some embodiments, the mutation occurs within the first 20 (e.g., the first 18, the first 16, the first 14, the first 12, the first 10, the first 8, the first 6, the first 4, or the first 2) nucleotides of a PAM sequence associated with the first nucleic acid sequence. In some embodiments, the mutation occurs within the first 10 nucleotides of a PAM sequence associated with the first nucleic acid sequence. In some embodiments, the mutation in the genomic sequence does not alter expression of the gene product.

Constructing Synthetic Species

It is also possible to construct a synthetic species that is reproductively incompatible with, but otherwise identical to, its wild counterpart for ecosystem engineering (2, 4). Perhaps most interestingly, engineered reproductive isolation can be an innovative means of pest and vector control (2, 4, 5). When released into wild populations in low numbers, the reproductively isolated individuals would principally mate with wild types (WT), leading to inviable hybrid offspring and population suppression. However, releases of engineered individuals above a critical threshold would lead to more frequent intermatings, which would result in viable progeny that could eventually replace the WT populations and function as a gene drive (4-6). Importantly, this type of gene drive represents a safer alternative to certain other types of proposed drives (7, 8), as it is threshold-dependent and reversible via the release of WT individuals, which may be more palatable to both regulators and the public (7, 9).

A number of attempts to generate synthetic species barriers via engineered reproductive isolation, both within and outside the context of gene drives, have been made in the last several decades. For instance, species barriers can be engineered via genetic recoding (2), which has been attempted in bacteria (10, 11) and yeast (12, 13) though is likely infeasible in multicellular organisms. A variety of other techniques have been proposed and attempted in more complex organisms, such as flies. For example, Moreno generated a reproductively isolated strain of *D. melanogaster* using preexisting transgenes and recessive mutations (1); however, this approach utilized a complex Gal4-UAS-inducible expression system that imparted significant fitness costs on the speciated strain making it impossible for the strain to survive outside the lab, nor function as a gene drive, and also rendered the technique near impossible to transfer to non-model organisms. Several other research groups have successfully engineered under dominance systems, which cause selection against heterozygotes favoring homozygotes of either wild type or mutants, in *D. melanogaster* (5, 6, 14), although none of these systems achieved complete reproductive isolation such that when mated to WT the progeny survived and reproduced. CRISPR-based genome editing and transcriptional transactivation (CRISPRa) strategies have recently been proposed as a means for engineering synthetic reproductive barriers, and proof-of-concept systems have been constructed in both yeast and flies (2, 4); however, both of these systems failed to achieve complete reproductive isolation, as either escape mutants were readily identified or complete synthetic lethality was not achieved.

As provided herein, this disclosure features the development of synthetic reproductive barriers in *D. melanogaster* using an approach referred to as "SPECIES" (Synthetic Postzygotic barriers Exploiting CRISPR-based Incompatibilities for Engineering Species). To engineer SPECIES, CRISPR gene editing and CRISPR-based transactivation were utilized, where a nuclease-deficient deactivated Cas9 (dCas9) protein is fused to a transactivation domain that causes dCas9 expression to be lethal in WT individuals. This domain functions by recruiting transcriptional machinery to the site of single guide RNA (sgRNA) binding within the promoter region of a target gene to generate synthetic lethality by the dCas9-mediated lethal overexpression of endogenous target genes (FIG. 1A). This lethality is rescued in speciated, but not WT individuals, via the site-directed mutation of the promoter regions of endogenous target genes, thereby preventing dCas9/sgRNA binding and the lethal overexpression without interfering with target gene function (FIG. 1B).

Altogether, the findings demonstrate that dCas9-induced overexpression can be exploited to build complete synthetic reproductive barriers in vivo that could be used to drive genes through a population in a threshold-dependent manner. The SPECIES approach described here is advantageous over other previously developed technologies for several reasons. CRISPR/Cas9 has been shown to work in most organisms tested so far, and the dCas9-mediated overexpression approach does not rely on any SPECIES-specific mode of incompatibility; instead, it is easily programmable to virtually any suitable target gene and thus should be amenable to any sexually-reproducing organism with appropriate endogenous genes. Additionally, this approach can be used to construct single or multiple "stacked" genetic barriers (i.e., those utilizing more than one sgRNA), which may reduce failure due to natural variation or mutation in the sgRNA target sites, recombination, or transgene silencing/mutation. Furthermore, once a basic engineering toolkit is constructed (e.g., transgenic dCas9-VPR and Cas9-expressing lines; knowledge of suitable genes for targeting), it can be used to build multiple different SPECIES that are reproductively isolated from each other and their WT counterparts.

There are also potential limitations to building the SPECIES system in different organisms, particularly ones with minimal genome characterization. For example, this approach requires a priori knowledge of appropriate gene targets and suitable regulatory targets in these genes as well as an ability to genetically transform the target species. Additionally, there has to be a level of target gene overexpression that would cause this system to be lethal in WT individuals to attain complete reproductive isolation, which may not be easily achievable in all species. Given the potential toxicity of some of the system components, specifically the dCas9-VPR element (17), the expression of these components may need to be optimized for each new context, which may be challenging in some organisms. With the broad applicability of Cas9 tools and the relative simplicity of the SPECIES approach, however, it should be possible to implement this approach in any organism where fundamental genetic knowledge is available.

The gene drive function of the SPECIES technology is particularly useful. The threshold dependence of the SPECIES-based gene drive provides greater control and confinement (7, 18) as well as a reversibility not found in all gene drives (7, 19), which can be accomplished via WT release (6). The simplicity of the SPECIES approach and the near-universal applicability of CRISPR/Cas9 should increase the possibility of engineering organisms of medical or agricultural interest, such as mosquitoes, which also have orthologs to a number of the targeted genes described herein. The SPECIES system could be linked to a useful cargo gene—such as resistance to mosquito-borne viruses like Zika (20) or dengue (21)—to facilitate the spread of disease resistance through a population. Certainly, these cargo genes would also have to be robust enough to function in diverse wild mosquito and virus populations. Finally, given the fitness costs associated with the SPECIES system, such as dCas9 expression or incomplete indel rescue, certain SPECIES systems may not be capable of sustaining a drive in a wild population. In conclusion, the development of SPECIES demonstrates a significant advance in the field of population engineering providing a platform for future development in other organisms to safely control pest populations that pose significant burdens on humanity.

EXAMPLES

Material and Methods

Plasmid Design and Assembly

To assemble plasmid OA-986A, the base vector used for generating dCas9-expressing plasmids, several components were cloned into the piggyBac plasmid pBac[3×P3-DsRed] using Gibson assembly/EA cloning. pBac[3×P3-DsRed] was digested with BstBI and NotI, and the following components were cloned in with EA cloning: an attP sequence amplified from plasmid M{3×P3-RFP attP} with primers 986.C1 and 986.C2, a p10 3'UTR fragment amplified from Addgene plasmid #100580 with primers 986.C3 and 986.C4, an opie2 promoter fragment amplified from translocation plasmid B using primers 986.C5 and 986.C6, and an eCFP marker amplified from Addgene plasmid #47917 using primers 986.C7 and 986.C8. The resulting plasmid was then digested with PacI, and the following components were cloned in to generate the final dCas9-expressing vectors: the Ubiquitin-63E promoter fragment amplified with primers 986.C9 and 986.C10 from *D. melanogaster* genomic DNA and a dCas9-VPR fragment amplified from Addgene plasmid #78898 with primers 986.C11 and 986.C12 to generate plasmid OA-986B (Addgene #124999); the bottleneck promoter fragment amplified with primers 986.C13 and 986.C14 from *D. melanogaster* genomic DNA and a dCas9-VPR fragment amplified from Addgene plasmid #78898 with primers 986.C15 and 986.C12 to generate plasmid OA-986C (Addgene #125000); the Ubiquitin-63E promoter fragment amplified with primers 986.C9 and 986.C16 from *D. melanogaster* genomic DNA and a dCas9-VP64 fragment amplified from Addgene plasmid #78897 with primers 986.C17 and 986.C18 to generate plasmid OA-986D (Addgene #125001); and the bottleneck promoter fragment amplified with primers 986.C13 and 986.C19 from *D. melanogaster* genomic DNA and a dCas9-VP64 fragment amplified from Addgene plasmid #78897 with primers 986.C20 and 986.C18 to generate plasmid OA-986E (Addgene #125002).

To assemble plasmids OA-1045A-E, the multiple-sgRNA containing vectors, several components were cloned into the multiple cloning site (MCS) of a plasmid containing the white gene as a marker and an attB-docking site using Gibson assembly/EA cloning. First, the plasmid was digested with AsiSI and KpnI, and the following components were cloned in with EA cloning to generate base plasmid OA-1045: a *D. melanogaster* U6:3 promoter fragment sequence amplified from Addgene plasmid #49411 with primers 1045.C1 and 1045.C2, and an sgRNA scaffold fragment amplified from Addgene plasmid #49411 with primers 1045.C3 and 1045.C4. The resulting base plasmid was then used to clone final sgRNA plasmids OA-1045A-OA-1045E. To generate plasmid OA-1045A (Addgene #125003), plasmid OA-1045 was digested with AvrII; then, a fragment containing an 18 base pair (bp) eve sgRNA target site, an sgRNA scaffold, a *D. melanogaster* U6:1 promoter fragment, and an 18 bp hid sgRNA target site was amplified from a custom gBlocks® Gene Fragment (Integrated DNA Technologies, Coralville, Iowa) with primers 1045.C5 and 1045.C6, and cloned into the digested backbone using EA cloning. To generate plasmid OA-1045B (Addgene #125004), plasmid OA-1045A was digested with XbaI, and a fragment containing a Gypsy insulator, a *D. melanogaster* U6:1 promoter fragment driving expression of a first hh-targeting sgRNA, and a *D. melanogaster* U6:3 promoter fragment driving expression of a second hh-targeting sgRNA amplified from plasmid pCFD4-hh with primers 1045.C7 and 1045.C8 was cloned in using EA cloning. To generate plasmid OA-1045C (Addgene #125005), plasmid OA-1045A was digested with XbaI, and a fragment containing a Gypsy insulator, a *D. melanogaster* U6:1 promoter fragment driving expression of a first wg-targeting sgRNA, and a *D. melanogaster* U6:3 promoter fragment driving expression of a second wg-targeting sgRNA amplified from plasmid pCFD4-wg with primers 1045.C7 and 1045.C8 was cloned in using EA cloning. To generate plasmid OA-1045D (Addgene #125006), plasmid OA-1045 was digested with AscI and XbaI, and two fragments were cloned in using EA cloning: a first fragment containing a *D. melanogaster* U6:1 promoter fragment driving expression of a first wg-targeting sgRNA and a *D. melanogaster* U6:3 promoter fragment driving expression of a second wg-targeting sgRNA amplified from plasmid pCFD4-wg with primers 1045.C9 and 1045.C10, and a second fragment containing a Gypsy insulator, a *D. melanogaster* U6:1 promoter fragment driving expression of a first hh-targeting sgRNA, and a *D. melanogaster* U6:3 promoter fragment driving expression of a second hh-targeting sgRNA amplified from plasmid pCFD4-hh with primers 1045.C11 and 1045.C12. Finally, to generate plasmid OA-1045E (Addgene #125007), plasmid OA-1045 was digested with AvrII and NotI, and a fragment comprising *D. melanogaster* Gly tRNA-flanked sgRNAs targeting, 5' to 3', eve, hid, and hh followed by a *D. melanogaster* U6:3 UTR that was amplified with primers 1045.C13 and 1045.C14 from a gene synthesized vector (GenScript, Piscataway, NJ) was cloned in using EA cloning. All primers used for cloning are listed in Table 1.

Fly Culture and Strains

Fly husbandry and crosses were performed under standard conditions at 25° C. Rainbow Transgenics (Camarillo, CA) carried out all of the fly injections. Fly strains utilized to generate dCas9-expressing lines were attP lines attP40w (Rainbow Transgenic Flies line; yw P{nos-phiC31\int.NLS}X;P{CaryP}attP40) and 8621 (BSC #8621; y[1] w[67c23]; P{y[+t7.7]=CaryP}attP1). The fly strains used to generate sgRNA-expressing lines were 86Fa (BSC #24486: y[1] M{vas-int.Dm}ZH-2A w[*]; M{3×P3-RFP.attP'}ZH-86Fa), 9732 (BSC #9732: y[1] w[1118]; PBac{y[+]-attP-9A}VK00013), and 8622 (BSC #8622: y[1] w[67c23]; P{y[+t7.7]=CaryP}attP2). For balancing chromosomes, fly stock BSC #39631 (w[*]; wg[Sp-1]/CyO; P{ry[+t7.2]=neoFRT}82B lsn[SS6]/TM6C, Sb[1]) was used. All lines were homozygous-viable.

Generation and Genetics of Speciated Stocks

Single sgRNA lines targeting eve, hid, hh, and wg were utilized. dCas9-VPR- and dCas9-VP64-expressing lines were generated via microinjection as described above; a transgenic line that expressed dCas9-VPR ubiquitously could not be generated, despite numerous attempts, suggesting that such expression was toxic. To test for the ability of all sgRNA lines to induce lethal overexpression ("killing"), five sgRNA males and five virgin females were separately crossed to five dCas9 line individuals of the opposite sex in single vials and were allowed to mate for 7 days. After 7 days, the parents were removed, and the vials were monitored for 7 additional days to assess whether viable larvae were present. No killing was observed in crosses of dCas9-VP64 expressing lines to any of the sgRNA-expressing lines (FIGS. 1A-1D), consistent with previous observations. Complete killing was presumed when no larvae were present after 14 days. All experiments were done in biological triplicate.

To generate protective indel mutations, a Ubiquitin-Cas9 line (BSC #79005) was used. Briefly, ten Ubiquitin-Cas9 virgin females were crossed to ten sgRNA males, and virgin female and male progeny with both transgenes were selected and crossed to each other for at least three generations. Cas9/sgRNA transheterozygous virgins were then outcrossed in groups of 3-5 to homozygous attP40w bnk-dCas9-VPR males, and progeny containing both a sgRNA (identified by the presence of the w+ marker) and bnk-dCas9-VPR (identified by the presence of the opie2-eCFP marker) were isolated as "rescue" individuals that presumably carried protective indel mutations in the target promoter regions that prevented dCas9-induced overexpression (FIGS. 1A-1D, Tables 2-3). To confirm the generation of indels, these flies were Sanger sequenced and crossed to each other, again in groups of 3-5, to establish "rescue" stocks.

These "rescue" crosses were also set up in the reverse direction, utilizing 3-5 homozygous attP40w bnk-dCas9-VPR females crossed to Cas9/sgRNA transheterozygous males, to determine whether maternal deposition of Cas9/sgRNAs is required for generating sufficient protective indel mutations to provide rescue of lethality. In particular, it was assumed that, if both copies of the targeted promoter needed to contain protective indel mutations to provide rescue, lack of maternally deposited Cas9/sgRNA (due to Cas9/sgRNA fathers being used) would lead to lack of "rescue" individuals, as all individuals inheriting the sgRNA and bnk-dCas9-VPR transgenes would still have one wildtype copy of the target promoter inherited from the mother available for targeting and would perish.

To further validate whether both copies of the targeted promoter needed to contain protective indel mutations to provide rescue from lethality, "rescue" individuals were also bidirectionally outcrossed in groups of 3-5 and in triplicate to homozygous attP40w bnk-dCas9-VPR individuals, and the resulting progeny were scored for the "rescue" phenotype. Here, it was presumed that the lack of transheterozygous sgRNA/bnk-dCas9-VPR progeny indicated that both copies of the targeted promoter needed to contain protective indel mutations to provide rescue and that the lack of such mutations in the promoter allele inherited from the homozygous attP40w bnk-dCas9-VPR parent led to lethality in the transheterozygous sgRNA/bnk-dCas9-VPR progeny. Here, too, such lethality was observed for crosses with multiple sgRNA transgenes but not for crosses with single sgRNA transgenes, suggesting that, in the case of the latter, one wildtype copy of the targeted promoter was not sufficient to lead to sgRNA/bnk-dCas9-VPR induced lethality.

Double homozygous speciated stocks were generated for all sgRNA combinations by crossing dCas9/sgRNA heterozygotes that lacked the Ubiquitin-Cas9 transgene (as evidenced by lack of red fluorescence) and identifying homozygous progeny by eye color (orange to dark red eyes for homozygotes vs. yellow to light red eyes for heterozygotes, depending on sgRNA insertion site) and opie2-eCFP intensity. Putative double homozygous individuals were then outcrossed to w[1118] individuals of the opposite sex in groups of three per vial to test for reproductive isolation. Flies were allowed to mate and lay eggs for 7 days, and vials were checked daily for hatched embryos. Flies that failed to fruitfully mate with w[1118] were presumed to be reproductively isolated double homozygotes and were then crossed to putative double homozygotes of the opposite sex to generate a double homozygous, reproductively isolated stock for each sgRNA line.

Assessment of Reproductive Isolation from Various Strains

To determine whether double-homozygous speciated lines were reproductively isolated from stocks that were genetically diverse, speciated individuals were outcrossed to various Global Diversity Lines (GDL) isolated from five different continents, and used in previous work examining gene drive function in different genetic contexts. Briefly, 5 double homozygous individuals from each speciated stock were outcrossed to 5 individuals of the opposite sex from each of five Global Diversity Lines (from Beijing, China; Ithaca, NY; the Netherlands; Tasmania, Australia; and Zimbabwe, Africa). All crosses were done bidirectionally with respect to sex, and in triplicate. Flies were allowed to mate and lay eggs for 7 days, and vials were checked daily for hatched embryos for the following 7 days. Lack of embryo hatching was presumed to indicate reproductive isolation.

Figure 11A:
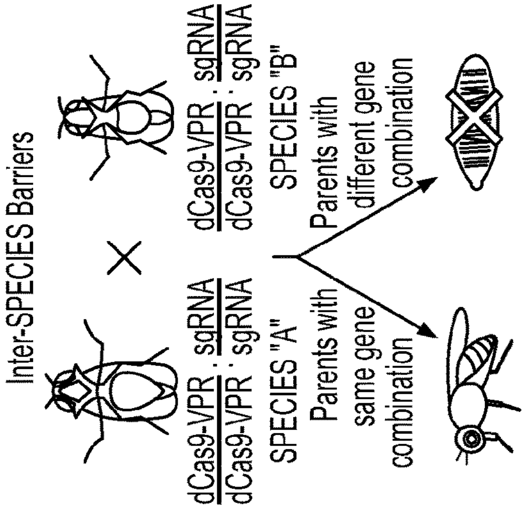
FIGS. 11A-11B show reproductive isolation between double-homozygous spectated lines.
Figure 11B:
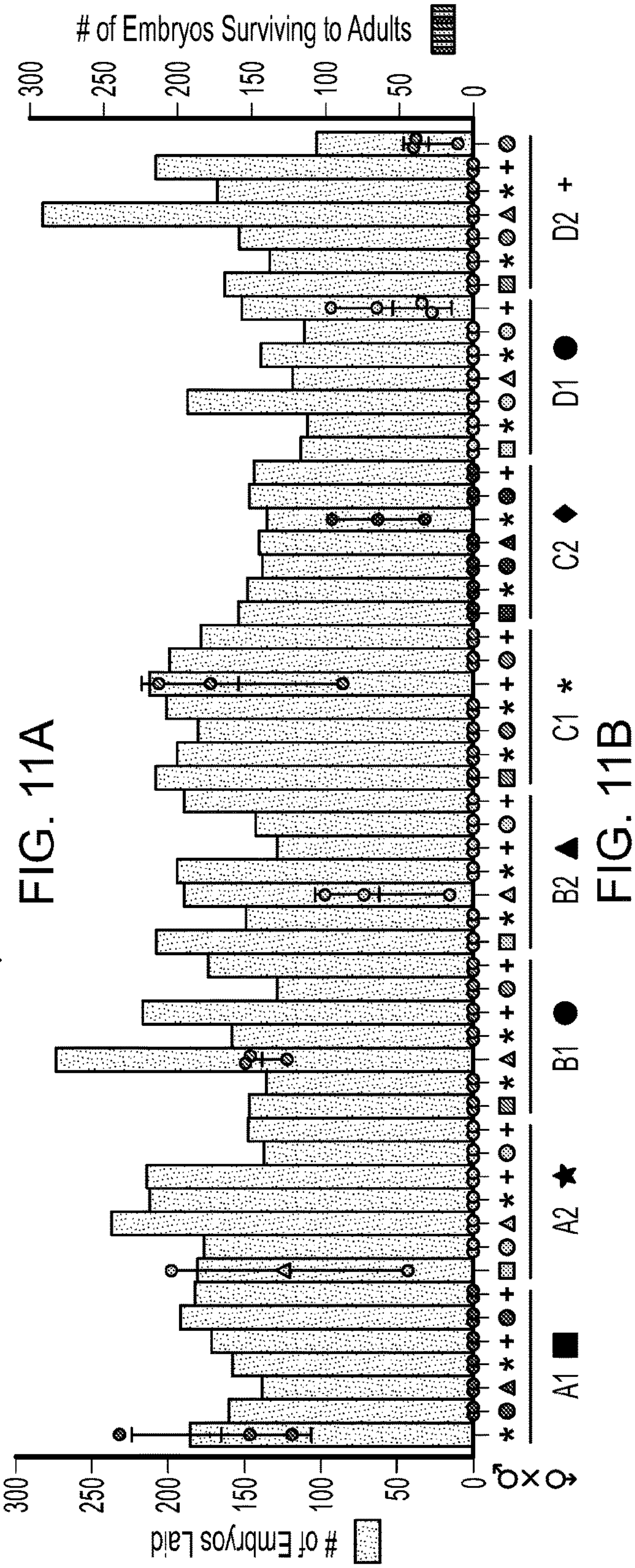
Figure 12A:
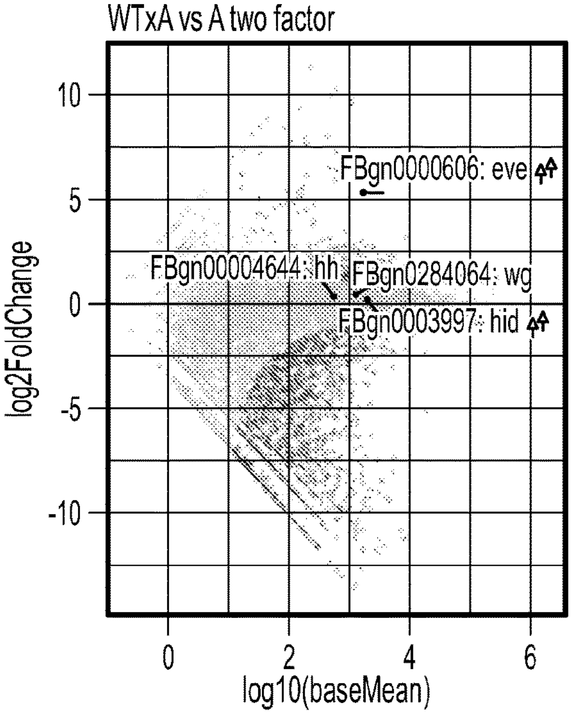
FIGS. 12A-12D show Two-Factor RNAseq comparisons.
Figure 12B:
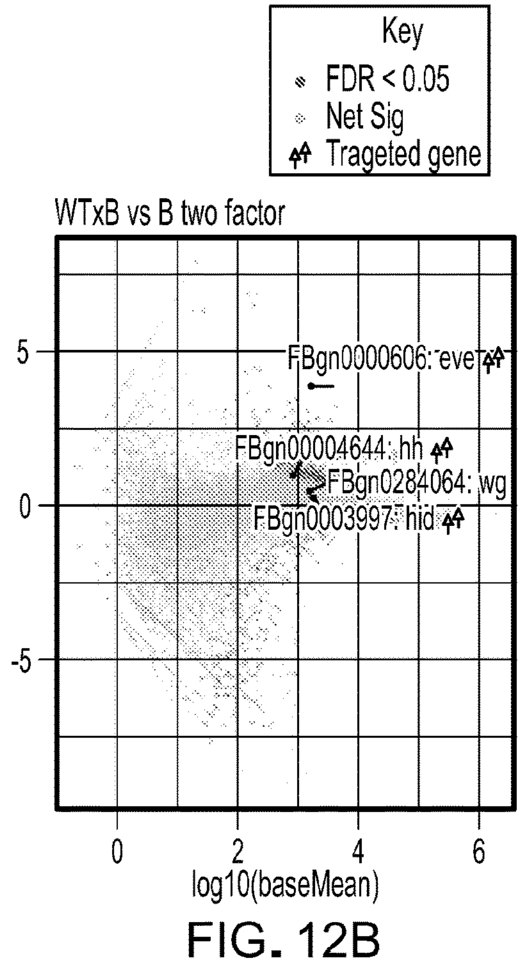
Figure 12C:
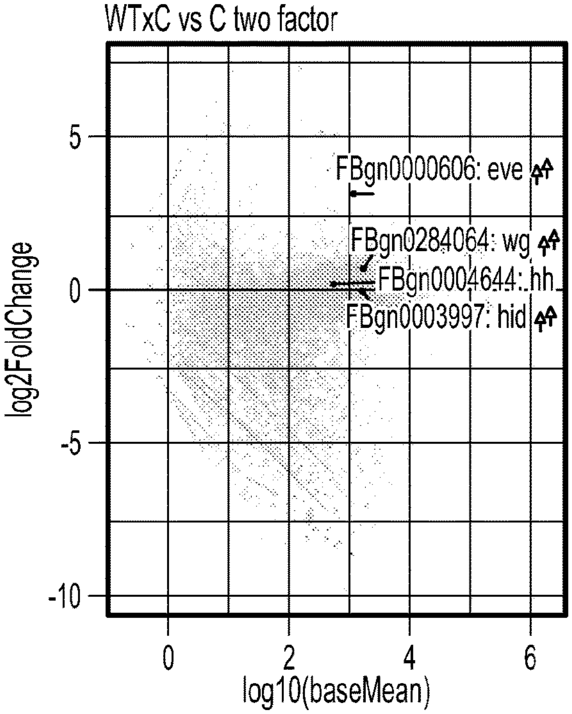
Figure 12D:
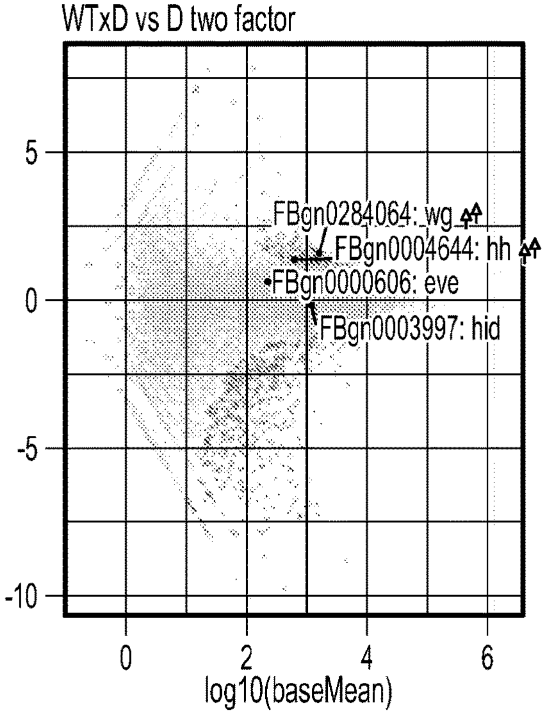
Figure 13:
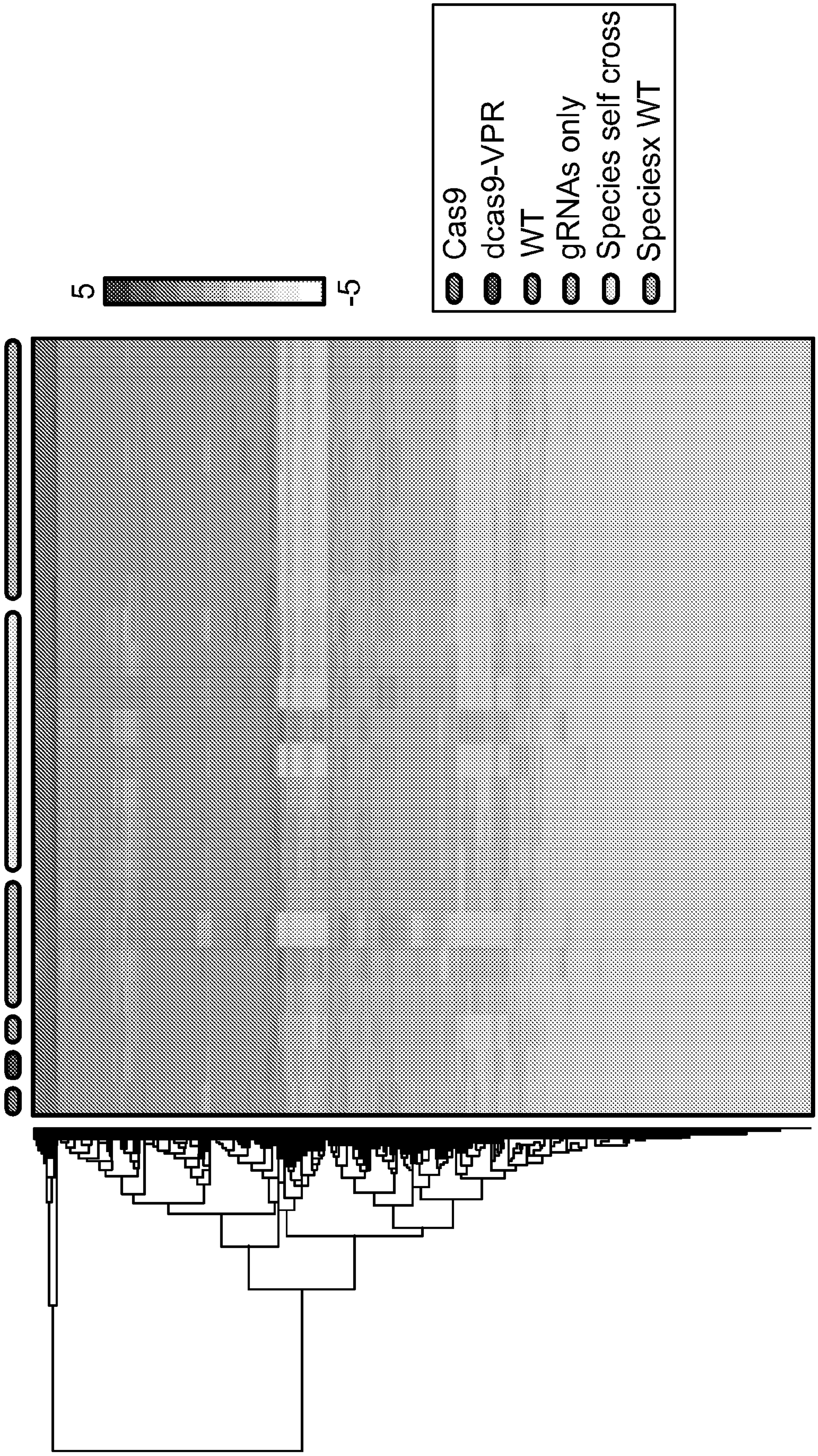
FIG. 13 shows a hierarchical clustering heat map of the RNAseq data.

To assess reproductive isolation between double-homozygous speciated lines, inter-species crosses were performed by crossing 2 speciated virgin females with 2 speciated males from each strain. Flies were allowed to mate for 12-16 hours under standard conditions; following this period, the adult flies were removed and the embryos were counted (FIGS. 11A-11B, Table 7). The vials were aged at 26° C. for 24 hours and subsequently scored for number of hatched embryos (if complete speciation did not occur). The vials were then kept at 26° C. for 7-10 days to ensure no pupae/adults emerged in instances of complete speciation, or to count emerged adults in instances of incomplete speciation (FIGS. 11A-11B).

Embryo and Adult Viability Determination

For embryo viability counts (FIGS. 2A-2D), 3-4 day old adult virgin females were mated with males of the relevant genotypes for 2-3 days in glass vials supplemented with *Drosophila* medium and yeast paste. Following this period, the adults were transferred to an egg collection chamber containing a grape juice agar plate. Females were allowed to lay at 26° C. for 12 hours, after which the adults were removed and the total number of embryos were scored. These embryos were kept on the agar surface at 26° C. for 24 hours. The % survival was then determined by counting the number of unhatched embryos. One group of 100-300 embryos per cross was scored in each experiment, and each experiment was carried out in biological triplicate. The results presented are averages from these three experiments. Embryo survival was normalized with respect to the % survival observed in parallel experiments carried out with the Oregon R wild-type strain, which was 91.66%. For adult fly counts (FIGS. 2A-2D), the agar plates were transferred to 250 ml plastic bottles with *Drosophila* medium and kept at 26° C. for 7-10 days. Following this period, the number of adults emerged was scored. The percentages of adult survival presented are averages from each cross normalized with respect to the % survival observed in Oregon R, which was 58.04%; all crosses were set in triplicate. Unpaired t-test statistical analyses were carried out for both embryo and adult fly counts to compare expected and observed values. For species crossed to themselves, significant differences were found in embryo survival for species A2 and C1 compared to WT crossed to itself (p-values 0.0322 and 0.0325 respectively) but not for any of the remaining six species. For species outcrossed to WT, significant differences were found for all bidirectional crosses of each species to WT when compared to WT crossed to itself. This significance was seen in experiments for both embryo and adult fly survival (p-value<0.05).

Population Cage Experiments

Figure 4:
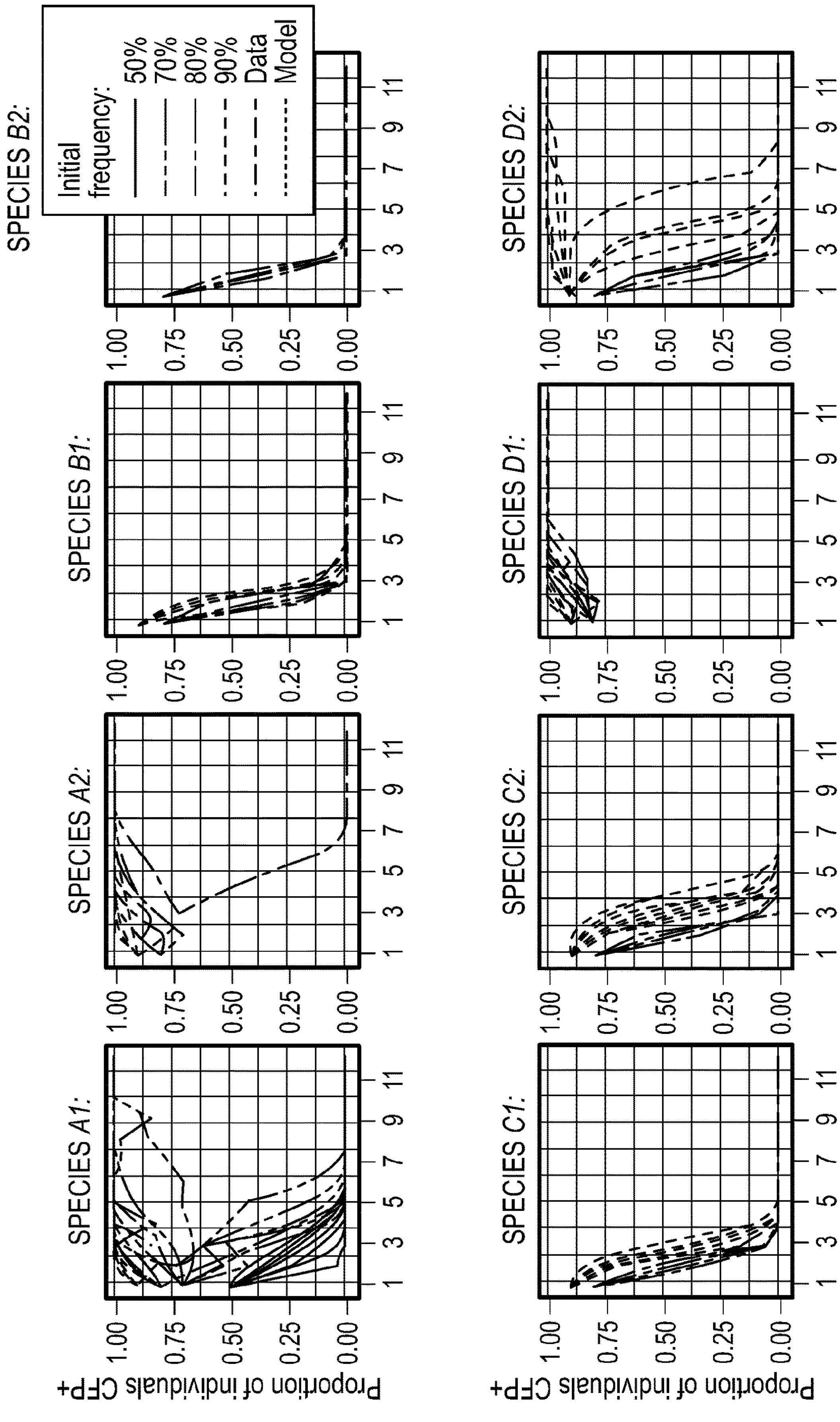
FIG. 4 shows population experiments and model fits for eight SPECIES demonstrating threshold-dependent population replacement. Population experiments mated SPECIES individuals with WT individuals, producing first generation SPECIES population frequencies of 50, 70, 80, and 90% for system A1; 80 and 90% for systems A2, B1, C1, C2, D1, and D2; and 90% for system B2. Results are shown as solid lines, while fitted model predictions are dashed lines. Observed data are consistent with fitness costs of SPECIES strains relative to WT. Ten stochastic model predictions are shown for each release frequency, assuming a population size of 50. Proportion of individuals CFP+ represents the percentage of SPECIES individuals at each generation.
Figures 5A, 5B, 5C, 5D, 5E, 5F:
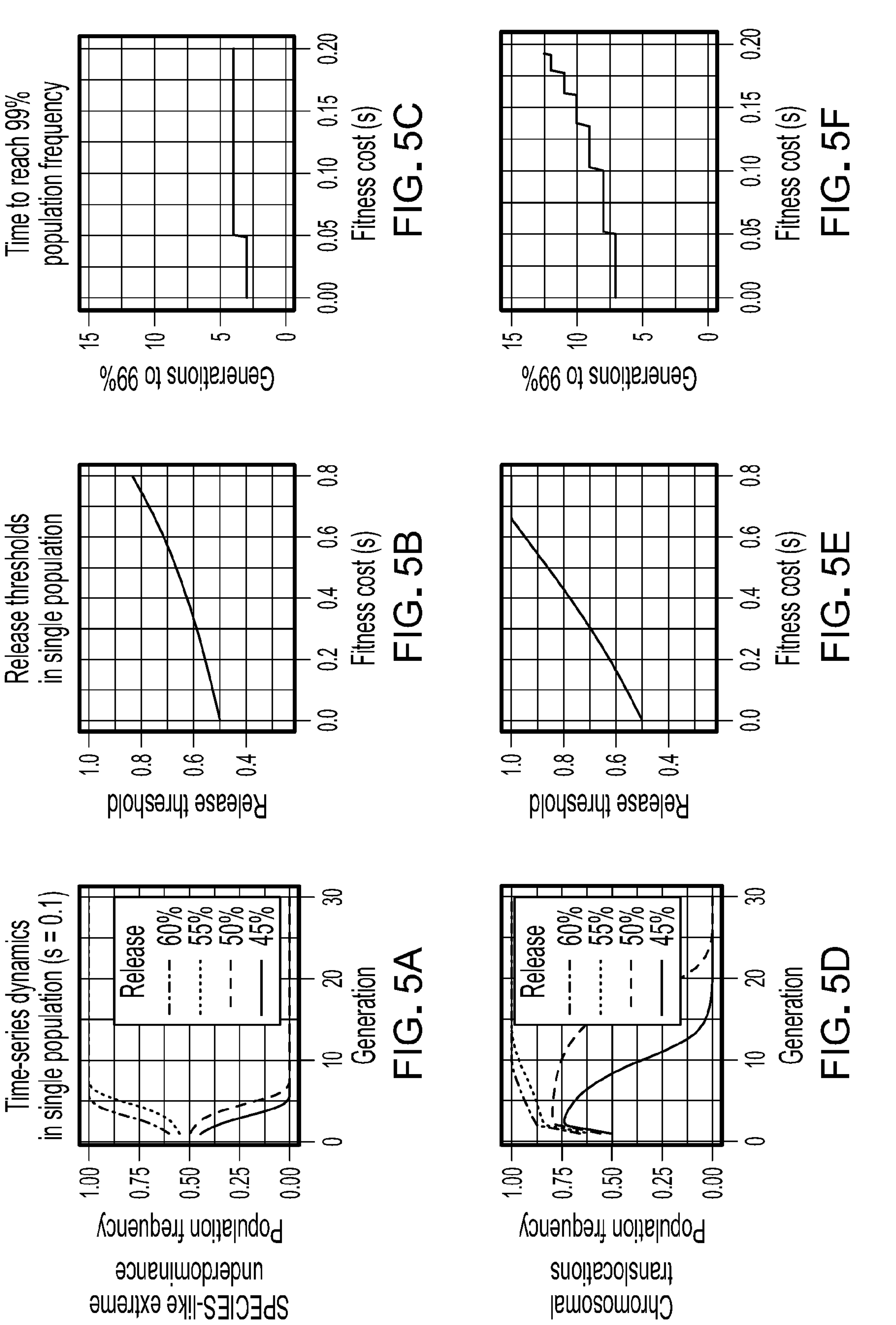
FIGS. 5A-5I show population dynamics of underdominant systems in a single population.
Figure 5I:
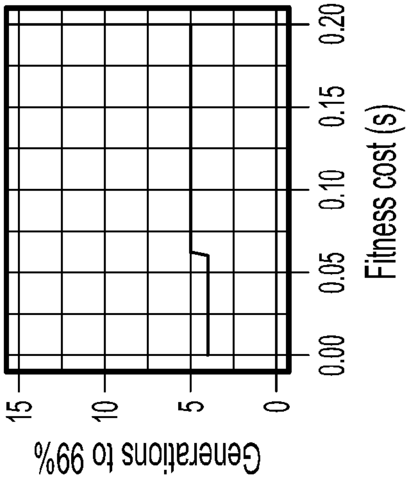
Figure 5H:
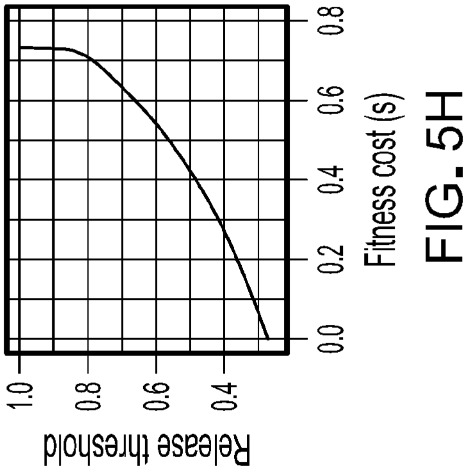
Figure 5G:
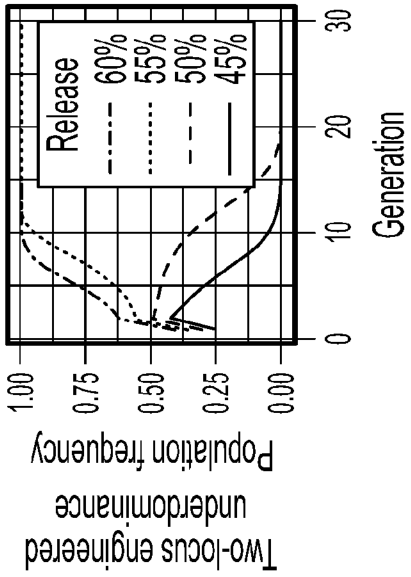
Figure 6A:
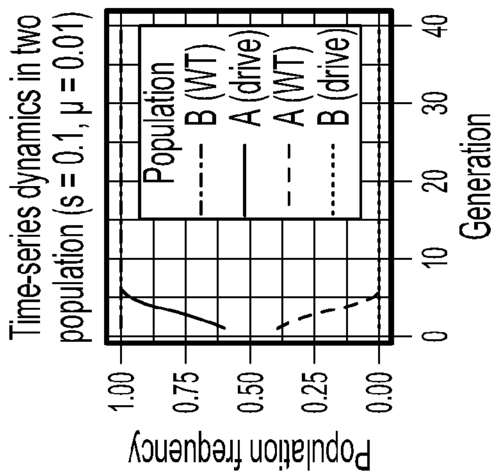
FIGS. 6A-6I show population dynamics of underdominant systems in two populations.
Figure 6B:
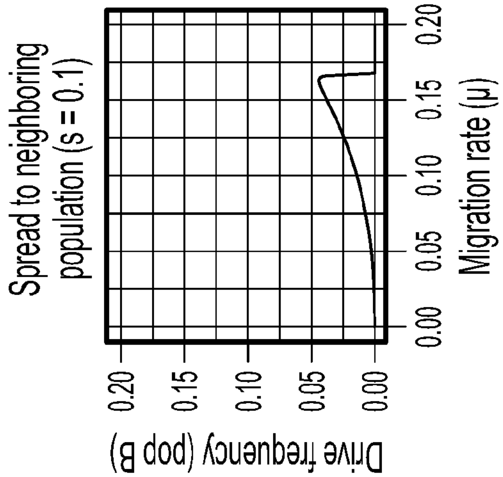
Figure 6C:
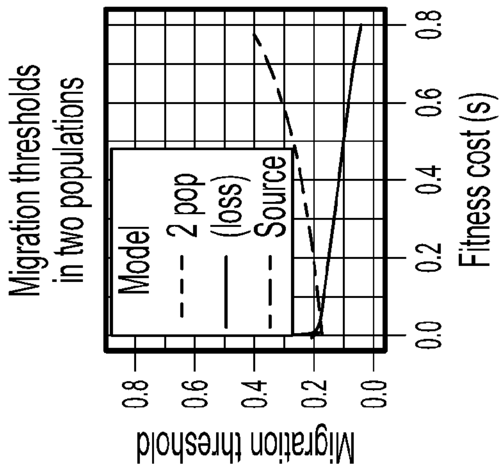
Figure 6D:
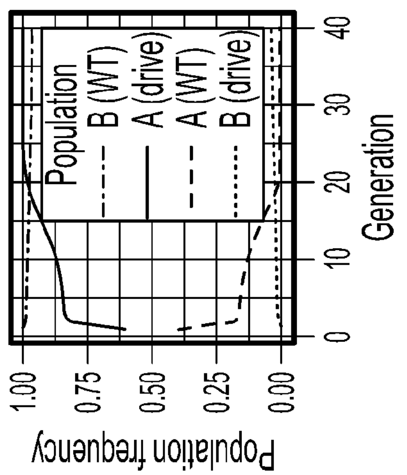
Figure 6E:
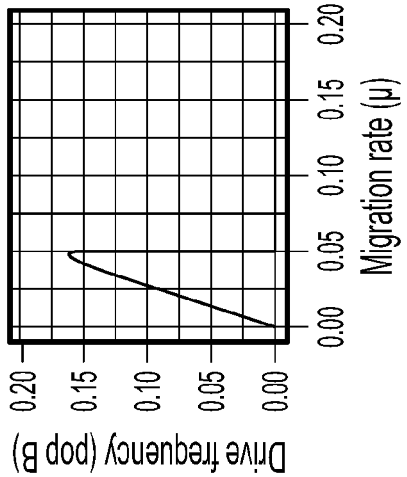
Figure 6F:
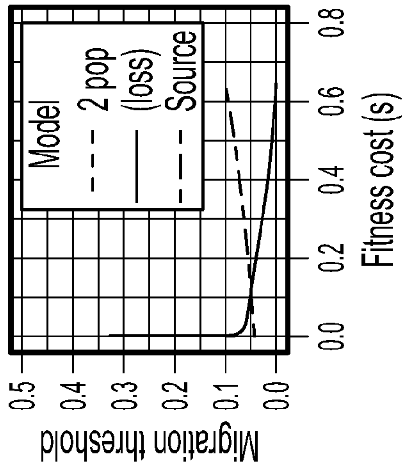
Figure 6I:
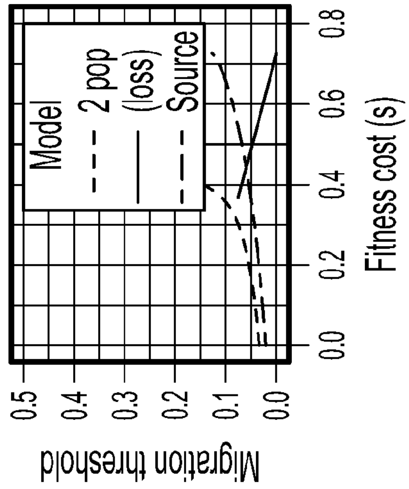
Figure 6H:
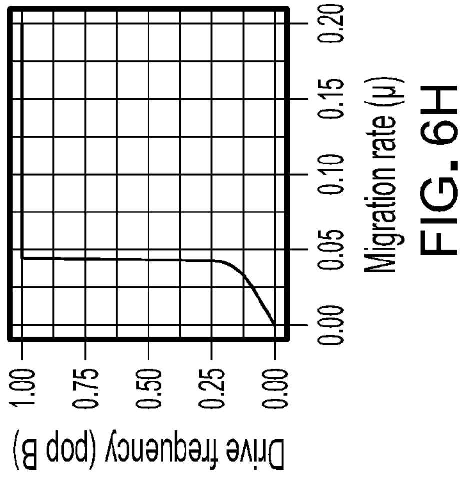
Figure 6G:
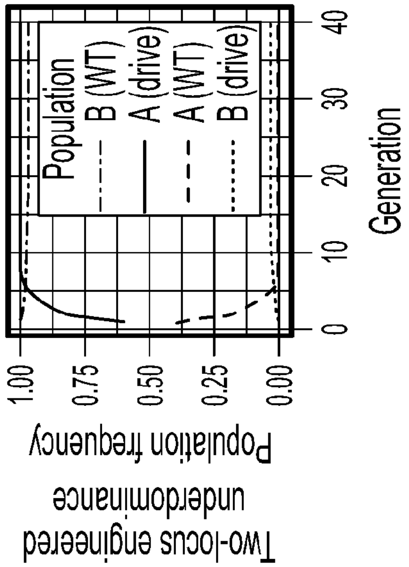

All genetic experiments were conducted in a high-security Arthropod Containment Level 2 (ACL2) barrier facility, in accordance with protocols approved by the Institutional Biosafety Committee from University of California San Diego. Population cage experiments were carried out at 26° C., 12 hour-12 hour day night cycle, with ambient humidity in 250 ml bottles containing Lewis medium supplemented with live, dry yeast. Starting populations for drive experiments included equal numbers of virgins and males of similar ages, for each genotype. Speciated double homozygotes (dCas9/dCas9; +/+) were introduced at a population frequency of 80% for above threshold drive experiments, and 50% for below threshold drive experiments. OreR virgin females and males (+/+; +/+) of similar age as the translocation-bearing individuals made up the remainder of the population. The total number of flies for each starting population was 100. All experiments were conducted in triplicate. After being placed together, adult flies were removed after seven days. After another seven days, progeny were collected and the fraction of speciated double homozygous individuals was determined (FIG. 4). The progeny were then placed into a new bottle to initiate the next generation. No significant evidence of crowding in the 250 ml bottles was observed.

Mathematical Modelling

SPECIES population dynamics were modeled under laboratory conditions assuming random mating and discrete generations. A SPECIES allele, "T", and a corresponding wildtype allele, "t", were considered. Since heterozygotes for the SPECIES system are unviable, there are only two viable genotypes-TT and tt. It was denoted such that the proportion of organisms having the genotype TT at generation k by $p_k$, and the proportion having the wildtype genotype at generation k by $(1-p_k)$. By considering all possible mating pairs, and assuming a fitness cost for TT individuals relative to wildtype individuals, s, the frequency of TT individuals in the next generation is given by:

$$p_{k+1} = p_k^2(1-s)/\left(p_k^2(1-s) + (1-p_k)^2\right). \tag{1}$$

The threshold frequency is an unstable equilibrium that satisfies the condition:

$$p_{k+1} = p_k. \tag{2}$$

Substituting Eq. (2) into Eq. (1) and solving for $p_k$, two stable equilibria ($p_k=0$ and $p_k=1$) and one unstable equilibrium ($p_k=1/(2-s)$) were found. The latter represents the critical threshold frequency, above which the SPECIES system is more likely to spread to fixation than not, and below which it is more likely to be eliminated than not.

The likelihood of the population data for each SPECIES system was calculated by assuming a binomial distribution of wildtype (CFP−) and SPECIES (CFP+) individuals, and by using the model in Eq. (1) to generate expected proportions for each fitness parameter value, s, i.e., by calculating the log-likelihood:

$$\log L(s) = \sum_{i=1}^{j}\sum_{k=1}^{n_i}\log\left(\frac{TT_{i,k} + tt_{i,k}}{TT_{i,k}}\right) + TT_{i,k}\log(p_k(s)) + tt_{i,k}\log(1 - p_k(s)). \quad (3)$$

Here, (1) $TT_{i,k}$ and $tt_{i,k}$ are the number of SPECIES (CFP+) and wildtype (CFP−) individuals at generation k in experiment i, respectively, (2) there are a total of j experiments for this SPECIES system, (3) the ith experiment is run for n, generations, and (4) the expected genotype frequencies are dependent on the fitness parameter, s. The initial condition for each experiment is specified by the data. Fitness parameters, including 95% credible intervals, were estimated using a Markov chain Monte Carlo sampling procedure.

The stochastic simulations in FIG. 4 were implemented by calculating expected genotype frequencies in the next generation according to Eq. (1), and taking a binomial sample from a total of 50 individuals.

Comparative modeling of other underdominant systems is described in Marshall and Hay (*J. Theor. Biol.* 294, 153-171 (2012)). Marshall et al uses the mathematical modeling framework described here in addition to two approaches for modeling migration: (1) a "two-population model", in which reciprocal movement occurs between the two connected populations; and (2) a "source model", in which the system is initially fixed in the source population, absent from the sink population, and one-way migration occurs from the source to sink population. In Marshall et al., population replacement and confinement dynamics are shown for: (1) extreme underdominance (the SPECIES system modeled here), (2) reciprocal chromosomal translocations, (3) single-locus and two-locus engineered underdominance, (4) Semele, (5) inverse Medea, and (6) Merea (Medea with a recessive antidote). A range of parameter values are compared for each gene drive system, including fitness cost (s, varied between 0 and 30%) and migration rate (m, varied between 0 and 10% per individual per generation for both the source and two-population models).

Results from that analysis suggest that SPECIES-like extreme underdominant systems fare well against other underdominance-based gene drive systems in terms of both confinement and persistence. The most direct comparison can be made to translocations, which also have a 50% release threshold in a single population and in the absence of a fitness cost. Considering a 5% fitness cost for both systems, they still have very similar release thresholds (51.3% for SPECIES-based underdominance cf. 52.8% for translocations); however, for a two-population model with a migration rate of 1% per individual per generation, the SPECIES-based underdominant system spreads to only ~0.01% in the neighboring population, while the translocations spread to a much higher ~4.2% in the neighboring population. The migration rate at which the introduced system is lost due to inward migration of wild types is also much higher for the SPECIES-based underdominant system (17.6% per individual per generation cf. 5.8% for translocations, s=0.05). This suggests that SPECIES-like extreme underdominant systems are preferable to translocations for local population replacement since they lead to less contamination of neighboring populations and are less vulnerable to elimination due to inward migration (FIGS. 5A-5I and 6A-6I).

Finally, were SPECIES-based underdominant systems to be implemented for local population replacement, strains would likely be used that would have much smaller fitness costs than those observed here (~30%). Despite that, results from Marshall et al. suggest the population dynamics of the SPECIES system are resilient in the face of these fitness costs. A SPECIES system with a fitness cost of 30% has a release threshold of 58.8%, which could be exceeded through weekly releases over several weeks. Furthermore, in a two-population model, the migration rate at which the SPECIES system would be lost due to inward migration of wild types is 13.3% per individual per generation, which is greater than the movement rate observed between populations of *Anopheles gambiae*, the main mosquito vector of malaria in Sub-Saharan Africa, and *Aedes aegypti*, the main mosquito vector of dengue, Zika and Chikungunya viruses.

RNA Sequencing for Transcriptional Activation Analysis

Embryos were collected from the multiple speciated lines to assess transactivation in the embryo. Male speciated flies were crossed to Oregon R virgin females in glass vials supplemented with *Drosophila* medium and yeast paste, and incubated at 26° C. for 72 hours. Following this period, the adult flies were transferred to collection chambers containing grape juice agar plates. The flies were allowed to lay for 4-5 hours, after which the embryos were aged for one hour and collected using a paintbrush. 30-50 5-6 hr embryos were collected, washed with ddH2O, and transferred to individual eppendorf tubes. The samples were flash frozen with liquid nitrogen and stored at −80° C. Intra-crosses for Oregon R, Cas-9, dCas-9, dgRNA, and speciated lines were also performed and collected as controls. Each sample was homogenized and processed using the Quick-Start Protocol of the miRNeasy Mini Kit (Qiagen, Hilden, DEU), followed by DNase treatment using the DNA-Free™ Kit and protocol (Thermo Fisher Scientific, Waltham, MA, USA).

RNA-Seq Library Construction and Sequencing

RNA integrity was assessed using RNA 6000 Pico Kit for Bioanalyzer (Agilent Technologies #5067-1513) and mRNA was isolated from ~1 μg of total RNA using NEBNext Poly(A) mRNA Magnetic Isolation Module (NEB #E7490). RNA-seq libraries were constructed using NEBNext Ultra II RNA Library Prep Kit for Illumina (NEB #E7770) following manufacturer's instructions. Briefly, mRNA was fragmented to the average size of 200 nt by incubating at 94° C. for 15 min in first strand buffer, cDNA was synthesized using random primers and ProtoScript II Reverse Transcriptase followed by second strand synthesis using NEB Second Strand Synthesis Enzyme Mix. Resulting DNA fragments were end-repaired, dA tailed and ligated to NEBNext hairpin adaptors (NEB #E7335). After ligation, adaptors were converted to the 'Y' shape by treating with USER enzyme and DNA fragments were size selected using Agencourt AMPure XP beads (Beckman Coulter #A63880) to generate fragment sizes between 250 and 350 bp. Adaptor-ligated DNA was PCR amplified followed by AMPure XP bead clean up. Libraries were quantified with Qubit dsDNA HS Kit (ThermoFisher Scientific #Q32854) and the size distribution was confirmed with High Sensitivity DNA Kit for Bioanalyzer (Agilent Technologies #5067-4626). Libraries were sequenced on Illumina HiSeq2500 in single read mode with the read length of 50 nt and sequencing depth of 20 million reads per library following manufacturer's instructions. Base calls were performed with RTA 1.18.64 followed by conversion to FASTQ with bcl2fastq 1.8.4.

Quantification and Differential Expression Analysis

Reads were mapped to the *Drosophila melanogaster* genome (BDGP release 6, GenBank accession GCA_000001215.4) using STAR aligner with default parameters with the addition of '--outFilterType BySJout' filtering option and '--sjdbGTFfile *Drosophila_melanogaster*.BDGP6.22.97.gtf' GTF file downloaded from ENSEMBL. Expression levels were determined with featureCounts using '-t exon -g gene_id -M -O --fraction' options. Differential expression analyses between homozygous speciation stocks and corresponding heterozygotes outcrossed to wild-type females were performed with DESeq2 using a two factor design formula 'design=~line+genotype'. Two independent lines per each target sets (genotype) were used. MA plots (log 2(FoldChange) vs log 10(baseMean)) were generated with ggplot2. All sequencing data can be accessed at NCBI SRA (study accession ID PRJNA578541).

Immunohistochemistry

For antibody staining, embryos were collected overnight and then fixed and dechlorinated using standard protocols. Guinea pig anti-Runt polyclonal antibody was used at a concentration of 1:200 and mouse anti-Eve monoclonal 3C10 at 1:20. Nuclei were counterstained with DAPI. Embryos were stained using standard protocols.

Cuticle Preparation

Embryos were collected and aged at 27° C. until they were 16-22 h old. Embryos were pipetted onto a slide and excess fluid was removed. Glacial acetic acid mixed 1:1 with Hoyer's solution was added, covered with a coverslip, and allowed to dry for several days in an oven at 65° C. for clearing. After 24 h, the coverslips were weighted to flatten the preps. Cuticles were imaged on an upright Zeiss Axio Imager microscope with bright field illumination, and grayscale images were later inverted and oversaturated for increased contrast using Adobe Photoshop.

Molecular Characterization of Protective Indel Mutations

To examine the molecular changes that conferred protection from dCas9-mediated overexpression and associated lethality, four genomic loci that include targets sites for four functional gRNAs (FIG. 10) were amplified and sequenced. Single-fly genomic DNA preps were prepared using the solid tissues protocol of the Quick-DNA™ Miniprep Plus Kit (Zymo Research). In total, 2-3 µl of genomic DNA was used as a template in a 50-µL PCR reaction with Q5® High-Fidelity 2× Master Mix (NEB, Ipswich, MA, USA). The following primers were used to amplify the loci with the corresponding gRNA targets: 1001.IS and 1001.S4 for hedgehog (hh); 1045.S1 and 1045.S4 for wingless (wg); 1045.S5 and 1045.S8 for even skipped (eve); and 1045.S9 and 1045.S12 for head involution defective (hid). PCR products were loaded and run on an agarose gel, excised, and purified using a Zymoclean™ Gel DNA Recovery Kit (Zymo Research, Irvine, CA, USA), and sequenced in both directions using Sanger sequencing at Retrogen Inc (San Diego, CA, USA). To characterize molecular changes at the targeted sites, ABi sequence files were aligned against the corresponding reference sequences (downloaded from FlyBase release FB2019_3) in SnapGene® 4 and/or Benchling™.

Gene Drive Safety Measures

All crosses using gene drives genetics were performed in accordance to an Institutional Biosafety Committee-approved protocol from UCSD in which full gene-drive experiments are performed in a high-security ACL2 barrier facility and split drive experiments are performed in an ACL1 insectary in plastic vials that are autoclaved prior to being discarded in accord with currently suggested guidelines for laboratory confinement of gene-drive systems (Akbari et al. 2015; National Academies of Sciences, Engineering, and Medicine et al. 2016).

TABLE 1

Primers used in this study.

| Primer | Primer Sequence, 5' to 3' | Source |
|---|---|---|
| attP sequence<br>986.C1<br>986.C2 | CCCACAATGGTTAATTCGAGCTCGCCCGGGTCCTAGG<br>TCGACGATGTAGGTCACGGTCTC (SEQ ID NO: 1)<br>GTTATTTTAAAAACGATTCATTCTAGTTAATTAAGTC<br>GACATGCCCGCCGTGACCGTCGA (SEQ ID NO: 2) | plasmid M{3xP3-RFP attP} |
| p10 3'UTR<br>986.C3<br>986.C4 | TCGACGGTCACGGCGGGCATGTCGACTTAATTAACTA<br>GAATGAATCGTTTTTAAAATAAC (SEQ ID NO: 3)<br>AAAAGTTGGTGGTGGGGAGGCCACCGAGTATGGGCG<br>CGCCCCGGCCGTTAACTCGAATCG (SEQ ID NO: 4) | Addgene plasmid #100580 |
| opie2 promoter fragment<br>986.C5<br>986.C6 | GCTGGCTTGGATAGCGATTCGAGTTAACGGCCGGGG<br>CGCGCCCATACTCGGTGGCCTCCC (SEQ ID NO: 5)<br>CCCCGGTGAACAGCTCCTCGCCCTTGCTCACCATCTC<br>GAGCACCAGAGACAGGTTGCGGC (SEQ ID NO: 6) | Translocation plasmid B |
| eCFP<br>986.C7<br>986.C8 | CGCCATCCAACCGCCGCCGCAACCTGTCTCTGGTGCT<br>CGAGATGGTGAGCAAGGGCGAGG (SEQ ID NO: 7)<br>GTGGTATGGCTGATTATGATCTAGAGTCGCGGCCGCT<br>TACTTGTACAGCTCGTCCATGCC (SEQ ID NO: 8) | pJFRC81-10XUAS-IVS-Syn21-GFP-p10 |
| Ubiquitin-63E promoter fragment (for 986B)<br>986.C9<br>986.C10 | AGCGGGTTCTCGACGGTCACGGCGGGCATGTCGACG<br>CGGCCGCCGCGCAGATCGCCGATG (SEQ ID NO: 9)<br>CAATGGAGTACTTCTTGTCCATGGTGGCAGTTTAAAC<br>TCTGCGGGTCAAAATAGAGATGT (SEQ ID NO: 10) | *D. melanogaster* genomic DNA |
| dCas9-VPR (for 986B)<br>986.C11<br>986.C12 | ATTTTCCACATCTCTATTTTGACCCGCAGAGTTTAAA<br>CTGCCACCATGGACAAGAAGTAC (SEQ ID NO: 11)<br>ATTGATTTGTTATTTTAAAAACGATTCATTCTAGTTAA<br>TTAATCAAAACAGAGATGTGTC (SEQ ID NO: 12) | Addgene plasmid #78898 |
| bottleneck promoter fragment (for | GCGGGTTCTCGACGGTCACGGCGGGCATGTCGACGC<br>GGCCGCATTAGATGAACCCCATGG (SEQ ID NO: 13)<br>CCCAATGGAGTACTTCTTGTCCATGGTGGCAGTTTAA | *D. melanogaster* genomic DNA |

TABLE 1-continued

Primers used in this study.

| Primer | Primer Sequence, 5' to 3' | Source |
|---|---|---|
| 986C) 986.C13 986.C14 | ACAGCCGAATTCGTTGACGGTTG (SEQ ID NO: 14) | |
| dCas9-VPR (for 986C) 986.C15 986.C12 | TTCGTACTTCAACCGTCAACGAATTCGGCTGTTTAAA CTGCCACCATGGACAAGAAGTAC (SEQ ID NO: 15) ATTGATTTGTTATTTTAAAAACGATTCATTCTAGTTAA TTAATCAAAACAGAGATGTGTC (SEQ ID NO: 16) | Addgene plasmid #78898 |
| Ubiquitin-63E promoter fragment (for 986D) 986.C9 986.C16 | AGCGGGTTCTCGACGGTCACGGCGGGCATGTCGACG CGGCCGCCGCGCAGATCGCCGATG (SEQ ID NO: 17) TCGTGGCCGCCGGCCTTTTCATGGTGGCAGTTTAAAC TCTGCGGGTCAAAATAGAGATGT (SEQ ID NO: 18) | *D. melanogaster* genomic DNA |
| dCas9-VP64 (for 986D) 986.C17 986.C18 | TTCCACATCTCTATTTTGACCCGCAGAGTTTAAACTG CCACCATGAAAAGGCCGGCGGCC (SEQ ID NO: 19) ATTGATTTGTTATTTTAAAAACGATTCATTCTAGTTAA TTAATTAGCCCTCCCACACATA (SEQ ID NO: 20) | Addgene plasmid #78897 |
| bottleneck promoter fragment (for 986E) 986.C13 986.C19 | GCGGGTTCTCGACGGTCACGGCGGGCATGTCGACGC GGCCGCATTAGATGAACCCCATGG (SEQ ID NO: 21) TTTCGTGGCCGCCGGCCTTTTCATGGTGGCAGTTTAA ACAGCCGAATTCGTTGACGGTTG (SEQ ID NO: 22) | *D. melanogaster* genomic DNA |
| dCas9-VP64 (for 986E) 986.C20 986.C18 | GTACTTCAACCGTCAACGAATTCGGCTGTTTAAACTG CCACCATGAAAAGGCCGGCGGCC (SEQ ID NO: 23) ATTGATTTGTTATTTTAAAAACGATTCATTCTAGTTAA TTAATCAAAACAGAGATGTGTC (SEQ ID NO: 24) | Addgene plasmid #78897 |
| U6:3 promoter fragment 1045.C1 1045.C2 | TTGGGAATTGGGCAATATTTAAATGGCGGCGCGCCG AATTCTTTTTTGCTCACCTGTGAT (SEQ ID NO: 25) CTTATTTTAACTTGCTATTTCTAGCTCTAAAACCCTAG GCCGACGTTAAATTGAAAATAG (SEQ ID NO: 26) | Addgene plasmid #49411 |
| sgRNA scaffold 1045.C3 1045.C4 | ATATATAGACCTATTTTCAATTTAACGTCGGCCTAGG GTTTTAGAGCTAGAAATAGCAAG (SEQ ID NO: 27) AGTGGATCTCTAGAGGTACCGTTGCGGCCGCGTTTTA ATTAAAAAAGCACCGACTCGGTG (SEQ ID NO: 28) | Addgene plasmid #49411 |
| eve-sgRNA-U6:1-promoter-hid-sgRNA fragment 1045.C5 1045.C6 | GTTCGTATATATAGACCTATTTTCAATTTAACGTCGG ATCGTGCGGTGCTGAGAG (SEQ ID NO: 29) CGGACTAGCCTTATTTTAACTTGCTATTTCTAGCTCTA AAACTCATGCACGTGCATGTGC (SEQ ID NO: 30) | Custom gBlocks ® Gene Fragment |
| Gypsy-U6:1-promoter-hh1-sgRNA-U6:3-promoter-hh2-sgRNA fragment (for OA-1045B) 1045.C7 1045.C8 | GGTGCTTTTTTAATTAAAACGCGGCCGCAACGGTACC TGCAGCCACGTAATAAGTGTGCG (SEQ ID NO: 31) ACACTAGTGGATCTCTAGAACAACTCTCAGGCTCCAG GTAGGCAAAAAAGCACCGACTCG (SEQ ID NO: 32) | pCFD-hh |
| Gypsy-U6:1-promoter-wg1-sgRNA-U6:3-promoter-wg2-sgRNA fragment (for OA-1045C) 1045.C7 1045.C8 | GGTGCTTTTTTAATTAAAACGCGGCCGCAACGGTACC TGCAGCCACGTAATAAGTGTGCG (SEQ ID NO: 33) ACACTAGTGGATCTCTAGAACAACTCTCAGGCTCCAG GTAGGCAAAAAAGCACCGACTCG (SEQ ID NO: 34) | pCFD-wg |
| U6:1-promoter-wg1-sgRNA-U6:3-promoter-wg2-sgRNA fragment (for OA-1045D) 1045.C9 1045.C10 | CCGGGAATTGGGAATTGGGCAATATTTAAATGGCGG CGCGCCAGCCGATCAATTGAGATC (SEQ ID NO: 35) TGTTTTTGCGAATAAATTCAACGCACACTTATTACGT GCATATGAACAACTCTCAGGCTC (SEQ ID NO: 36) | pCFD-wg |

TABLE 1-continued

| Primers used in this study. | | |
|---|---|---|
| Primer | Primer Sequence, 5' to 3' | Source |
| Gypsy-U6:1-promoter-hh1-sgRNA-U6:3-promoter-hh2-sgRNA fragment (for OA-1045D) 1045.C11 1045.C12 | CTGGAGCCTGAGAGTTGTTCATATGCACGTAATAAGT GTGCGTTG (SEQ ID NO: 37) TTTATTGAACAACTCTCAGGCTCCAGGTAGTCTAGAG CAAAAAAGCACCGACTCGGTGCC (SEQ ID NO: 38) | pCFD-hh |
| tRNA-eve-sgRNA-tRNA-hid-sgRNA-RNA-hh1-sgRNA-tRNA-hh2-sgRNA-U6:3 UTR fragment (for OA-1045E) 1045.C13 1045.C14 | TCGTATATATAGACCTATTTTCAATTTAACGTCGGTT AATTAAGGGCTTTGAGTGTGTGT (SEQ ID NO: 39) TCGTCGACACTAGTGGATCTCTAGAGGTACCGTTGCG GCCGCATGCATACGCATTAAGCG (SEQ ID NO: 40) | Gene synthesized vector |

Example 1—Engineering Species

Figure 1C:
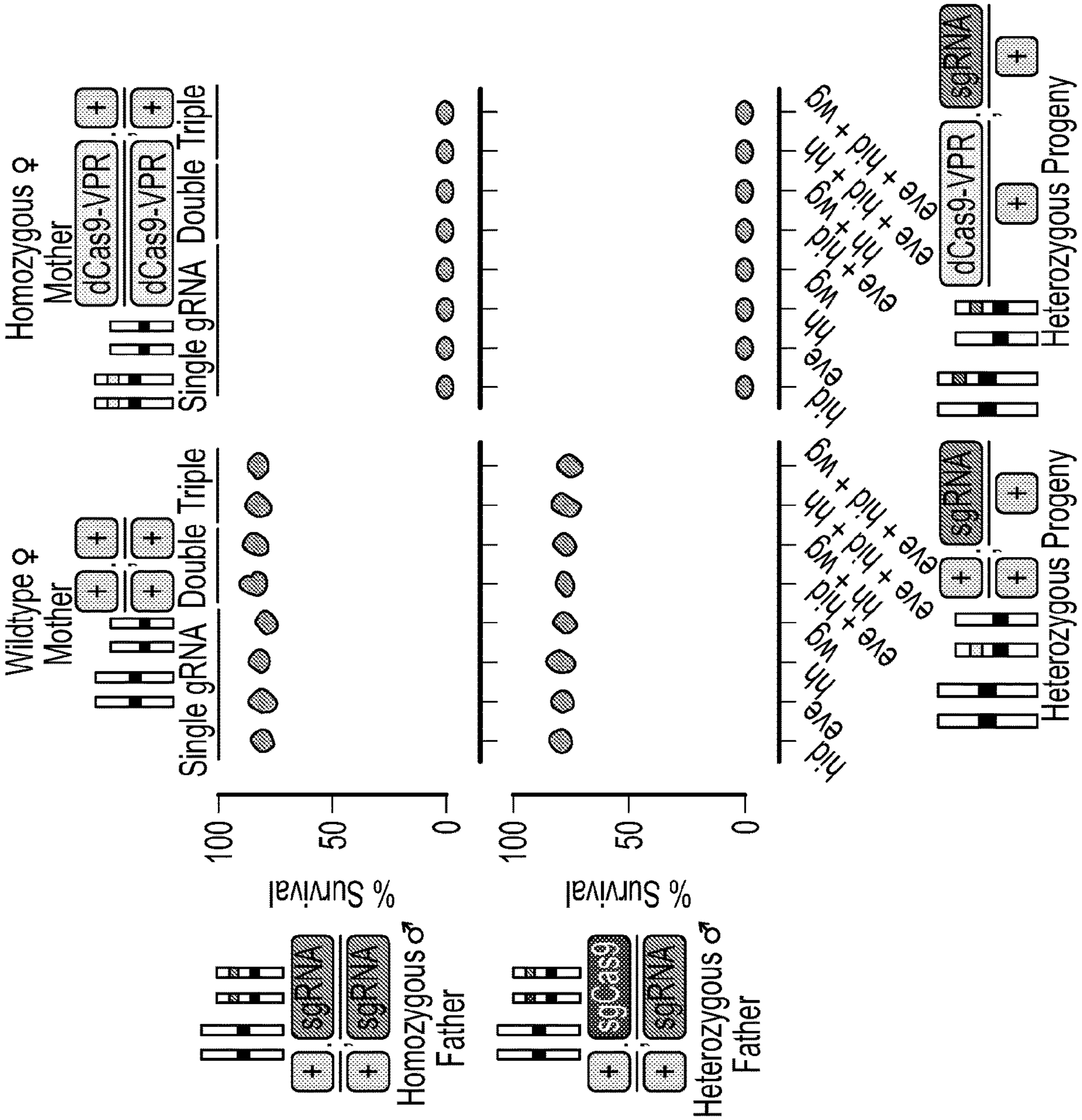
Figure 1D:
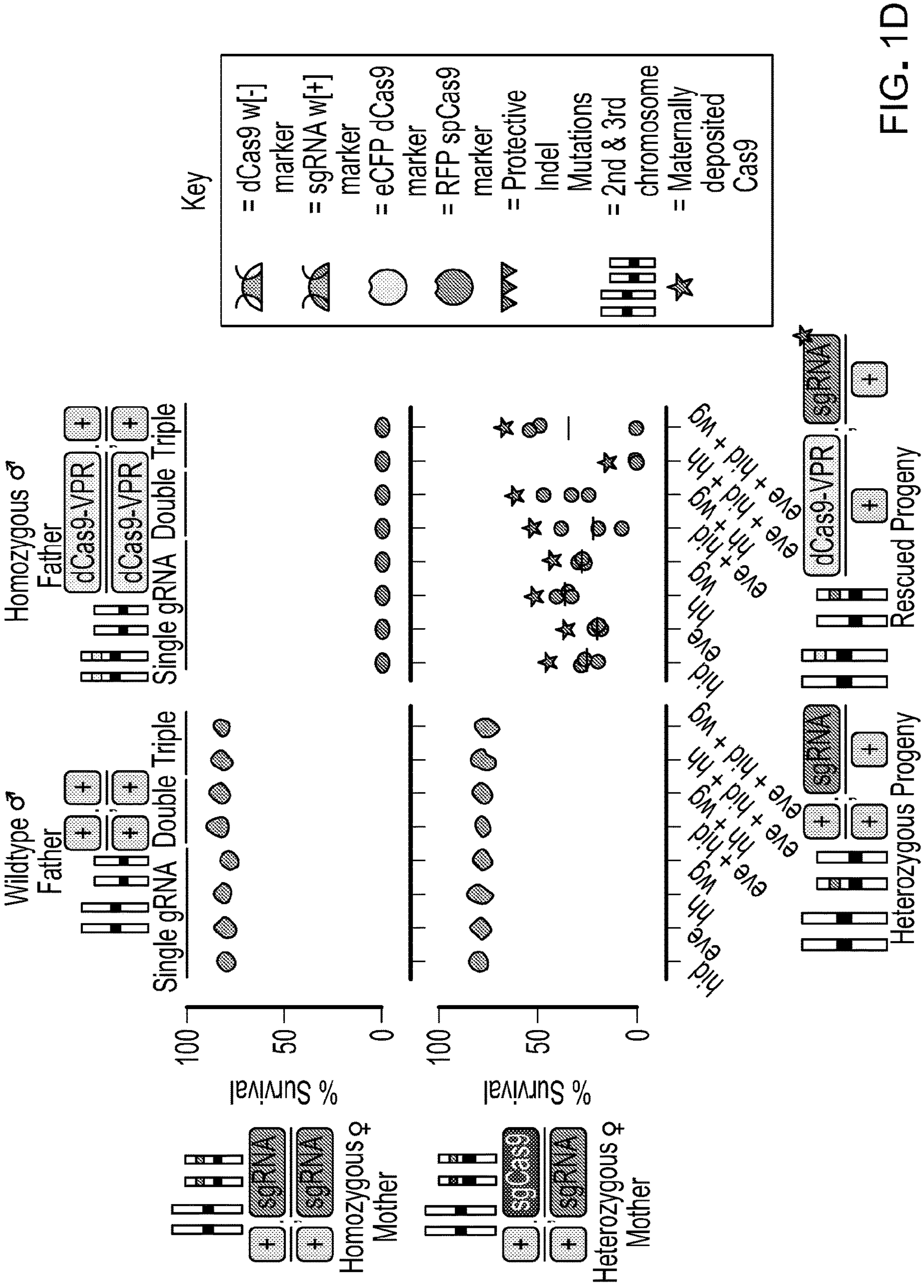

Flies expressing a dCas9 activator domain fusion (dCas9-VPR) were engineered and evaluated whether these transgenes could drive lethal target overexpression using CRISPRa sgRNA lines each targeting the promoter region of one of four important developmental genes (eve, hid, hh, and wg)(FIG. 7). Zygotic dCas9-VPR expression did not cause noticeable toxicity on its own and achieved 100% lethality in individuals also expressing sgRNAs targeting one of the target genes (FIG. 1B-1D). Interestingly, this lethality could only be rescued when homozygous dCas9-VPR-expressing fathers were crossed to heterozygous Cas9; sgRNA mothers (FIG. 1D). With this cross, mothers provided indel mutations in the promoter region of the target genes, while simultaneously depositing sgRNA/Cas9 into all embryos, which mutated the inherited paternal copy of the target sites.

Figure 8:
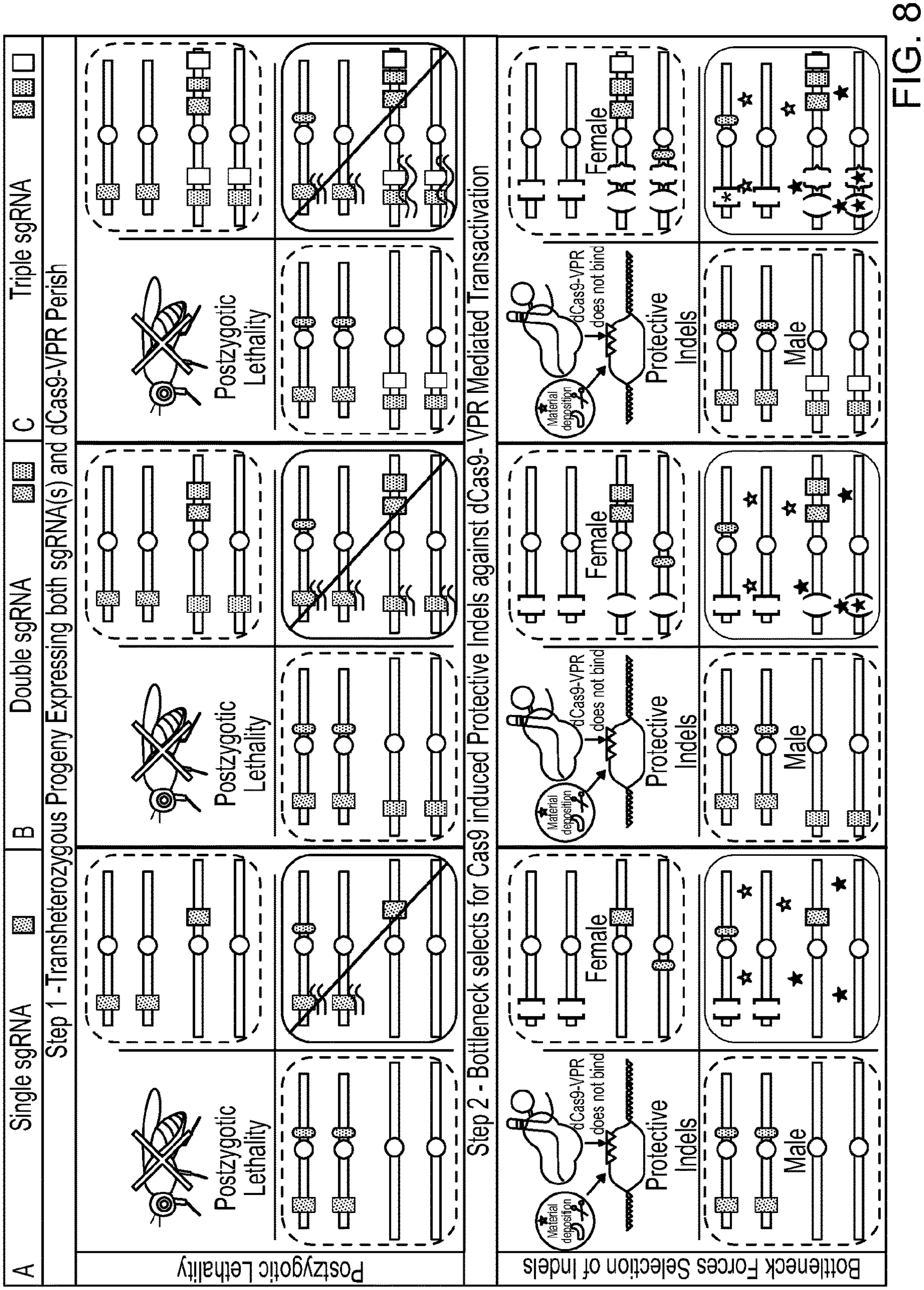
FIGS. 8A-8C shows a schematic of the genetic crossing scheme used to engineer SPECIES.
Figure 8:
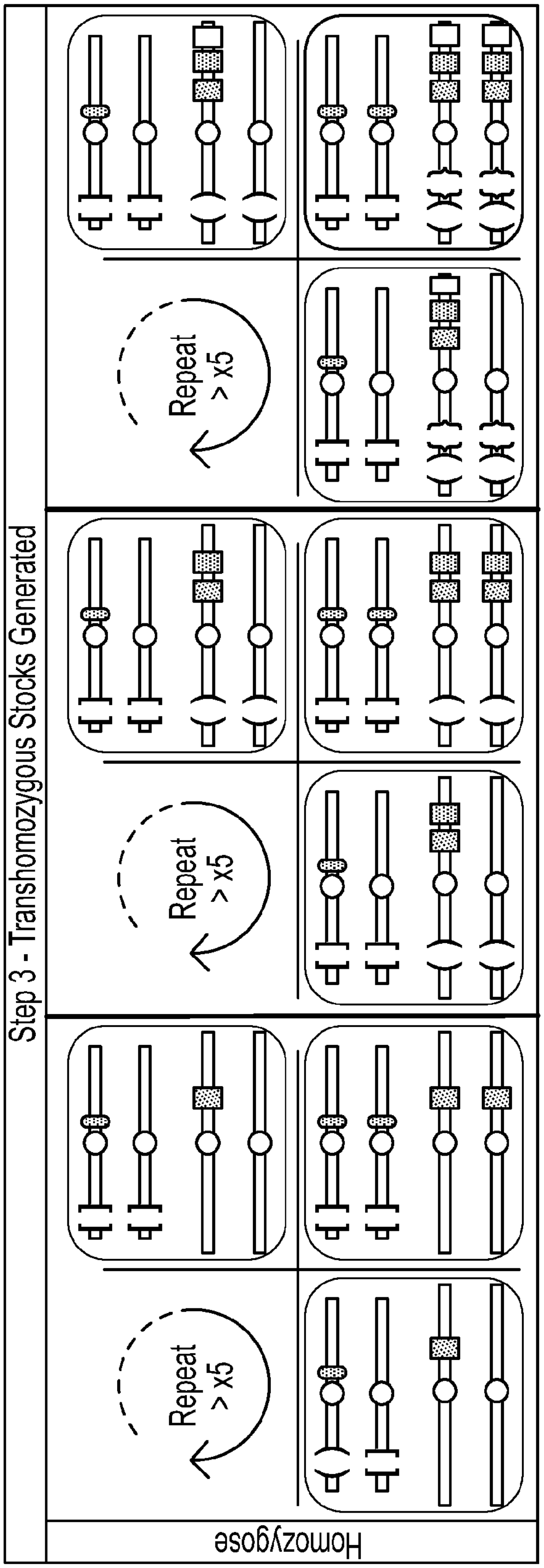
Figure 8:
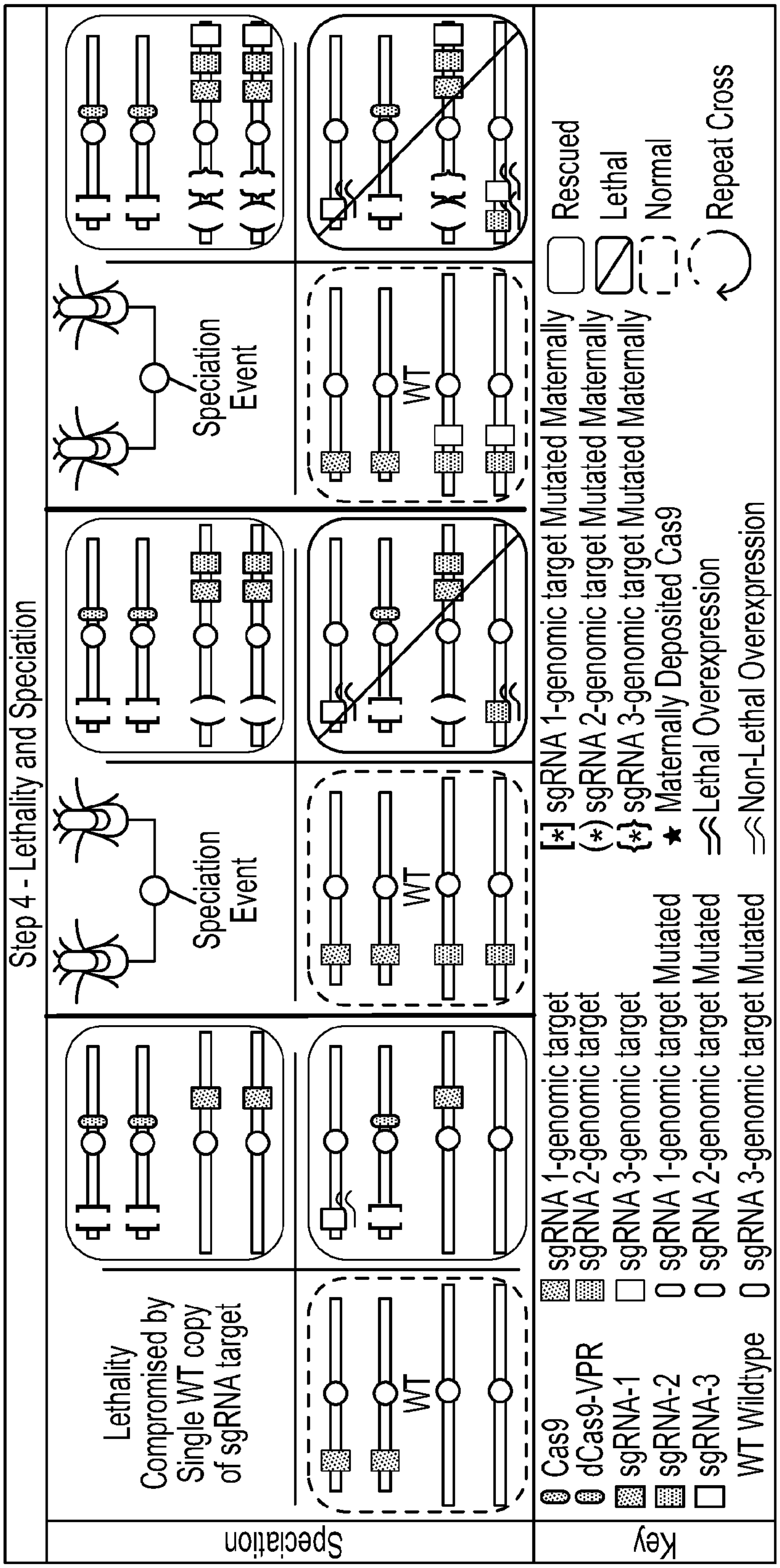

Importantly, the inherited sgRNA/dCas9-VPR transgenes forced a bottleneck that selected for protective indels which blocked CRISPRa-induced lethality and allowed for endogenous expression levels of the target gene, providing embryonic rescue and survival (FIG. 1C-1D and FIGS. 8A-8C). However, when homozygous dCas9-VPR/dCas9-VPR; sgRNA/sgRNA individuals harboring the protective indel mutations were outcrossed to WT, they produced some viable progeny, indicating that homozygous "rescued" flies were not 100% reproductively isolated from their WT counterparts (FIGS. 8A-8C).

To overcome the incomplete isolation from single-gene overexpression, multiplexed overexpression was tested by engineering flies that simultaneously expressed sgRNAs targeting two or more genes (eve+hid; eve+hid+hh; eve+hid+wg; and hh+wg; FIGS. 7, 8A-8C, 9). Crossing these to the dCas9-VPR flies resulted in complete progeny lethality (FIG. 1C, Table 4-5), suggesting that heterozygosity for a WT allele and an allele with a selected indel is lethal.

Figure 2A:
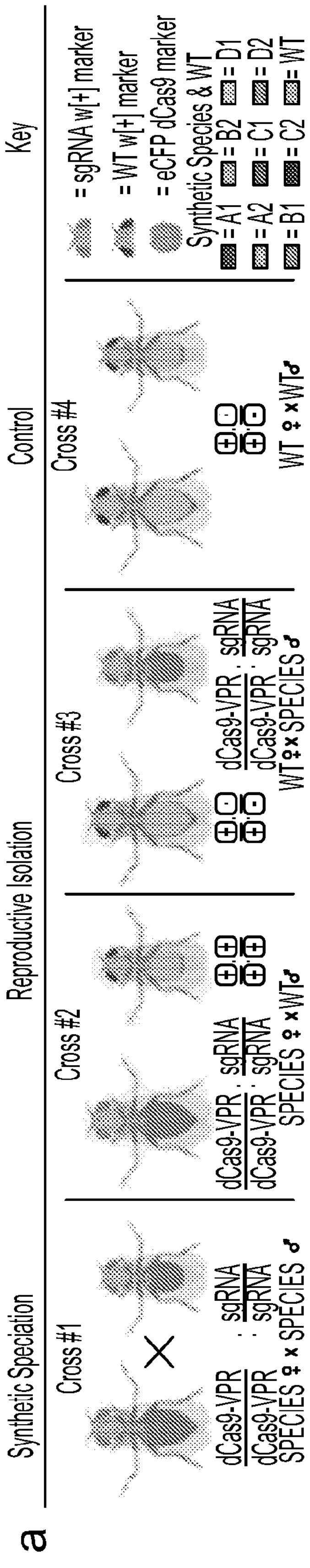
FIGS. 2A-2D shows embryo and adult viability determinations.
Figure 2B:
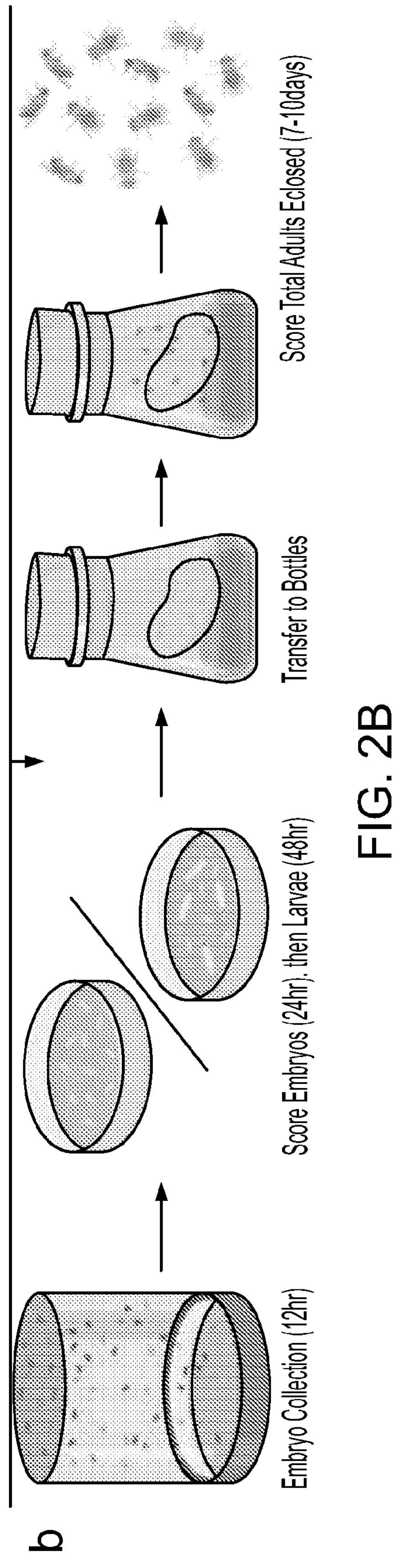
Figure 2C:
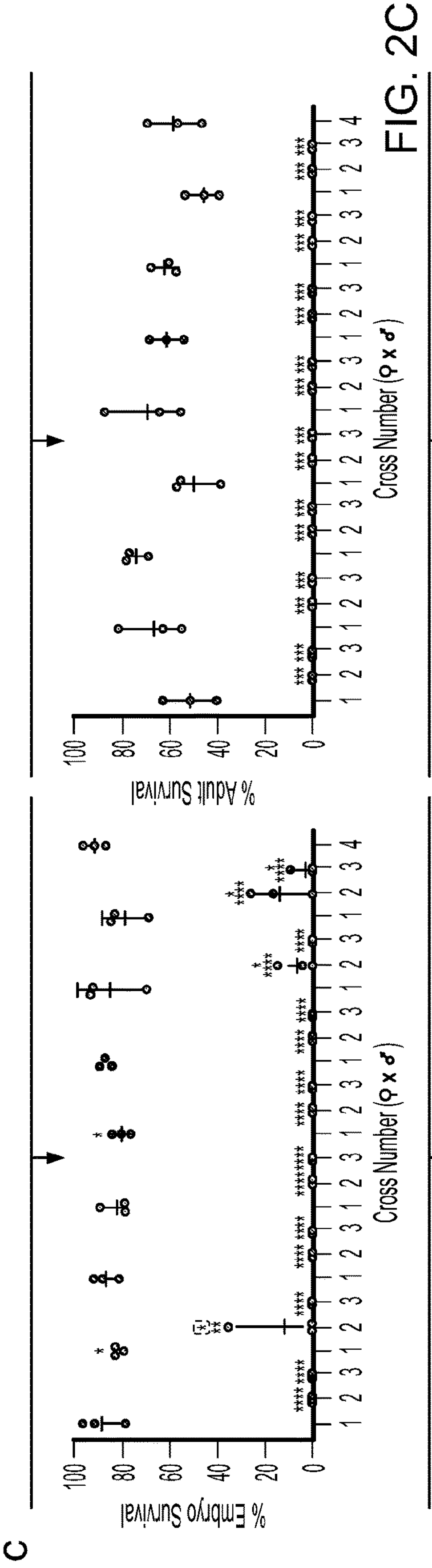
Figure 2D:
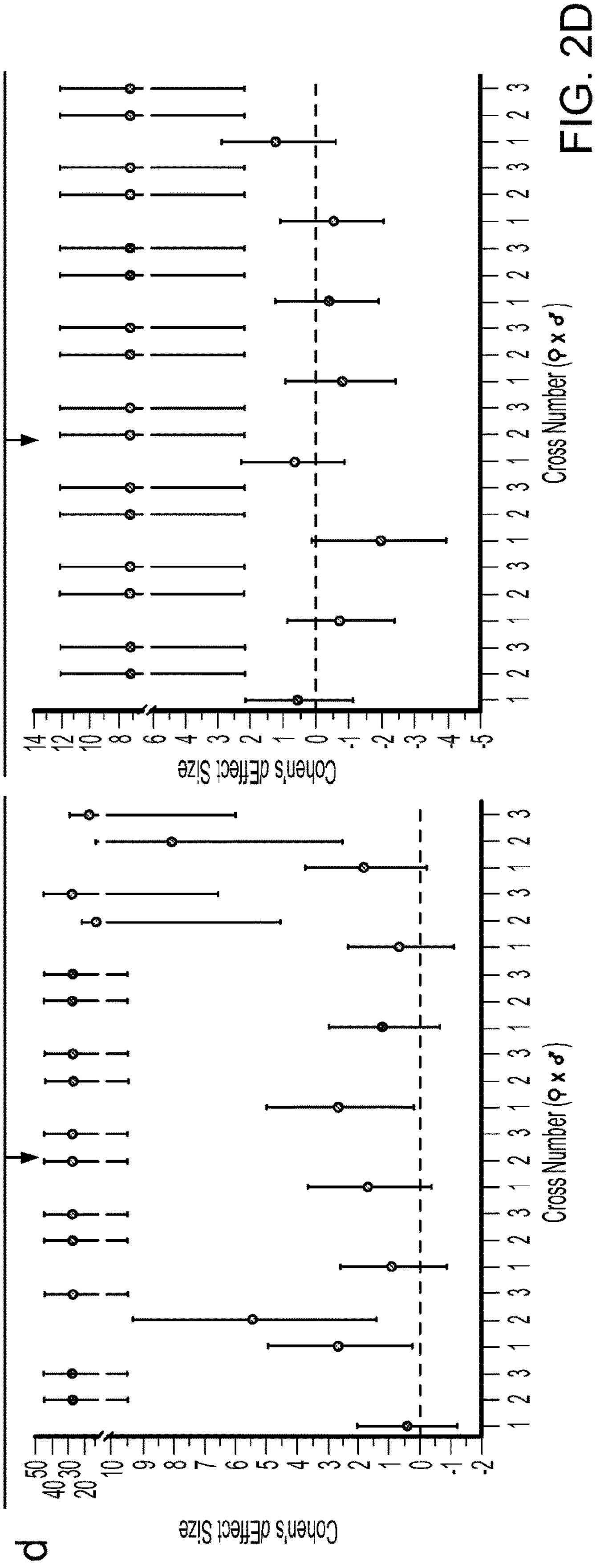

With the selective bottleneck genetic crossing scheme, crosses with multiplexed sgRNA/Cas9-expressing mothers rescued heterozygous dCas9; sgRNA animals through the introduction of indel mutations (FIG. 10). Some fitness costs can be seen, at least as inferred from fertility and survivorship, in many of the SPECIES strains (FIG. 2C). Moreover, in contrast to the single-target sgRNA lines, heterozygote progeny from homozygous dCas9-VPR; multiplexed sgRNA individuals crossed to WT were all lethal, suggesting that inheriting one WT copy of each target site from the WT parent ensured 100% lethality (FIGS. 8A-8C).

To generate reproductively isolated SPECIES, multiple generations (>5) of dCas9-VPR; sgRNA "rescued" individuals were intercrossed, resulting in homozygous stocks representing eight isolated SPECIES (A1-D2). Each SPECIES was reproductively incompatible with WT (FIGS. 8A-8C and 9) and harbored the expected indels at the target sites (FIG. 10). Bidirectional outcrosses of all eight SPECIES to WT, or to a different SPECIES with varying target genes, demonstrated 100% reproductive isolation, indicating the creation of several independent barriers to sexual reproduction (FIGS. 2A-2D and 11A-11B, Table 6). Additional crosses between SPECIES and genetically diverse stocks from five different continents also demonstrated 100% reproductive isolation.

Figure 3B:
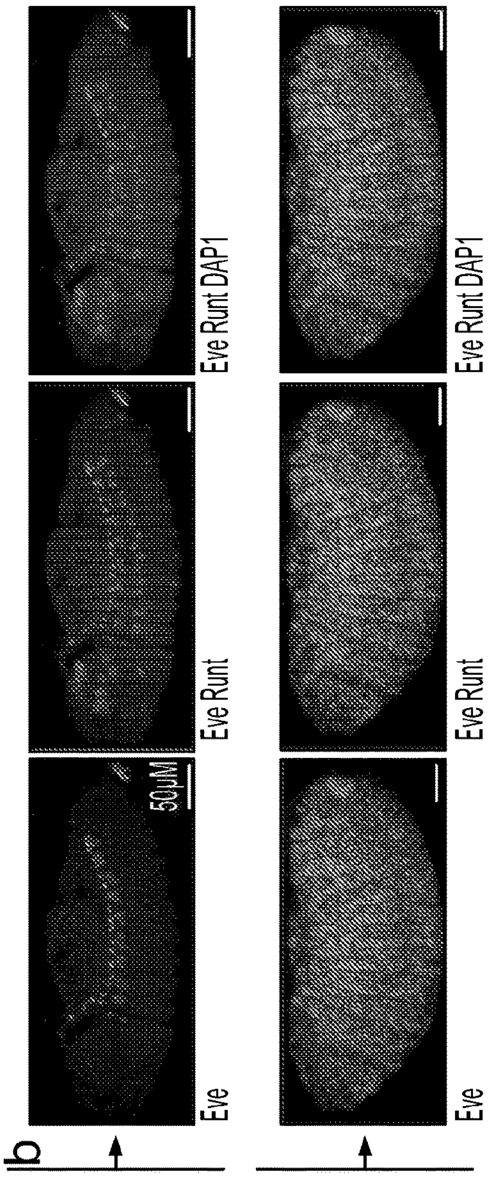
FIGS. 3A-3D show visualization and quantification of target gene overexpression.
Figure 3A:
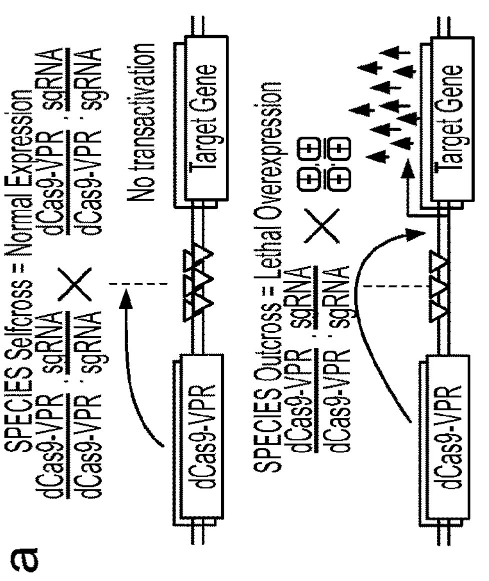
Figure 3C:
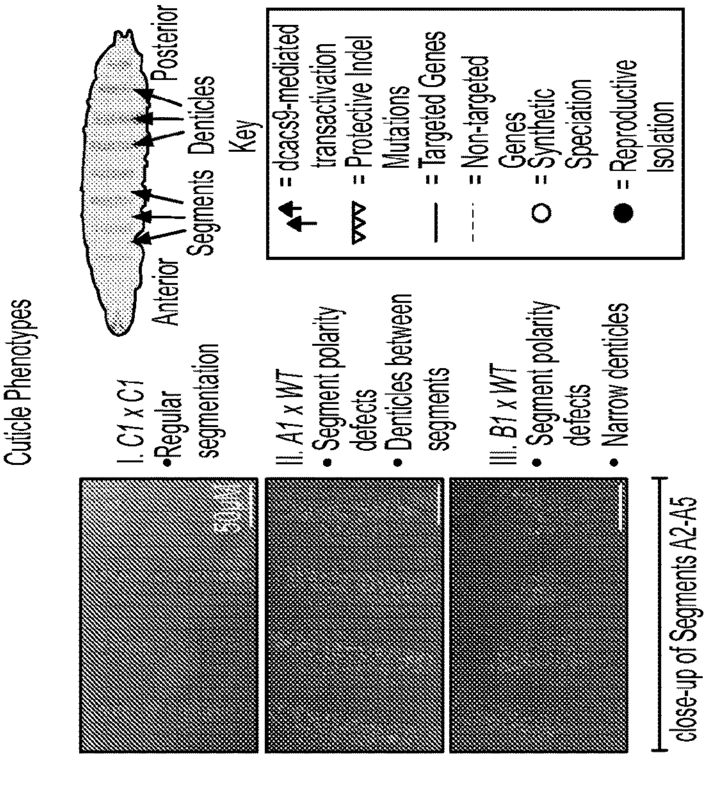
Figure 3D:
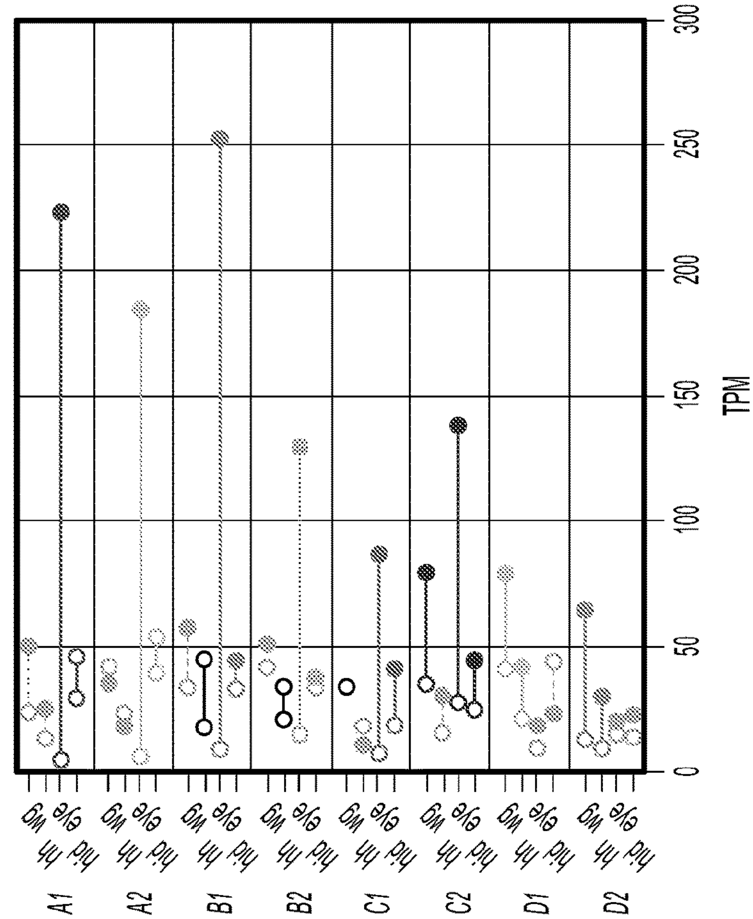

The extent of target gene overexpression was then determined when outcrossed to WT by visualizing overexpression in embryos via antibody stain, and the effect of misexpression on development was evaluated using cuticle preps of late embryos and young larvae. Target gene overexpression was observed at embryonic stages and segment polarity defects in larvae when the SPECIES lines were mated to WT but not when self-crossed (FIGS. 3A-3C). To quantify the extent of target gene overexpression and to measure possible global gene misexpression, transcriptome wide expression profiling was performed. RNA-expression profiles were quantified for all samples, including genes that were expressed from constructs described herein (FIG. 3D). From this analysis, it was found that significant target gene overexpression (up to 48-fold) in the progeny was generated from SPECIES and WT crosses but not in the progeny from SPECIES intercrosses (FIGS. 12A-12D and 13, Table 8-10).

Example 2—Population Replacement Via SPECIES Mediated Extreme Underdominance

To assess whether the SPECIES were capable of reversible WT population replacement via gene drive, population studies were conducted at various release thresholds employing one representative SPECIES, A1 (FIG. 4). Releases of A1 individuals at a population frequency of 70% resulted in this SPECIES replacing the WT population in two of six replicates (FIG. 4). Population replacement also occurred in three of four replicates of A1 releases at a frequency of 80% and in one of one replicate at a 90% release frequency. However, a release frequency of 50% resulted in elimination of the A1 strain in three of three replicates (FIG. 4).

To characterize the population dynamics observed in the population studies, a mathematical model was fitted to the observed data, incorporating a fitness cost for reproductively isolated individuals relative to WT individuals. The A1 strain was estimated to have a strong relative fitness cost of 34.84% (95% credible interval [CrI]: 34.82-34.87%), producing a threshold frequency of ~61%, which corresponds to what was observed in the population studies. Of the seven other SPECIES characterized, two consistently led to population replacement at a release frequency of 80% (A2 and D1), and three led to population replacement at a release frequency of 90% (A2, D1, and D2) (FIG. 4), with increased threshold frequencies corresponding to increased fitness costs for all SPECIES. This suggests that population replacement via gene drive would theoretically occur when the release of SPECIES individuals exceeded a critical threshold frequency in the population, the value of which depends on the fitness of the synthesized strain relative to the WT strain.

TABLE 2

Synthetic lethality with dCas9-A/dCas9-A crossed with sgRNA/sgRNA

| | | Homozygous sgRNA Target | | | | |
|---|---|---|---|---|---|---|
| | Wildtype | Hid (line 463) | Eve (line 464) | Hh (line 416) | Wg (line 417) | Upd2 (line 415) |
| Wildtype | 85/100, 87/100, 84/100 | 79/100, 82/100, 80/100 | 78/100, 81/100, 83/100 | 83/100, 81/100, 81/100 | 80/100, 77/100, 79/100 | 82/100, 80/100, 81/100 |
| 986C Male | 82/100, 84/100, 81/100 | 95/100; 83/100; 87/100 | 0/100; 0/100; 0/100 | 0/100; 0/100; 0/100 | 0/100; 0/100; 0/100 | 10/100; 15/100; 12/100 |
| 986D Male | 81/100, 78/100, 80/100 | 77/100, 79/100, 72/100 | 80/100, 76/100, 79/100 | 80/100, 75/100, 85/100 | 79/100, 82/100, 76/100 | 80/100, 77/100, 81/100 |
| 986E Male | 79/100, 81/100, 81/100 | 80/100, 80/100, 76/100 | 77/100, 79/100, 82/100 | 77/100, 81/100, 80/100 | 83/100, 72/100, 81/100 | 79/100, 78/100, 82/100 |
| 986C Female | 79/100, 81/100, 80/100 | 69/100; 68/100; 68/100 | 0/100; 0/100; 0/100 | 0/100; 0/100; 0/100 | 60/100; 82/100; 48/100 | 11/100; 17/100; 20/100 |

TABLE 2-continued

Synthetic lethality with dCas9-A/dCas9-A crossed with sgRNA/sgRNA

| | | Homozygous sgRNA Target | | | | |
|---|---|---|---|---|---|---|
| | Wildtype | Hid (line 463) | Eve (line 464) | Hh (line 416) | Wg (line 417) | Upd2 (line 415) |
| 986D Female | 76/100, 72/100, 79/100 | 78/100, 80/100, 76/100 | 75/100, 79/100, 82/100 | 76/100, 78/100, 78/100 | 80/100, 73/100, 79/100 | 81/100, 72/100, 78/100 |
| 986E Female | 77/100, 81/100, 79/100 | 76/100, 76/100, 79/100 | 80/100, 74/100, 76/100 | 69/100, 83/100, 79/100 | 75/100, 79/100, 80/100 | 81/100, 73/100, 78/100 |

TABLE 3

Rescue of synthethetic lethality with dCas9-A/dCas9-A crossed with Ubi-spCas9/sgRNA

| | Wildtype | Hid (line 463) | Eve (line 464) | Hh (line 416) | Wg (line 417) |
|---|---|---|---|---|---|
| Wildtype | 85/100, 87/100, 84/100 | 79/100, 82/100, 80/100 | 78/100, 81/100, 79/100 | 83/100, 81/100 77/100 | 80/100, 77/100, 79/100 |
| 986C Male | 82/100, 81/100, 84/100 | 29/100, 20/100, 27/100 | 18/100, 22/100, 19/100 | 41/100, 35/100, 33/100 | 30/100, 28/100, 26/100 |
| 986C Female | 79/100, 81/100, 80/100 | 0/100, 0/100, 0/100 | 0/100, 0/100, 0/100 | 0/100, 0/100, 0/100 | 0/100, 0/100, 0/100 |

TABLE 4

Synthetic lethality with dCas9-A/dCas9-A crossed with sgRNA/sgRNA

| | Wildtype | hid + eve (1045A) | hh + wg (1045D) | hid + eve + hh (1045B) | hid + eve + wg (1045C) | hid + eve + hh tRNA (1045E) |
|---|---|---|---|---|---|---|
| Wildtype | 85/100, 87/100, 84/100 | 82/100, 87/100, 82/100 | 81/100, 86/100, 83/100 | 80/100, 85/100, 83/100 | 82/100, 82/100, 84/100 | 85/100, 83/100, 79/100 |
| 986C Male | 81/100, 80/100, 83/100 | 0/100; 0/100; 0/100 | 0/100; 0/100; 0/100 | 0/100; 0/100; 0/100 | 0/100; 0/100; 0/100 | 75/100, 87/100, 72/100 |
| 986C Female | 79/100, 80/100, 78/100 | 0/100; 0/100; 0/100 | 0/100; 0/100; 0/100 | 0/100; 0/100; 0/100 | 0/100; 0/100; 0/100 | 71/100, 75/100, 81/100 |

TABLE 5

Rescue of synthetic lethality with dCas9-A/dCas9-A × Ubi-spCas9/sgRNA

| | Wildtype | hid + eve (1045A1) | hid + eve (1045A2) | hh + wg (1045D1) | hh + wg (1045D2) | hid + eve + hh (1045B1) | hid + eve + wg (1045C1) | hid + eve + hh tRNA (1045E) |
|---|---|---|---|---|---|---|---|---|
| Wildtype | 85/100, 87/100, 84/100 | 79/100, 78/100, 79/100 | | 80/100, 77/100, 79/100 | | 81/100, 75/100, 80/100 | 74/100, 77/100, 79/100 | 80/100, 78/100, 78/100 |
| 986C Male | 81/100, 80/100, 83/100 | 32/166, 32/82, 7/92 | 78/198, 26/108, 22/141 | 33/131, 52/108, 51/153 | 12/174, 19/121, 33/94 | 0/170, 5/304, 0/154 | 40/80, 64/116, 0/158 | N/A |
| 986C Female | 79/100, 80/100, 78/100 | 0/89, 0/115, 0/137 | 0/101, 0/107, 0/142 | 0/150, 0/99, 0/115 | 0/120, 0/162, 0/138 | 0/116, 0/160, 0/107 | 0/135, 0/201, 0/150 | N/A |

TABLE 6

Survival table for synthetic species.

| Parental Genotype ♀ | Parental Genotype ♂ | Embryo survival: Replicate One | Embryo survival: Replicate Two | Embryo survival: Replicate Three | Embryo survival: Replicate Four | Embryo survival: Predicted | Embryo survival: Observed | Total Larvae Observed | Total Surviving Larvae | n | p-value | Adult survival: Replicate One | Adult survival: Replicate Two | Adult survival: Replicate Three | Adult survival: Replicate Four | Adult survival: Predicted | Adult survival: Observed | n | p-value |
|---|---|---|---|---|---|---|---|---|---|---|---|---|---|---|---|---|---|---|---|
| A1 | A1 | 162/168 | 143/182 | 207/226 | 140/170 | 1 | 0.888643068 | 512 | N/A | 576 | 0.6651 | 103/162 | 58/143 | 107/207 | 67/140 | 1 | 0.519435029 | 512 | 0.5512 |
| A1 | OreR | 0/105 | 0/113 | 0/153 | 0/294 | 0 | 0 | 0 | 0 | 371 | <0.0001 | 0/0 | 0/0 | 0/0 | 0/0 | 0 | 0 | 0 | 0.0009 |
| OreR | A1 | 0/316 | 0/229 | 0/11 | 0/169 | 0 | 0 | 0 | 0 | 556 | <0.0001 | 0/0 | 0/0 | 0/0 | 0/0 | 0 | 0 | 0 | 0.0009 |
| A2 | A2 | 111/133 | 93/112 | 201/253 | 140/170 | 1 | 0.819803337 | 405 | N/A | 498 | 0.0322 | 62/111 | 77/93 | 127/201 | 131/140 | 1 | 0.672785448 | 405 | 0.4248 |
| A2 | OreR | 0/301 | 1/228 | 6/17 | 0/233 | 0 | 0.119109047 | 7* | 0 | 546 | 0.0027 | 0/0 | 0/1 | 0/6 | | 0 | 0 | 0 | 0.0009 |
| OreR | A2 | 0/402 | 0/228 | 0/83 | 0/298 | 0 | 0 | 0 | 0 | 713 | <0.0001 | 0/0 | 0/0 | 0/0 | | 0 | 0 | 0 | 0.0009 |
| B1 | B1 | 161/183 | 246/268 | 61/75 | 143/177 | 1 | 0.870341734 | 468 | N/A | 526 | 0.3217 | 125/161 | 171/246 | 48/61 | 133/143 | 1 | 0.752801571 | 468 | 0.0753 |
| B1 | OreR | 1/272 | 0/73 | 0/70 | 0/161 | 0 | 0.00122549 | 1* | 0 | 415 | <0.0001 | 0/1 | 0/0 | 0/0 | | 0 | 0 | 0 | 0.0009 |
| OreR | B1 | 0/638 | 0/126 | 0/169 | 0/139 | 0 | 0 | 0 | 0 | 933 | <0.0001 | 0/0 | 0/0 | 0/0 | | 0 | 0 | 0 | 0.0009 |
| B2 | B2 | 135/151 | 130/165 | 269/340 | 236/308 | 1 | 0.824364998 | 534 | N/A | 656 | 0.1054 | 52/135 | 73/130 | 155/269 | 133/236 | 1 | 0.507643942 | 534 | 0.4654 |
| B2 | OreR | 0/145 | 0/159 | 0/129 | 0/260 | 0 | 0 | 0 | 0 | 433 | <0.0001 | 0/0 | 0/0 | 0/0 | | 0 | 0 | 0 | 0.0009 |
| OreR | B2 | 0/316 | 0/259 | 0/397 | 0/286 | 0 | 0 | 0 | 0 | 972 | <0.0001 | 0/0 | 0/0 | 0/0 | | 0 | 0 | 0 | 0.0009 |
| C1 | C1 | 121/158 | 118/140 | 154/192 | 244/279 | 1 | 0.803587754 | 393 | N/A | 490 | 0.0325 | 107/121 | 91/140 | 86/154 | 184/244 | 1 | 0.697579693 | 415 | 0.3746 |
| C1 | OreR | 0/120 | 0/131 | 0/177 | 0/214 | 0 | 0 | 0 | 0 | 428 | <0.0001 | 0/0 | 0/0 | 0/0 | | 0 | 0 | 0 | 0.0009 |
| OreR | C1 | 0/171 | 0/223 | 0/51 | 0/211 | 0 | 0 | 0 | 0 | 445 | <0.0001 | 0/0 | 0/0 | 0/0 | | 0 | 0 | 0 | 0.0009 |
| C2 | C2 | 136/152 | 88/104 | 138/158 | 132/243 | 1 | 0.871436137 | 362 | N/A | 414 | 0.2146 | 74/136 | 61/88 | 85/138 | 82/132 | 1 | 0.617747165 | 362 | 0.6602 |
| C2 | OreR | 0/96 | 0/284 | 0/183 | 0/257 | 0 | 0 | 0 | 0 | 563 | <0.0001 | 0/0 | 0/0 | 0/0 | | 0 | 0 | 0 | 0.0009 |
| OreR | C2 | 0/309 | 0/152 | 0/216 | 0/231 | 0 | 0 | 0 | 0 | 677 | <0.0001 | 0/0 | 0/0 | 0/0 | | 0 | 0 | 0 | 0.0009 |
| D1 | D1 | 258/279 | 76/109 | 42/45 | 178/195 | 1 | 0.851770741 | 376 | N/A | 433 | 0.4733 | 158/258 | 44/76 | 29/42 | 123/178 | 1 | 0.627275553 | 376 | 0.56 |
| D1 | OreR | 0/368 | 17/114 | 13/294 | 0/224 | 0 | 0.064446831 | 30* | 0 | 776 | <0.0001 | 0/0 | 0/17 | 0/13 | | 0 | 0 | 0 | 0.0009 |
| OreR | D1 | 0/144 | 0/178 | 0/127 | 0/256 | 0 | 0 | 0 | 0 | 449 | <0.0001 | 0/0 | 0/0 | 0/0 | | 0 | 0 | 0 | 0.0009 |
| D2 | D2 | 169/199 | 196/284 | 148/178 | 157/234 | 1 | 0.790282583 | 513 | N/A | 661 | 0.0919 | 67/169 | 90/196 | 79/148 | 76/234 | 1 | 0.463139054 | 513 | 0.2031 |
| D2 | OreR | 0/291 | 10/61 | 66/262 | 0/153 | 0 | 0.138614274 | 76* | 0 | 614 | 0.0006 | 0/0 | 0/10 | 0/66 | | 0 | 0 | 0 | 0.0009 |
| OreR | D2 | 11/119 | 0/228 | 0/195 | 0/284 | 0 | 0.030812325 | 11* | 0 | 542 | <0.0001 | 0/11 | 0/0 | 0/0 | | 0 | 0 | 0 | 0.0009 |
| OreR | OreR | 422/486 | 77/80 | 68/74 | | 1 | 0.916577225 | 567 | N/A | 640 | N/A | 295/422 | 44/77 | 32/68 | | 1 | 0.580356313 | 567 | N/A |
| Normalized Data | | | | | | | | | | | | | | | | | | | |
| A1 | A1 | 162/168 | 143/182 | 207/226 | | 1 | 0.9695234 | 512 | N/A | 576 | 0.6651 | 103/162 | 58/143 | 107/207 | | 1 | 0.895027791 | 512 | 0.5512 |
| A1 | OreR | 0/105 | 0/113 | 0/153 | | 0 | 0 | 0 | 0 | 371 | <0.0001 | 0/0 | 0/0 | 0/0 | | 0 | 0 | 0 | 0.0009 |
| OreR | A1 | 0/316 | 0/229 | 0/11 | | 0 | 0 | 0 | 0 | 556 | <0.0001 | 0/0 | 0/0 | 0/0 | | 0 | 0 | 0 | 0.0009 |
| A2 | A2 | 111/133 | 93/112 | 201/253 | | 1 | 0.894418184 | 405 | N/A | 498 | 0.0322 | 62/111 | 77/93 | 127/201 | | 1 | 1.159262737 | 405 | 0.4248 |
| A2 | OreR | 0/301 | 1/228 | 6/17 | | 0 | 0.129949822 | 7* | 0 | 546 | 0.0027 | 0/0 | 0/1 | 0/6 | | 0 | 0 | 0 | 0.0009 |
| OreR | A2 | 0/402 | 0/228 | 0/83 | | 0 | 0 | 0 | 0 | 713 | <0.0001 | 0/0 | 0/0 | 0/0 | | 0 | 0 | 0 | 0.0009 |
| B1 | B1 | 161/183 | 246/268 | 61/75 | | 1 | 0.94955636 | 468 | N/A | 526 | 0.3217 | 125/161 | 171/246 | 48/61 | | 1 | 1.297136869 | 468 | 0.0753 |
| B1 | OreR | 1/272 | 0/73 | 0/70 | | 0 | 0.001337029 | 1* | 0 | 415 | <0.0001 | 0/1 | 0/0 | 0/0 | | 0 | 0 | 0 | 0.0009 |
| OreR | B1 | 0/638 | 0/126 | 0/169 | | 0 | 0 | 0 | 0 | 933 | <0.0001 | 0/0 | 0/0 | 0/0 | | 0 | 0 | 0 | 0.0009 |
| B2 | B2 | 135/151 | 130/165 | 269/340 | | 1 | 0.899395026 | 534 | N/A | 656 | 0.1054 | 52/135 | 73/130 | 155/269 | | 1 | 0.874710812 | 534 | 0.4654 |
| B2 | OreR | 0/145 | 0/159 | 0/129 | | 0 | 0 | 0 | 0 | 433 | <0.0001 | 0/0 | 0/0 | 0/0 | | 0 | 0 | 0 | 0.0009 |
| OreR | B2 | 0/316 | 0/259 | 0/397 | | 0 | 0 | 0 | 0 | 972 | <0.0001 | 0/0 | 0/0 | 0/0 | | 0 | 0 | 0 | 0.0009 |
| C1 | C1 | 121/158 | 118/140 | 154/192 | | 1 | 0.87672673 | 393 | N/A | 490 | 0.0325 | 107/121 | 91/140 | 86/154 | | 1 | 1.20198519 | 415 | 0.3746 |
| C1 | OreR | 0/120 | 0/131 | 0/177 | | 0 | 0 | 0 | 0 | 428 | <0.0001 | 0/0 | 0/0 | 0/0 | | 0 | 0 | 0 | 0.0009 |

TABLE 6-continued

Survival table for synthetic species.

| Parental Genotype ♀ | ♂ | Embryo survival: Replicate One | Replicate Two | Replicate Three | Replicate Four | Predicted | Observed | Total Larvae Observed | Total Surviving Larvae | n | p-value | Adult survival: Replicate One | Replicate Two | Replicate Three | Replicate Four | Predicted | Observed | n | p-value |
|---|---|---|---|---|---|---|---|---|---|---|---|---|---|---|---|---|---|---|---|
| OreR | C1 | 0/171 | 0/223 | 0/51 | | 0 | 0 | 0 | 0 | 445 | <0.0001 | 0/0 | 0/0 | 0/0 | | 0 | 0 | 0 | 0.0009 |
| C2 | C2 | 136/152 | 88/104 | 138/158 | | 1 | 0.95075037 | 362 | N/A | 414 | 0.2146 | 74/136 | 61/88 | 85/138 | | 1 | 1.064427406 | 362 | 0.6602 |
| C2 | OreR | 0/96 | 0/284 | 0/183 | | 0 | 0 | 0 | 0 | 563 | <0.0001 | 0/0 | 0/0 | 0/0 | | 0 | 0 | 0 | 0.0009 |
| OreR | C2 | 0/309 | 0/152 | 0/216 | | 0 | 0 | 0 | 0 | 677 | <0.0001 | 0/0 | 0/0 | 0/0 | | 0 | 0 | 0 | 0.0009 |
| D1 | D1 | 258/279 | 76/109 | 42/45 | | 1 | 0.929295118 | 376 | N/A | 433 | 0.4733 | 158/258 | 44/76 | 29/42 | | 1 | 1.080845575 | 376 | 0.56 |
| D1 | OreR | 0/368 | 17/114 | 13/294 | | 0 | 0.070312495 | 30* | 0 | 776 | <0.0001 | 0/0 | 0/17 | 0/13 | | 0 | 0 | 0 | 0.0009 |
| OreR | D1 | 0/144 | 0/178 | 0/127 | | 0 | 0 | 0 | 0 | 449 | <0.0001 | 0/0 | 0/0 | 0/0 | | 0 | 0 | 0 | 0.0009 |
| D2 | D2 | 169/199 | 196/284 | 148/178 | | 1 | 0.862210583 | 513 | N/A | 661 | 0.0919 | 67/169 | 90/196 | 79/148 | | 1 | 0.798025357 | 513 | 0.2031 |
| D2 | OreR | 0/291 | 10/61 | 66/262 | | 0 | 0.151230328 | 76* | 0 | 614 | 0.0006 | 0/0 | 0/10 | 0/66 | | 0 | 0 | 0 | 0.0009 |
| OreR | D2 | 11/119 | 0/228 | 0/195 | | 0 | 0.033616725 | 11* | 0 | 542 | <0.0001 | 0/11 | 0/0 | 0/0 | | 0 | 0 | 0 | 0.0009 |
| OreR | OreR | 422/486 | 77/80 | 68/74 | | 1 | 0.916577225 | 567 | N/A | 640 | N/A | 295/422 | 44/77 | 32/68 | | 1 | 0.580356313 | 567 | N/A |

Key

| Shorthand ID | Stock Description |
|---|---|
| WT | Wildtype (OreR) |
| A1 | Rescue line 986C/9732 1045A |
| A2 | Rescue line 986C/8622 1045A |
| B1 | Rescue line 986C/9732 1045B |
| C1 | Rescue line 986C/9732 1045C |
| D1 | Rescue line 986C/8622 1045D |
| D2 | Rescue line 986C/86Fa 1045D |

TABLE 7

Interspecies crosses.

| Parental Genotype | | Embryo Counts | | | | Embryo Survival to Adult | | | | | |
|---|---|---|---|---|---|---|---|---|---|---|---|
| ♀ | ♂ | Rep. | Rep. 2 | Rep. 3 | n | Rep. 1 | Rep. 2 | Rep. 3 | Predicted | Observed | n |
| A1 | A2 | 241 | 177 | 136 | 554 | 230 | 146 | 118 | 0 | 0.8822876 | 494 |
| A1 | B1 | 227 | 99 | 159 | 485 | 0 | 0 | 0 | 0 | 0 | 0 |
| A1 | B2 | 180 | 172 | 61 | 413 | 0 | 0 | 0 | 0 | 0 | 0 |
| A1 | C1 | 124 | 187 | 162 | 473 | 0 | 0 | 0 | 0 | 0 | 0 |
| A1 | C2 | 207 | 140 | 166 | 513 | 0 | 0 | 0 | 0 | 0 | 0 |
| A1 | D1 | 192 | 109 | 274 | 575 | 0 | 0 | 0 | 0 | 0 | 0 |
| A1 | D2 | 173 | 242 | 134 | 549 | 0 | 0 | 0 | 0 | 0 | 0 |
| A2 | A1 | 68 | 277 | 199 | 544 | 42 | 196 | 123 | 0 | 0.6477729 | 361 |
| A2 | B1 | 126 | 275 | 126 | 527 | 0 | 0 | 0 | 0 | 0 | 0 |
| A2 | B2 | 148 | 305 | 256 | 709 | 0 | 0 | 0 | 0 | 0 | 0 |
| A2 | C1 | 173 | 234 | 231 | 638 | 0 | 0 | 0 | 0 | 0 | 0 |
| A2 | C2 | 292 | 116 | 232 | 640 | 0 | 0 | 0 | 0 | 0 | 0 |
| A2 | D1 | 132 | 198 | 88 | 418 | 0 | 0 | 0 | 0 | 0 | 0 |
| A2 | D2 | 133 | 206 | 106 | 445 | 0 | 0 | 0 | 0 | 0 | 0 |
| B1 | A1 | 67 | 237 | 136 | 440 | 0 | 0 | 0 | 0 | 0 | 0 |
| B1 | A2 | 192 | 128 | 86 | 406 | 0 | 0 | 0 | 0 | 0 | 0 |
| B1 | B2 | 225 | 336 | 255 | 816 | 121 | 148 | 145 | 0 | 0.5156271 | 414 |
| B1 | C1 | 145 | 92 | 236 | 473 | 0 | 0 | 0 | 0 | 0 | 0 |
| B1 | C2 | 283 | 194 | 174 | 651 | 0 | 0 | 0 | 0 | 0 | 0 |
| B1 | D1 | 122 | 73 | 193 | 388 | 0 | 0 | 0 | 0 | 0 | 0 |
| B1 | D2 | 53 | 280 | 190 | 523 | 0 | 0 | 0 | 0 | 0 | 0 |
| B2 | A1 | 240 | 255 | 126 | 621 | 0 | 0 | 0 | 0 | 0 | 0 |
| B2 | A2 | 106 | 206 | 135 | 447 | 0 | 0 | 0 | 0 | 0 | 0 |
| B2 | B1 | 286 | 214 | 70 | 570 | 97 | 72 | 15 | 0 | 0.2966317 | 184 |
| B2 | C1 | 224 | 229 | 131 | 584 | 0 | 0 | 0 | 0 | 0 | 0 |
| B2 | C2 | 94 | 161 | 132 | 387 | 0 | 0 | 0 | 0 | 0 | 0 |
| B2 | D1 | 133 | 192 | 101 | 426 | 0 | 0 | 0 | 0 | 0 | 0 |
| B2 | D2 | 165 | 200 | 206 | 571 | 0 | 0 | 0 | 0 | 0 | 0 |
| C1 | A1 | 225 | 213 | 185 | 623 | 0 | 0 | 0 | 0 | 0 | 0 |
| C1 | A2 | 220 | 207 | 156 | 583 | 0 | 0 | 0 | 0 | 0 | 0 |
| C1 | B1 | 249 | 119 | 176 | 544 | 0 | 0 | 0 | 0 | 0 | 0 |
| C1 | B2 | 265 | 187 | 151 | 603 | 0 | 0 | 0 | 0 | 0 | 0 |
| C1 | C2 | 299 | 227 | 108 | 634 | 172 | 205 | 84 | 0 | 0.7520374 | 461 |
| C1 | D1 | 254 | 136 | 205 | 595 | 0 | 0 | 0 | 0 | 0 | 0 |
| C1 | D2 | 124 | 184 | 229 | 537 | 0 | 0 | 0 | 0 | 0 | 0 |
| C2 | A1 | 86 | 170 | 204 | 460 | 0 | 0 | 0 | 0 | 0 | 0 |
| C2 | A2 | 120 | 153 | 172 | 445 | 0 | 0 | 0 | 0 | 0 | 0 |
| C2 | B1 | 119 | 74 | 222 | 415 | 0 | 0 | 0 | 0 | 0 | 0 |
| C2 | B2 | 152 | 175 | 98 | 425 | 0 | 0 | 0 | 0 | 0 | 0 |
| C2 | C1 | 149 | 189 | 71 | 409 | 92 | 62 | 32 | 0 | 0.4653987 | 186 |
| C2 | D1 | 163 | 126 | 155 | 444 | 0 | 0 | 0 | 0 | 0 | 0 |
| C2 | D2 | 96 | 115 | 222 | 433 | 0 | 0 | 0 | 0 | 0 | 0 |
| D1 | A1 | 81 | 160 | 103 | 344 | 0 | 0 | 0 | 0 | 0 | 0 |
| D1 | A2 | 153 | 116 | 61 | 330 | 0 | 0 | 0 | 0 | 0 | 0 |
| D1 | B1 | 354 | 108 | 101 | 563 | 0 | 0 | 0 | 0 | 0 | 0 |
| D1 | B2 | 105 | 184 | 69 | 358 | 0 | 0 | 0 | 0 | 0 | 0 |
| D1 | C1 | 190 | 99 | 130 | 419 | 0 | 0 | 0 | 0 | 0 | 0 |
| D1 | C2 | 228 | 52 | 56 | 336 | 0 | 0 | 0 | 0 | 0 | 0 |
| D1 | D2 | 111 | 271 | 75 | 457 | 94 | 34 | 27 | 0 | 0.4441027 | 155 |
| D2 | A1 | 262 | 165 | 61 | 488 | 0 | 0 | 0 | 0 | 0 | 0 |
| D2 | A2 | 107 | 120 | 173 | 400 | 0 | 0 | 0 | 0 | 0 | 0 |
| D2 | B1 | 152 | 159 | 150 | 461 | 0 | 0 | 0 | 0 | 0 | 0 |
| D2 | B2 | 343 | 252 | 249 | 844 | 0 | 0 | 0 | 0 | 0 | 0 |
| D2 | C1 | 245 | 96 | 164 | 505 | 0 | 0 | 0 | 0 | 0 | 0 |
| D2 | C2 | 185 | 247 | 194 | 626 | 0 | 0 | 0 | 0 | 0 | 0 |
| D2 | D1 | 82 | 49 | 179 | 310 | 38 | 10 | 39 | 0 | 0.2951245 | 87 |

Key

| Shorthand ID | Stock Description |
|---|---|
| WT | Wildtype (OreR) |
| A1 | Rescue line 986C/9732 1045A |
| A2 | Rescue line 986C/8622 1045A |
| B1 | Rescue line 986C/9732 1045B |
| B2 | Rescue line 986C/8622 1045B |
| C1 | Rescue line 986C/9732 1045C |
| C2 | Rescue line 986C/8622 1045C |
| D1 | Rescue line 986C/8622 1045D |
| D2 | Rescue line 986C/86Fa 1045D |

TABLE 8

| Embryo collections for RNA sequence | | | | |
|---|---|---|---|---|
| Sample ID | Type | Female | Male | Notes |
| 1 | Con- | 874W | 874W | Cas9 |
| 2 | trols | 986C | 986C | dCas9-VPR |
| 3 | | WT | WT | WT |
| 4 | | dgRNAA | dgRNAA | 2 gRNAs targetting 2 genes (eve, hid) |
| 5 | | dgRNAB | dgRNAB | 4 gRNAs targetting 3 genes (eve, hid, hh) |
| 6 | | dgRNAC | dgRNAC | 4 gRNAs targetting 3 genes (eve, hid, wg) |
| 7 | | dgRNAD | dgRNAD | 4 gRNAs targetting 2 genes (wg, hh) |
| 8 | Experi- | WT | A1 | outcross to WT females |
| 9 | mental | WT | A2 | (Synthetic Lethality) |
| 10 | | WT | B1 | |
| 11 | | WT | C1 | |
| 12 | | WT | D1 | |
| 13 | | WT | D2 | |
| 14 | | A1 | A1 | Homozygous speciation |
| 15 | | A2 | A2 | stocks |
| 16 | | B1 | B1 | |
| 17 | | C1 | C1 | |
| 18 | | D1 | D1 | |
| 19 | | D2 | D2 | |
| 20 | | WT | B2 | outcross to WT females |
| 21 | | WT | C2 | |
| 22 | | B2 | B2 | Homozygous speciation |
| 23 | | C2 | C2 | stocks |

TABLE 8-continued

Key

| Shorthand ID | Stock Description |
|---|---|
| 874W | Ubiq-Cas9 Line |
| 986C | attp40W dCas9 VPR line |
| WT | Wildtype (OreR) |
| A1 | Rescue line 986C/9732 1045A |
| A2 | Rescue line 986C/8622 1045A |
| B1 | Rescue line 986C/9732 1045B |
| B2 | Rescue line 986C/8622 1045B |
| C1 | Rescue line 986C/9732 1045C |
| C2 | Rescue line 986C/8622 1045C |
| D1 | Rescue line 986C/8622 1045D |
| D2 | Rescue line 986C/86Fa 1045D |
| dgRNAA | 9732 1045A hom |
| dgRNAB | 9732 1045B hom |
| dgRNAC | 9732 1045C hom |
| dgRNAD | 8622 1045D hom |

TABLE 9

TPM analysis for genes of interest.

| | Other—Controls | | | gRNA Controls | | | |
|---|---|---|---|---|---|---|---|
| | Wildtype | Cas9 | dCas9 | dgRNA-A | dgRNA-B | dgRNA-C | dgRNA-D |
| | ID | | | | | | |
| | 21837.WT_IS_3_STAR | 21835.874W_IS_1_STAR | 21836.986C_IS_2_STAR | 21880.dgRNAC_IS_6_STAR | 21838.dgRNAA_IS_4_STAR | 21839.dgRNAB_IS_5_STAR | 21840.dgRNAD_IS_7_STAR |
| GFP | 0.061228789 | 241.9422974 | 70.5295293 | 5.3495308 | 0.24498658 | 0.22056 | 0 |
| SpCas9 | 0.021499502 | 275.6710094 | 0.1368249 | 0 | 0.12903463 | 0 | 0 |
| dCas9-VPR | 0 | 0 | 84.6457937 | 0.0146052 | 0 | 0 | 0 |
| dsRed | 0.258941134 | 60.06593268 | 1.09861754 | 0 | 0.77704995 | 0 | 0.74591029 |
| eCFP | 0.428601524 | 129.8568259 | 123.394204 | 4.5354717 | 0.12249329 | 0.661679 | 0 |
| eve_gRNA | 0 | 0 | 0 | 0 | 1.097748383 | 0.27874991 | 0.51722871 |
| hh_gRNA_1 | 0 | 0 | 0 | 0 | 0.156178946 | 0.27294262 | 1.26235327 |
| hh_gRNA_2 | 0 | 0 | 0 | 0 | 0.156178946 | 0.27294262 | 0.50645311 |
| hid_gRNA | 0 | 0 | 0 | 0 | 0.159501902 | 0.27874991 | 0.51722871 |
| wg_gRNA_1 | 0 | 0 | 0 | 0 | 0.156178946 | 0.27294262 | 0.50645311 |
| wg_gRNA_2 | 0 | 0 | 0 | 0 | 0.156178946 | 0.27294262 | 1.26235327 |
| white | 1.108513474 | 0.146157136 | 0.26002851 | 0.0708562 | 1.066189184 | 1.9485617 | 1.83345996 |
| FBgn0000606 (eve) | 13.54523653 | 40.88082311 | 23.7457859 | 21.647585 | 18.0028546 | 16.01019 | 12.6707361 |
| FBgn0004644 (hh) | 23.10262968 | 12.49822353 | 13.7714837 | 0.3532987 | 11.6849296 | 14.40618 | 20.545175 |
| FBgn0284084 (wg) | 50.35234108 | 28.13019982 | 32.1664601 | 2.0940118 | 25.2892623 | 27.25601 | 44.4745862 |
| FBgn0003997 (hid) | 49.4609145 | 19.18230562 | 24.7415546 | 5.3973451 | 33.03477594 | 36.8155738 | 36.1206647 |

| | Synthetic Lethality | | | | | | | |
|---|---|---|---|---|---|---|---|---|
| | ID | | | | | | | |
| | 21841.WTxA1_IS_8_STAR | 21842.WTxA2_IS_9_STAR | 21843.WTxB1_IS_10_STAR | 21932.WTxB2_IS_20_STAR | 21844.WTxC1_IS_11_STAR | 21933.WTxC2_IS_21_STAR | 21845.WTxD1_IS_12_STAR | 21846.WTXD2_IS_13_STAR |
| GFP | 60.74601735 | 51.12536714 | 60.76987 | 56.31678 | 25.7243686 | 47.62414 | 74.626607 | 66.204315 |
| SpCas9 | 0 | 0 | 0 | 0 | 0 | 0 | 0 | 0.044662 |
| dCas9-VPR | 28.57274186 | 47.77051574 | 51.7773249 | 41.235216 | 19.86679689 | 65.1760078 | 32.2182978 | 30.510511 |
| dsRed | 0 | 0.116871895 | 0.133299 | 0 | 0 | 0 | 0.1562384 | 1.8826907 |
| eCFP | 111.3979204 | 95.01027689 | 115.23582 | 100.38143 | 49.89907643 | 84.2953357 | 141.125563 | 124.71341 |
| eve_gRNA | 0 | 0.143938929 | 0 | 0.9631568 | 0 | 0.30591516 | 0.19242251 | 1.1398719 |
| hh_gRNA_1 | 0 | 0.140940201 | 0.94558933 | 0.9430911 | 0 | 0.29954193 | 2.40504559 | 1.1161246 |
| hh_gRNA_2 | 0 | 0.140940201 | 0 | 0.1370303 | 0 | 0.29954193 | 0.18841371 | 2.0700773 |
| hid_gRNA | 0 | 0.143938929 | 0 | 0.1399459 | 0 | 0.30591516 | 0.19242251 | 1.1398719 |
| wg_gRNA_1 | 0 | 0.140940201 | 0 | 0.1370303 | 0 | 3.02265041 | 2.40504559 | 5.8858879 |
| wg_gRNA_2 | 0 | 0.140940201 | 0 | 0.1370303 | 0 | 0.29954193 | 0.18841371 | 1.1161246 |
| white | 0.978558206 | 0.740862135 | 1.30590094 | 0.4677335 | 0.496371028 | 0.83220723 | 1.87792024 | 1.2067409 |
| FBgn0000606 (eve) | 222.9524959 | 184.2565229 | 251.895314 | 129.77692 | 86.56233058 | 138.022477 | 18.237552 | 19.572992 |

TABLE 9-continued

| TPM analysis for genes of interest. | | | | | | | | |
|---|---|---|---|---|---|---|---|---|
| FBgn0004644 (hh) | 25.00996052 | 17.86571845 | 45.0818692 | 33.825981 | 10.8468407 | 30.03922 | 42.1552878 | 29.676381 |
| FBgn0284084 (wg) | 49.61733877 | 35.20054167 | 57.40787 | 50.71307 | 33.6676143 | 79.2882615 | 79.0606298 | 64.535437 |
| FBgn0003997 (hid) | 45.75075039 | 39.16101468 | 44.2360716 | 37.535387 | 18.39414152 | 44.4806011 | 23.1968485 | 22.404829 |

| | Speciated Stocks ID | | | | | | | |
|---|---|---|---|---|---|---|---|---|
| | 21847.A1_IS_14_STAR | 21848.A2_IS_15_STAR | 21849.B1_IS_16_STAR | 21934.B2_IS_22_STAR | 21850.C1_IS_17_STAR | 21935.C2_IS_23_STAR | 21851.D1_IS_18_STAR | 21852.D2_IS_19_STAR |
| GFP | 89.66518109 | 150.9864446 | 116.048 | 134.6456 | 136.038286 | 70.5406 | 154.23194 | 40.416947 |
| SpCas9 | 0 | 0 | 0.061771 | 0 | 0 | 0 | 0 | 0 |
| dCas9-VPR | 5.714049806 | 7.418279388 | 22.2407389 | 63.46419 | 16.30646224 | 107.856983 | 25.2897317 | 36.006945 |
| dsRed | 1.023483848 | 0.26462204 | 0.495983 | 0.120386 | 0 | 0 | 0 | 0.3268189 |
| eCFP | 165.7777302 | 269.1225439 | 220.30934 | 243.72839 | 250.0318526 | 131.10457 | 289.902625 | 77.201778 |
| eve_gRNA | 5.561110379 | 1.917102224 | 0 | 0.2878124 | 1.46828847 | 0 | 1.19669322 | 0.2012544 |
| hh_gRNA_1 | 0.907542319 | 0 | 0.87959545 | 0.2818163 | 0.479233042 | 0 | 1.17176211 | 0.1970616 |
| hh_gRNA_2 | 0.907542319 | 0 | 0.87959545 | 0.2818163 | 0.479233042 | 0 | 2.17326818 | 1.3562475 |
| hid_gRNA | 3.707406919 | 0 | 0 | 0.2878124 | 0.48942949 | 0 | 1.19669322 | 0.2012544 |
| wg_gRNA_1 | 0.907542319 | 0 | 0 | 0.2818163 | 0.479233042 | 0.88029031 | 3.17477426 | 1.3562475 |
| wg_gRNA_2 | 0.907542319 | 0 | 0 | 0.2818163 | 1.437699127 | 0 | 1.17176211 | 0.1970616 |
| white | 2.001157144 | 1.187296264 | 1.71495592 | 0.376614 | 2.44714745 | 0.67426492 | 3.1614273 | 2.1524534 |
| FBgn0000606 (eve) | 4.585476979 | 6.216265318 | 9.158803 | 14.72311 | 7.36232839 | 27.46806 | 9.5050477 | 14.761069 |
| FBgn0004644 (hh) | 12.90318395 | 23.07721913 | 17.4583 | 20.75517 | 18.4025488 | 15.90317 | 21.054447 | 8.8274204 |
| FBgn0284084 (wg) | 23.57931122 | 41.98053242 | 33.52768 | 41.48296 | 34.1068137 | 34.85696 | 40.809571 | 12.961914 |
| FBgn0003997 (hid) | 29.20759391 | 53.66311702 | 32.8002851 | 33.748071 | 40.79659125 | 24.755043 | 43.9565952 | 14.01409 |

TABLE 10

DEseq analysis comparing species outcrosses to species inbreeding.

| Test | GeneId | Gene* | baseMean | log2FoldChange | IfcSE | stat | pvalue | padj | FDR |
|---|---|---|---|---|---|---|---|---|---|
| WTxA_vs_A | FBgn0000606 | eve | 1768.253759 | 5.318942757 | 0.421735181 | 12.61204422 | 1.81E−36 | 4.60E−34 | 0.05 |
| WTxA_vs_A | FBgn0003997 | hid | 1969.984049 | 0.172408806 | 0.453438097 | 0.380225673 | 0.703777903 | 0.897087106 | |
| WTxA_vs_A | FBgn0004644 | hh | 549.2962598 | 0.368151183 | 0.543984858 | 0.676767336 | 0.498553586 | 0.778281351 | |
| WTxA_vs_A | FBgn0284084 | wg | 1292.079521 | 0.485461947 | 0.494921313 | 0.980887132 | 0.326648404 | 0.628493479 | |
| WTxB_vs_B | FBgn0000606 | eve | 1675.935244 | 3.882046764 | 0.406766299 | 9.543678458 | 1.38E−21 | 1.48E−18 | 0.05 |
| WTxB_vs_B | FBgn0003997 | hid | 1784.374549 | 0.216262706 | 0.233063653 | 0.927912626 | 0.353452895 | 0.643185096 | |
| WTxB_vs_B | FBgn0004644 | hh | 825.9915912 | 0.959766415 | 0.344054527 | 2.789576477 | 0.005277703 | 0.059403411 | 0.1 |
| WTxB_vs_B | FBgn0284084 | wg | 1596.527448 | 0.455975445 | 0.261026933 | 1.746852094 | 0.080662998 | 0.294057171 | |
| WTxC_vs_C | FBgn0000606 | eve | 1061.904668 | 3.038049072 | 0.660731209 | 4.598010556 | 4.27E−06 | 0.004238785 | 0.05 |
| WTxC_vs_C | FBgn0003997 | hid | 1487.554802 | −0.054230348 | 0.779245663 | −0.069593391 | 0.944517298 | 0.999999667 | |
| WTxC_vs_C | FBgn0004644 | hh | 512.1340749 | 0.175875505 | 0.857806448 | 0.205029357 | 0.837549188 | 0.999999667 | |
| WTxC_vs_C | FBgn0284084 | wg | 1529.729277 | 0.681046335 | 0.669484299 | 1.017270063 | 0.309024974 | 0.999999667 | |
| WTxD_vs_D | FBgn0000606 | eve | 213.9655785 | 0.633866887 | 0.509632601 | 1.24377225 | 0.213583396 | 0.545623791 | |
| WTxD_vs_D | FBgn0003997 | hid | 1010.500041 | −0.163715708 | 0.455826313 | −0.359162478 | 0.719473545 | 0.908959863 | |
| WTxD_vs_D | FBgn0004644 | hh | 585.4075446 | 1.333563143 | 0.431374561 | 3.091427412 | 0.001991967 | 0.030323774 | 0.05 |
| WTxD_vs_D | FBgn0284084 | wg | 1396.728336 | 1.592570402 | 0.431420943 | 3.691453617 | 0.000222976 | 0.005638109 | 0.05 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. E. Moreno, Design and Construction of "Synthetic Species." *PLoS One.* 7, e39054 (2012).
2. M. Maselko, S. C. Heinsch, J. M. Chacón, W. R. Harcombe, M. J. Smanski, Engineering species-like barriers to sexual reproduction. *Nat. Commun.* 8, 883 (2017).
3. N. R. Burgos, V. Singh, T. M. Tseng, H. Black, N. D. Young, Z. Huang, K. E. Hyma, D. R. Gealy, A. L. Caicedo, The impact of herbicide-resistant rice technology on phenotypic diversity and population structure of United States weedy rice. *Plant Physiol.* 166, 1208-1220 (2014).
4. A. J. Waters, P. Capriotti, D. C. A. Gaboriau, P. A. Papathanos, N. Windbichler, Rationally-engineered reproductive barriers using CRISPR & CRISPRa: an evaluation of the synthetic species concept in *Drosophila melanogaster. Sci. Rep.* 8, 13125 (2018).
5. O. S. Akbari, K. D. Matzen, J. M. Marshall, H. Huang, C. M. Ward, B. A. Hay, A synthetic gene drive system for local, reversible modification and suppression of insect populations. *Curr. Biol.* 23, 671-677 (2013).
6. A. B. Buchman, T. Ivy, J. M. Marshall, O. S. Akbari, B. A. Hay, Engineered Reciprocal Chromosome Translocations Drive High Threshold, Reversible Population Replacement in *Drosophila. ACS Synth. Biol.* 7, 1359-1370 (2018).
7. J. Champer, A. Buchman, O. S. Akbari, Cheating evolution: engineering gene drives to manipulate the fate of wild populations. *Nat. Rev. Genet.* 17, 146-159 (2016).
8. K. M. Esvelt, A. L. Smidler, F. Catteruccia, G. M. Church, Concerning RNA-guided gene drives for the alteration of wild populations. *Elife.* 3 (2014), doi:10.7554/eLife.03401.
9. P. T. Leftwich, M. P. Edgington, T. Harvey-Samuel, L. Z. Carabajal Paladino, V. C. Norman, L. Alphey, Recent advances in threshold-dependent gene drives for mosquitoes. *Biochem. Soc. Trans.* 46, 1203-1212 (2018).
10. M. J. Lajoie, A. J. Rovner, D. B. Goodman, H.-R. Aerni, A. D. Haimovich, G. Kuznetsov, J. A. Mercer, H. H. Wang, P. A. Carr, J. A. Mosberg, N. Rohland, P. G. Schultz, J. M. Jacobson, J. Rinehart, G. M. Church, F. J. Isaacs, Genomically recoded organisms expand biological functions. *Science.* 342, 357-360 (2013).
11. A. J. Rovner, A. D. Haimovich, S. R. Katz, Z. Li, M. W. Grome, B. M. Gassaway, M. Amiram, J. R. Patel, R. R. Gallagher, J. Rinehart, F. J. Isaacs, Recoded organisms engineered to depend on synthetic amino acids. *Nature.* 518, 89-93 (2015).
12. J. D. Boeke, G. Church, A. Hessel, N. J. Kelley, A. Arkin, Y. Cai, R. Carlson, A. Chakravarti, V. W. Cornish, L. Holt, F. J. Isaacs, T. Kuiken, M. Lajoie, T. Lessor, J. Lunshof, M. T. Maurano, L. A. Mitchell, J. Rine, S. Rosser, N. E. Sanjana, P. A. Silver, D. Valle, H. Wang, J. C. Way, L. Yang, GENOME ENGINEERING. The Genome Project-Write. *Science.* 353, 126-127 (2016).
13. J. L. Foo, M. W. Chang, Synthetic yeast genome reveals its versatility. *Nature.* 557 (2018), pp. 647-648.

14. R. G. Reeves, J. Bryk, P. M. Altrock, J. A. Denton, F. A. Reed, First steps towards underdominant genetic transformation of insect populations. *PLoS One.* 9, e97557 (2014).

15. S. Lin, B. Ewen-Campen, X. Ni, B. E. Housden, N. Perrimon, In Vivo Transcriptional Activation Using CRISPR/Cas9 in *Drosophila. Genetics.* 201, 433-442 (2015).

16. B. Ewen-Campen, D. Yang-Zhou, V. R. Fernandes, D. P. González, L.-P. Liu, R. Tao, X. Ren, J. Sun, Y. Hu, J. Zirin, S. E. Mohr, J.-Q. Ni, N. Perrimon, Optimized strategy for in vivo Cas9-activation in *Drosophila. Proc. Natl. Acad. Sci. U.S.A.* 114, 9409-9414 (2017).

17. S. Cho, D. Choe, E. Lee, S. C. Kim, B. Palsson, B.-K. Cho, High-Level dCas9 Expression Induces Abnormal Cell Morphology in *Escherichia coli. ACS Synthetic Biology.* 7 (2018), pp. 1085-1094.

18. M. P. Edgington, L. S. Alphey, Population dynamics of engineered underdominance and killer-rescue gene drives in the control of disease vectors. *PLoS Comput. Biol.* 14, e1006059 (2018).

19. J. M. Marshall, O. S. Akbari, Can CRISPR-Based Gene Drive Be Confined in the Wild?A Question for Molecular and Population Biology. *ACS Chemical Biology.* 13 (2018), pp. 424-430.

20. A. Buchman, S. Gamez, M. Li, I. Antoshechkin, H.-H. Li, H.-W. Wang, C.-H. Chen, M. J. Klein, J.-B. Duchemin, P. N. Paradkar, O. S. Akbari, Engineered resistance to Zika virus in transgenic expressing a polycistronic cluster of synthetic small RNAs. *Proc. Natl. Acad. Sci. U S. A.* 116, 3656-3661 (2019).

21. A. Buchman, S. Gamez, M. Li, I. Antoshechkin, S.-H. Lee, S.-W. Wang, C.-H. Chen, M. J. Klein, J.-B. Duchemin, J. E. Crowe, P. N. Paradkar, O. Akbari, Broad Dengue Neutralization in Mosquitoes Expressing an Engineered Antibody. *SSRN Electronic Journal* (2019), doi:10.2139/ssm.3398490.

22. K. Kyrou, A. M. Hammond, R. Galizi, N. Kranjc, A. Burt, A. K. Beaghton, T. Nolan, A. Crisanti, A CRISPR-Cas9 gene drive targeting doublesex causes complete population suppression in caged *Anopheles gambiae* mosquitoes. *Nat. Biotechnol.* 36, 1062-1066 (2018).

REFERENCES FOR MATERIALS AND METHODS

1. M. Li, M. Bui, T. Yang, C. S. Bowman, B. J. White, O. S. Akbari, Germline Cas9 expression yields highly efficient genome engineering in a major worldwide disease vector, *Aedes aegypti*. Proc. Natl. Acad. Sci. U.S.A. 114, E10540-E10549 (2017).

2. D. G. Gibson, L. Young, R.-Y. Chuang, J. C. Venter, C. A. Hutchison 3rd, H. O. Smith, Enzymatic assembly of DNA molecules up to several hundred kilobases. Nat. Methods. 6, 343-345 (2009).

3. J. Bischof, R. K. Maeda, M. Hediger, F. Karch, K. Basler, An optimized transgenesis system for *Drosophila* using germ-line-specific φC31 integrases. Proc. Natl. Acad. Sci. U.S.A. 104, 3312-3317 (2007).

4. A. B. Buchman, T. Ivy, J. M. Marshall, O. S. Akbari, B. A. Hay, Engineered Reciprocal Chromosome Translocations Drive High Threshold, Reversible Population Replacement in *Drosophila*. ACS Synth. Biol. 7, 1359-1370 (2018).

5. A. Chavez, M. Tuttle, B. W. Pruitt, B. Ewen-Campen, R. Chari, D. Ter-Ovanesyan, S. J. Haque, R. J. Cecchi, E. J. K. Kowal, J. Buchthal, B. E. Housden, N. Perrimon, J. J. Collins, G. Church, Comparison of Cas9 activators in multiple species. Nat. Methods. 13, 563-567 (2016).

6. F. Port, H.-M. Chen, T. Lee, S. L. Bullock, Optimized CRISPR/Cas tools for efficient germline and somatic genome engineering in *Drosophila*. Proc. Natl. Acad. Sci. U.S.A 111, E2967-76 (2014).

7. A. J. Waters, P. Capriotti, D. C. A. Gaboriau, P. A. Papathanos, N. Windbichler, Rationally-engineered reproductive barriers using CRISPR & CRISPRa: an evaluation of the synthetic species concept in *Drosophila melanogaster*. Sci. Rep. 8, 13125 (2018).

8. B. Ewen-Campen, D. Yang-Zhou, V. R. Fernandes, D. P. González, L.-P. Liu, R. Tao, X. Ren, J. Sun, Y. Hu, J. Zirin, S. E. Mohr, J.-Q. Ni, N. Perrimon, Optimized strategy for in vivo Cas9-activation in *Drosophila*. Proc. Natl. Acad. Sci. U.S.A. 114, 9409-9414 (2017).

9. F. Port, S. L. Bullock, Augmenting CRISPR applications in *Drosophila* with tRNA-flanked sgRNAs. Nat. Methods. 13, 852-854 (2016).

10. N. P. Kandul, J. Liu, H. M. Sanchez C., S. L. Wu, J. M. Marshall, O. S. Akbari, Transforming insect population control with precision guided sterile males with demonstration in flies. Nature Communications. 10 (2019), doi:10.1038/s41467-018-07964-7.

11. J. K. Grenier, J. Roman Arguello, M. C. Moreira, S. Gottipati, J. Mohammed, S. R. Hackett, R. Boughton, A. J. Greenberg, A. G. Clark, Global Diversity Lines-A Five-Continent Reference Panel of Sequenced *Drosophila melanogaster* Strains. G3: Genes|Genomes|Genetics. 5 (2015), pp. 593-603.

12. J. Champer, R. Reeves, S. Y. Oh, C. Liu, J. Liu, A. G. Clark, P. W. Messer, Novel CRISPR/Cas9 gene drive constructs reveal insights into mechanisms of resistance allele formation and drive efficiency in genetically diverse populations. PLOS Genetics. 13 (2017), p. e1006796.

13. G. Oberhofer, T. Ivy, B. A. Hay, Cleave and Rescue, a novel selfish genetic element and general strategy for gene drive. Proc. Natl. Acad. Sci. U.S.A. 116, 6250-6259 (2019).

14. A. Dobin, C. A. Davis, F. Schlesinger, J. Drenkow, C. Zaleski, S. Jha, P. Batut, M. Chaisson, T. R. Gingeras, STAR: ultrafast universal RNA-seq aligner. Bioinformatics. 29, 15-21 (2013).

15. Y. Liao, G. K. Smyth, W. Shi, featureCounts: an efficient general purpose program for assigning sequence reads to genomic features. Bioinformatics. 30, 923-930 (2014).

16. M. I. Love, W. Huber, S. Anders, Moderated estimation of fold change and dispersion for RNA-seq data with DESeq2. Genome Biol. 15, 550 (2014).

17. H. Wickham, ggplot2: Elegant Graphics for Data Analysis (Springer, 2016).

18. Thurmond J, Goodman J L, Strelets V B, Attrill H, Gramates L S, Marygold S J, Matthews B B, Millbum G, Antonazzo G, Trovisco V, Kaufman T C, Calvi B R and the FlyBase Consortium. (2019) FlyBase 2.0: the next generation. Nucleic Acids Res. 47(D1) D759-D765

What is claimed is:

1. A method of engineering a reproductive barrier in an insect comprising:

(a) genetically crossing a first insect with a second insect to produce a population of progeny insects, wherein the first insect comprises a first nucleic acid sequence encoding a CRISPR-associated (Cas) endonuclease and the second insect comprises two or more sgRNA sequences, wherein a sgRNA target sequence is proximal to a transcription start site of a developmental gene, and wherein the sgRNA target sequence is operably linked to a ubiquitous promoter; and (b) genetically crossing a female progeny insect comprising a mutation in the sgRNA target sequence with a male insect comprising a second nucleic acid sequence encoding a nuclease-deficient endonuclease fused to a transcriptional activator to produce an insect with a reproductive barrier.

2. The method of claim 1, wherein step (a) comprises integrating the first nucleic acid sequence into the genome of the first insect, and wherein step (b) comprises integrating the second nucleic acid sequence into the genome of the male insect.

3. The method of claim 1, wherein the ubiquitous promoter is a ubiquitin-63E promoter.

4. The method of claim 1, wherein the nuclease-deficient endonuclease comprises a CRISPR-associated sequence 9 (Cas9) endonuclease or a variant thereof, a CRISPR-associated sequence 13 (Cas13) endonuclease or a variant thereof, a CRISPR from *Prevotella* and *Francisella* 1 (Cpf1) endonuclease or a variant thereof, a CRISPR from Microgenomates and *Smithella* 1 (Cms1) endonuclease or a variant thereof, or a CRISPR-associated sequence 6 (Cas6) endonuclease or a variant thereof.

5. The method of claim 1, wherein the nuclease-deficient endonuclease comprises a *Streptococcus pyogenes* Cas9 (SpCas9), a *Staphylococcus aureus* Cas9 (SaCas9), a *Francisella novicida* Cas9 (FnCas9), or a variant thereof, and wherein the variant thereof comprises a protospacer adjacent motif (PAM) SpCas9 (xCas9), a high fidelity SpCas9, a high fidelity SaCas9, or a high fidelity FnCas9.

6. The method of claim 1, wherein the nuclease-deficient endonuclease comprises a Cas9 protein or a variant thereof fused with a FokI nuclease or variant thereof.

7. The method of claim 1, wherein the nuclease-deficient endonuclease comprises a CRISPR-associated sequence 9 (dCas9) endonuclease or a variant thereof, and wherein the variant thereof comprises a first amino acid substitution of D10A and a second amino acid substitution of H840A.

8. The method of claim 1, wherein the transcriptional activator comprises at least one of a SunTag, a SAM, a VPR, or a VP64.

9. The method of claim 1, wherein the CRISPR-associated (Cas) endonuclease comprises a CRISPR-associated sequence 9 (Cas9) endonuclease or a variant thereof, a CRISPR-associated sequence 13 (Cas13) endonuclease or a variant thereof, a CRISPR from *Prevotella* and *Francisella* 1 (Cpf1) endonuclease or a variant thereof, a CRISPR from Microgenomates and *Smithella* 1 (Cms1) endonuclease or a variant thereof, or a CRISPR-associated sequence 6 (Cas6) endonuclease or a variant thereof.

10. The method of claim 1, wherein the CRISPR-associated sequence 9 (Cas9) endonuclease comprises a *Streptococcus pyogenes* Cas9 (SpCas9), a *Staphylococcus aureus* Cas9 (SaCas9), a *Francisella novicida* Cas9 (FnCas9), or a variant thereof, and wherein the variant thereof comprises a protospacer adjacent motif (PAM) SpCas9 (xCas9), a high fidelity SpCas9, a high fidelity SaCas9, or a high fidelity FnCas9.

11. The method of claim 1, wherein the mutation prevents the sgRNA from targeting the sgRNA target sequence, and wherein the mutation does not alter expression of the developmental gene product.

12. The method of claim 1, wherein the developmental gene product comprises at least one of even skipped (eve), head involution defective (hid), hedgehog (hh), or wingless (wg), or a combination thereof, and wherein the combination of the developmental gene products comprises at least one of: (i) eve and hid; (ii) eve, hid, and hh; (iii) eve, hid, and wg; or (iv) hh and wg.

13. The method of claim 1, wherein the first insect is a mosquito from the genera *Stegomyia, Aedes, Anopheles*, or *Culex* and the second insect is a mosquito from the genera *Stegomyia, Aedes, Anopheles*, or *Culex*, and wherein the first mosquito and/or the second mosquito comprises *Aedes aegypti, Aedes albopictus, Ochlerotatus triseriatus* (*Aedes triseriatus*), *Anopheles stephensi, Anopheles albimanus, Anopheles gambiae, Anopheles quadrimaculatus, Anopheles freeborni, Culex species*, or *Culiseta melanura.*

14. A genetically modified insect produced by the method of claim 1.

* * * * *